United States Patent
Zhang et al.

(10) Patent No.: US 10,072,043 B2
(45) Date of Patent: Sep. 11, 2018

(54) INHIBITORS OF PROTEIN TYROSINE PHOSPHATASES

(71) Applicant: Indiana University Research and Technology Corporation, Indianapolis, IN (US)

(72) Inventors: Zhong-Yin Zhang, Carmel, IN (US); Sheng Zhang, Carmel, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 115 days.

(21) Appl. No.: 14/975,232

(22) Filed: Dec. 18, 2015

(65) Prior Publication Data

US 2016/0176922 A1    Jun. 23, 2016

Related U.S. Application Data

(62) Division of application No. 13/260,623, filed as application No. PCT/US2010/030409 on Apr. 8, 2010, now Pat. No. 9,217,012.

(60) Provisional application No. 61/167,627, filed on Apr. 8, 2009.

(51) Int. Cl.
| | |
|---|---|
| *A61K 38/06* | (2006.01) |
| *C07K 5/087* | (2006.01) |
| *C07K 5/065* | (2006.01) |
| *C12Q 1/42* | (2006.01) |
| *G01N 33/50* | (2006.01) |
| *A61K 38/00* | (2006.01) |

(52) U.S. Cl.
CPC ........ *C07K 5/0812* (2013.01); *C07K 5/06078* (2013.01); *C12Q 1/42* (2013.01); *G01N 33/505* (2013.01); *A61K 38/00* (2013.01); *G01N 2333/916* (2013.01)

(58) Field of Classification Search
CPC .... C07K 5/0812; C07K 5/06078; C12Q 1/42; G01N 33/505; G01N 2333/916; A61K 38/00
USPC ........................................................ 530/331
See application file for complete search history.

(56) References Cited

FOREIGN PATENT DOCUMENTS

| WO | WO 02/04458 A1 | 1/2002 |
|---|---|---|
| WO | WO 03/073987 A2 | 9/2003 |

OTHER PUBLICATIONS

International Searching Authority, International Search Report and Written Opinion for PCT/US10/30409, dated Nov. 2010.
Zhang et al., PTP1B as a Drug Target: Recent Developments in PTP1B Inhibitor Discovery, Drug Discovery Today vol. 12, pp. 373-381, May 2007.
Iversen et al., Structure Determination of T Cell Protein-tyrosine Phosphatase, J Biol Chem 277 (22), pp. 19982-19990, 2002.
Zhang et al., An Affinity-Based Fluorescence Polarization Assay for Protein Tyrosine Phosphatases, Methods 42 (3), pp. 1-14, Jul. 2007.

*Primary Examiner* — Sreenivasan Padmanabhan
*Assistant Examiner* — Y Jeanmarie Z Calvillo
(74) *Attorney, Agent, or Firm* — Faegre Baker Daniels LLP

(57) ABSTRACT

Disclosed herein are compounds that selectively inhibit members of the PTP family of enzymes. Synthesized compounds demonstrated selective inhibition of TC-PTP. Also provided are methods of using the compounds and formulations containing the compounds. Also described is a fluorescence-tagged combinatorial library synthesis and screening method. And methods of using these compounds to effect enzyme activity both in cells and in vitro as well as method of using these compounds to treat diseases in human and animals.

9 Claims, 3 Drawing Sheets

INHIBITORS OF PROTEIN TYROSINE PHOSPHATASES

PRIORITY CLAIM

This application is a Divisional application of U.S. patent application Ser. No. 13/260,623 filed Dec. 13, 2011, which claims the benefit of PCT Application No. PCT/US10/30409 filed Apr. 8, 2010, which claims the benefit of U.S. Provisional Application No. 61/167,627 filed Apr. 8, 2009, the complete disclosures of all of which are hereby expressly incorporated by reference.

GOVERNMENT RIGHTS

This invention was made with government support under CA126937 awarded by the National Institutes of Health. The United States Government has certain rights in the invention.

BACKGROUND

Protein tyrosine phosphatases (PTPs) are an enzyme family comprising multiple enzyme subtypes, or isozymes, with differential activity and various distributions in the body. PTPs control a broad spectrum of cellular processes, for example, proliferation, differentiation, migration, apoptosis, and the immune responses (Alonso et al., 2004; Tonks, 2006). Dysfunction of PTP activity is associated with cancers, metabolic syndromes, and autoimmune disorders (Zhang, 2001). Compounds that can selectively inhibit particular PTPs are useful tools for studying the role of specific PTPs in normal and disease processes. Therapeutic compounds that can selectively inhibit specific PTPs are advantageous for treating diseases associated with excessive activity of a particular PTP. Use of a selective PTP can reduce the potential for undesirable effects due to nonselective inhibition of PTPs. However, the development of selective PTP inhibitors is problematic, in part due to the common architecture of the active site (i.e. pTyr-binding pocket) shared by members of the PTP family. Given the importance that these enzymes play in human and animal health there is currently a profound need for molecules that can preferentially inhibit some of these enzymes. Various aspects of the present invention address this need.

DESCRIPTION

Figure 1:
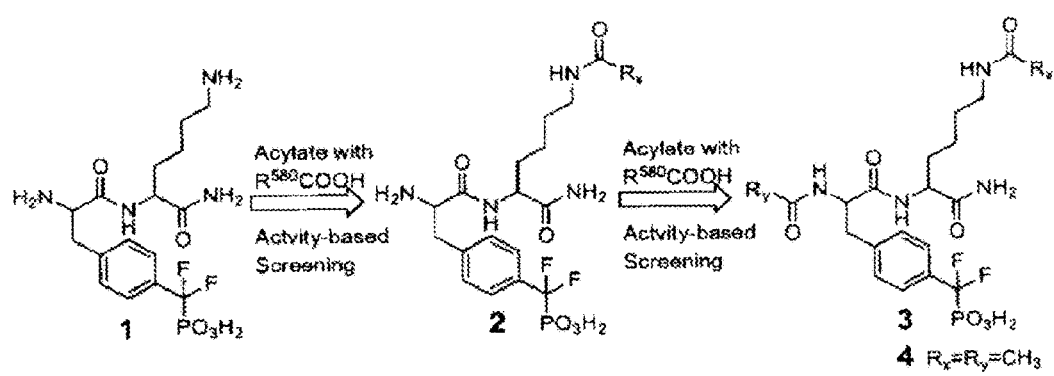
FIG. 1. Combinatorial library approach to target both the PTP active site and binding pockets immediately N- and C-terminal to pTyr.

Disclosed herein are compounds that inhibit PTPs, and particularly selectively inhibit isozymes of PTP. In one embodiment, the compounds disclosed herein selectively inhibit TC-PTP.

Another aspect of the invention is PTP inhibitor compounds which are synthesized by adding constituents to one or more amine groups of phosphonodifluoromethyl phenylalanine ($F_2$Pmp), for example, constituents comprising carboxylic acid residues.

In another embodiment, provided is a method for constructing and screening for a compound that selectively inhibits a target PTP isozyme relative to a comparative PTP isozyme, comprising the steps of providing a compound which binds to the active site region of said target PTP isozyme; supplying at least one additional peripheral moiety to said compound which binds to a region of the target PTP isozyme adjacent to or at least near to the active site; covalently bonding a fluorescein group to said compound; separately exposing said compound to the target PTP isozyme and comparative PTP isozyme; and measuring anisotropy values in a fluorescence polarization assay.

In another embodiment, a method of inhibiting the activity of a phosphatase and/or treating a disease, disorder, or condition associated with inappropriate activity of a protein phosphatase is disclosed comprising the steps of identifying a patient in need of a compound that regulates the activity of at least one phosphatase and providing the patient with a therapeutically effective dosage of at least one compound that at least partially inhibits the activity of at least one phosphatase, for example TC-PTP.

In one embodiment, the disease, disorder, or condition to be treated is type 1 diabetes, type 2 diabetes, obesity, metabolic syndrome, Crohn's disease, rheumatoid arthritis, Graves' disease, systemic lupus erythematosus, leukemia, or tuberculosis.

In one embodiment the phosphatase inhibitor has the formula:

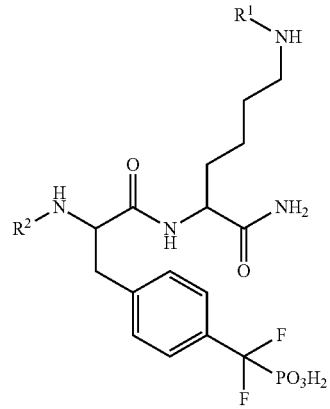

wherein $R^1$ and $R^2$ are the same or different and are each individually a residue of a carboxylic acid, and pharmaceutically acceptable salts thereof.

Some embodiments include at least one compound of the formula A

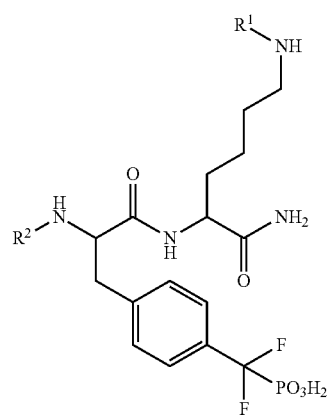

wherein R¹ and R² are the same or different and each individually is a residue of a carboxylic acid, and pharmaceutically acceptable salts thereof, wherein said carboxylic acid is selected from the group consisting of: 3-dimethylaminobenzoic acid, 2-(2-cyanophenylthio)benzoic acid, 2-(4-chlorobenzoyl)benzoic acid, (−)-2-oxo-4-thiazolidinecarboxylic acid, (−)-N-acetylneuraminic acid, (+)-6-methoxy-a-methyl-2-naphthaleneacetic acid, (+)-carbenzyloxy-D-proline, (+)-menthoxyacetic acid, (+_)-2-(2-chlorophenoxy)propionic acid, (±)-1-methyl-2-cyclohexene-1-carboxylic acid, (1-naphthoxy)acetic acid, (1R)-(1a,2b,3a)-(+)-3-methyl-2-nitromethyl-5-oxocyclopentaneacetic acid, (1R,4R)-7,7-dimethyl-2-oxobicyclo[2.2.1]heptane-1-carboxylic acid, (1S)-(+)-camphanic acid, (1S,3R,4S,5R)-1,3,4,5-tetrahydroxycyclohexanecarboxylic acid, (2,4-di-tert-pentylphenoxyl)acetic acid, (2-naphthoxy)acetic acid, (2-pyrimidylthio)acetic acid, (4-carboxybutyl)triphenyl-phosphonium bromide, (4-chlorophenylthio)acetic acid, (4-methylphenoxy)acetic acid, (a,a,a-trofluoro-m-tolyl)acetic acid, (E)-2-((4-hydroxyphenyl)diazenyl)benzoic acid, (E)-2-methyl-3-(2,4,5-trimethoxyphenyl)acrylic acid, (methylthio)acetic acid, (R)-(−)-2-hydroxy-4-phenylbutyric acid, (R)-(−)-3-chloromandelic acid, (R)-(−)-hexahydromandelic acid, (R)-(+)-2-pyrrolidone-5-carboxylic acid, (R)-(+)-citronellic acid, (R)-2-(1-phenylethylcarbamoyl)benzoic acid, (R)-2-hydroxy-2-phenylacetic acid, (R)-3,3,3-trifluoro-2-methoxy-2-phenylpropanoic acid, (R)-6-hydroxy-2,5,7,8-tetramethylchroman-2-carboxylic acid, (S)-(−)-indoline-2-carboxylic acid, (S)-(+)-2-oxo-4-phenyl-3-oxazolidineacetic acid, (S)-(+)-5-oxo-2-tetrahydrofurancarboxylic acid, (S)-(+)-hexahydromandelic acid, (S)-(+)-N-[1-(1-naphthyl)-ethyl]-phthalamic acid, (S)-(+)-O-acetylmandelic acid, (S)-2-(1-phenylethylcarbamoyl)benzoic acid, (S)-2-(4-isobutylphenyl)propanoic acid, (S)-2-(phenylcarbamoyloxy)propanoic acid, (S)-3-(benzyloxycarbonyl)-2-oxoimidazolidine-4-carboxylic acid, (S)-3,3,3-trifluoro-2-methoxy-2-phenylpropanoic acid, (S)-3,3,3-trifluoro-2-methoxy-2-phenylpropanoic acid, (S)-6-methoxy-2,5,7,8-tetramethylchroman-2-carboxylic acid, (trimethylsilyl)acetic acid, (z)-2-cyano-3-(3-hydroxyphenyl)acrylic acid, 1-(4-chlorophenyl)-1-cyclopentanecarboxylic acid, 1-(tert-butyl)hydrocinnamic acid, 1,2-phenylenedioxydiacetic acid, 1,4-dihydro-2-methylbenzoic acid, 1,4-dihydroxy-2-naphthoic acid, 10-hydroxydecanoic acid, 10-undecynoic acid, 1-admantanecarboxylic acid, 1-cyano-1-cyclopropane-carboxylic acid, 1-hydroxy-2-naphthoic acid, 1-isoquinolinecarboxylic acid, 1-methyl-(1S,2R)-(+)-cis-1,2,3,6-tetrahydrophthalate, 1-methyl-1-cyclohexanecarboxylic acid, 1-methyl-1H-indole-2-carboxylic acid, 1-methyl-2-pyrrolecarboxylic acid, 1-methylcyclopropanecarboxylic acid, 1-naphthoic acid, 1-phenyl-1-cyclopentanecarboxylic acid, 1-phenyl-1-cyclopropane-carboxylic acid, 1-pyreneacetic acid, 1-pyrenebutyric acid, 1-pyrenecarboxylic acid, 2-((1R,2R,3R,4S)-3-hydroxy-4,7,7-trimethylbicyclo[2.2.1]heptan-2-yl)acetic acid, 2-((benzyloxycarbonyl)(methyl)amino)-2-methylpropanoic acid, 2-(2,(trifluoromethyl)phenyl)acetic acid, 2-(2,4,5-trichlorophenoxy)-propionic acid, 2-(2,4-dichlorophenoxy)-propionic acid, 2-(3,5-dinitrobenzamido)-2-phenyl acetic acid, 2-(3,5-dinitrobenzamido)-4-methylpentanoic acid, 2-(3-chlorophenoxy)propionic acid, 2-(4-(trifluoromethyl)phenyl)acetic acid, 2-(4-chloro-3-nitrobenzoyl)-benzoic acid, 2-(4-chlorophenoxy)-2-methyl-propionic acid, 2-(4-chlorophenoxy) propionic acid, 2-(4-fluorobenzoyl)benzoic acid, 2-(4-hydroxy-3-methoxyphenyl)acetic acid, 2-(4-hydroxyphenoxy)-propionic acid, 2-(4-isobutylphenyl) propanoic acid, 2-(4-nitrophenyl)propionic acid, 2-(benzyloxycarbonylamino)-3-(1H-indol-3-yl)propanoic acid, 2-(trifluoromethyl)acrylic acid, 2-(trifluoromethyl)benzoic acid, 2-(trifluoromethyl)cinnamic acid, 2,2,3,3-tetramethyl-cyclopropanecarboxylic acid, 2,2-bis(hydroxymethyl)-propionic acid, 2,3,4,5,6-pentafluoro-cinnamic acid, 2,3,4,5,6-pentafluorophenoxy acetic acid, 2,3,4,5,6-pentafluorophenyl-acetic acid, 2,3,4,5-tetrafluorobenzoic acid, 2,3,4-trifluorocinnamic acid, 2,3,4-trihydroxybenzoic acid, 2,3,4-trimethoxybenzoic acid, 2,3,5,6-tetrafluoro-4-hydroxy-benzoic acid hydrate, 2,3,5,6-tetrafluorobenzoic acid, 2,3,5,6-tetrafluoro-p-toluic acid, 2,3,5-triiodobenzoic acid, 2,3,6-trifluorobenzoic acid, 2,3-dichlorobenzoic acid, 2,3-difluorobenzoic acid, 2,3-dihydroxybenzoic acid, 2,3-dimethylbenzoic acid, 2,4,5-trichlorophenoxyacetic acid, 2,4,5-trimethoxybenzoic acid, 2,4,6-trichlorobenzoic acid, 2,4,6-trifluorobenzoic acid, 2,4,6-trihydroxybenzoic acid monohydrate, 2,4,6-trimethylbenzoic acid, 2,4-bis(trifluoromethyl)-benzoic acid, 2,4-dichloro-5-fluorobenzoic acid, 2,4-dichloro-5-sulfamoyl-benzoic acid, 2,4-dichlorobenzoic acid, 2,4-dichlorophenylacetic acid, 2,4-difluorobenzoic acid, 2,4-difluorophenylacetic acid, 2,4-dihydroxybenzoic acid, 2,4-dimethylbenzoic acid, 2,4-dinitrobenzoic acid, 2,4-dinitrophenylacetic acid, 2,4-hexadienoic acid, 2,5-bis(trifluoromethyl)-benzoic acid, 2,5-dichlorobenzoic acid, 2,5-difluorobenzoic acid, 2,5-difluorophenylacetic acid, 2,5-dihydroxybenzoic acid, 2,5-dihydroxyphenylacetic acid, 2,5-dimethoxybenzoic acid, 2,5-dimethoxycinnamic acid, 2,6-dichloro-3-nitrobenzoic acid, 2,6-difluorobenzoic acid, 2,6-difluorophenylacetic acid, 2,6-dihydroxybenzoic acid, 2,6-dimethoxynicotinic acid, 2,6-dimethylbenzoic acid, 2,6-heptadienoic acid, 2-[4-(dibutylamino)-2-hydroxy-benzoyl]benzoic acid, 2-bibenzylcarboxylic acid, 2-biphenyl carboxylic acid, 2-bromo-3-nitrobenzoic acid, 2-bromo-4,5-dimethoxybenzoic acid, 2-bromo-5-methoxybenzoic acid, 2-bromo-5-nitrobenzoic acid, 2-bromoacrylic acid, 2-bromophenylacetic acid, 2-chloro-3-nitrobenzoic acid, 2-chloro-4,5-difluorobenzoic acid, 2-chloro-4-fluorobenzoic acid, 2-chloro-5-(methylthio)-benzoic acid, 2-chloro-5-(trifluoro-methyl)benzoic acid, 2-chloro-5-nitrobenzoic acid, 2-chloro-5-nitrocinnamic acid, 2-chloro-6-fluorobenzoic acid, 2-chloro-6-fluorophenylacetic acid, 2-chloro-6-methylnicotinic acid, 2-chlorobenzoic acid, 2-chloronicotinic acid, 2-chlorophenylacetic acid, 2-chloropropionic acid, 2-ethoxy-1-naphthoic acid, 2-ethoxybenzoic acid, 2-ethyl-2-hydroxybutyric acid, 2-ethylbutyric acid, 2-ethylhexanoic acid, 2-ethylthio-2,2-diphenyl-acetic acid, 2-fluoro-3-(trifluoromethyl)-benzoic acid, 2-fluoro-4-(trifluoromethyl)-benzoic acid, 2-fluoro-5-methylbenzoic acid, 2-fluoro-5-nitrobenzoic acid, 2-fluoro-6-(trifluoromethyl)-benzoic acid, 2-fluorobenzoic acid, 2-fluorocinnamic acid, 2-fluorophenylacetic acid, 2-hydroxy-3-isopropyl-6-methylbenzoic acid, 2-hydroxy-3-isopropylbenzoic acid, 2-hydroxy-3-methylbutyric acid, 2-hydroxy-6-isopropyl-3-methylbenzoic acid, 2-hydroxycaproic acid, 2-hydroxyhippuric acid, 2-hydroxyisobutyric acid, 2-hydroxyisobutyric acid, 2-hydroxynicotinic acid, 2-hydroxyphenylacetic acid, 2-iodobenzoic acid, 2-mercaptonicotinic acid, 2-methoxy-2-phenylacetic acid, 2-methoxy-4-(methylthio)-benzoic acid, 2-methoxy-4-nitrobenzoic acid, 2-methoxyphenylacetic acid, 2-methyl-1-cyclohexane-carboxylic acid (cis and trans), 2-methyl-3-nitrobenzoic acid, 2-methyl-3-phenylpropanoic acid, 2-methyl-4-oxo-4-phenylbutyric acid, 2-methyl-6-nitrobenzoic acid, 2-methylbutyric acid, 2-methylcinnamic acid, 2-methylcyclopropane-carboxylic acid (cis&trans), 2-methylhexanoic acid, 2-methylhippuric acid, 2-methylhydrocinnamic acid, 2-methylvaleric acid, 2-naphthoic acid, 2-naphthylacetic acid, 2-nitro-4-(trifluoromethyl)benzoic acid, 2-nitrobenzoic acid, 2-norbornaneacetic acid, 2-oxo-6-pentyl-2H-pyran-3-carboxylic acid, 2-phenoxybenzoic acid, 2-phenoxybutyric acid, 2-phenoxypropionic acid, 2-propylpentanoic acid, 2-quinoxalinecarboxylic acid, 2-thiopheneacetic acid, 2-thiopheneacetic acid, 2-thiopheneglyoxylic acid, 3-(2-hydroxyphenyl)propionic acid, 3-(2-thienyl)acrylic acid, 3-(3,4,5-trimethoxyphenyl)-propionic acid, 3-(3,4-dimethoxyphenyl)-propionic acid, 3-(3-hydroxy-2,4,6-triiodophenyl)pentanoic acid, 3-(3-hydroxyphenyl)-propionic acid, 3-(3-methoxyphenyl)propionic acid, 3-(4-chlorobenzoyl)propionic acid, 3-(4-chlorobenzoyl)propionic acid, 3-(4-chlorobenzoyl)propionic acid, 3-(4-fluorobenzoyl)propionic acid, 3-(4-hydroxyphenyl)propionic acid, 3-(phenyl sulfonyl)propionic acid, 3-(trifluoromethyl)cinnamic acid, 3-(trimethyl silyl)propynoic acid, 3,3,3-triphenylpropionic acid, 3,4-(methylenedioxy)cinnamic acid, 3,4-(methylenedioxy)phenyl-acetic acid, 3,4-dichlorobenzoic acid, 3,4-dichlorophenoxyacetic acid, 3,4-diethoxybenzoic acid, 3,4-difluorobenzoic acid, 3,4-dihydroxybenzoic acid, 3,4-dihydroxyhydrocinnamic acid, 3,4-dihydroxyphenylacetic acid, 3,5,6-trichlorosalicylic acid, 3,5-bis(trifluoromethyl)-phenyl acetic acid, 3,5-dibromobenzoic acid, 3,5-dichlorosalicyclic acid, 3,5-difluorocinnamic acid, 3,5-dihydroxy-2-naphthoic acid, 3,5-dinitrobenzoic acid, 3,5-dinitro-o-tuluic acid, 3,5-dinitro-p-toluic acid, 3,5-dinitrosalicyclic acid, 3,5-di-tert-butyl-4-hydroxy-benzoic acid, 3,5-di-tert-butylbenzoic acid, 3,7-dihydroxy-2-naphthoic acid, 3,thiopheneacetic acid, 3-benzoyl-2-pyridinecarboxylic acid, 3-benzoylbenzoic acid, 3-bromo-4-fluorobenzoic acid (95%), 3-bromo-4-methylbenzoic acid, 3-bromo-5-iodobenzoic acid, 3-bromobenzoic acid, 3-bromocinnamic acid, 3-carboxy-PROXYL, 3-chloro-2-nitrobenzoic acid, 3-chloro-4-fluorobenzoic acid, 3-chloro-4-hydroxyphenyl-acetic acid, 3-chlorosalicylic acid, 3-cyanobenzoic acid, 3-fluoro-2-methylbenzoic acid, 3-fluoro-4-hydroxy-phenylacetic acid, 3-fluoro-4-methoxybenzoic acid, 3-fluorophenylacetic acid, 3-furoic acid, 3-hydroxy-2-naphthoic acid, 3-hydroxy-2-quinoxaline-carboxylic acid, 3-hydroxy-4-methoxybenxoic acid, 3-hydroxy-4-methoxy-cinnamic acid, 3-hydroxy-4-nitrobenzoic acid, 3-hydroxybenzoic acid, 3-hydroxybutyric acid, 3-hydroxyphenylacetic acid, 3-indolebutyric acid, 3-indoleglyoxylic acid, 3-indolepropionic acid, 3-iodo-4-methylbenzoic acid, 3-iodobenzoic acid, 3-isoquinolinecarboxylic acid hydrate, 3-methoxy-4-nitrobenzoic acid, 3-methoxycyclohexane-carboxylic acid (cis&trans), 3-methyl-2-phenyvaleric acid, 3-methylhippuric acid, 3-methylindene-2-carboxylic acid, 3-methylsalicylic acid, 3-methylvaleric acid, 3-nitreobenzoic acid, 3-nitrophenylacetic acid, 3-nitropropionic acid, 3-noradamantanecarboxylic acid, 3-oxo-1-indancarboxylic acid, 3-phenoxybenzoic acid, 3-phenylbutyric acid, 3-p-tolylpropanoic acid, 3-thiophenecarboxylic acid, 4-(1,3-dioxoisoindolin-2-yl)-2-hydroxybutanoic acid, 4-(2,4,5-trichlorophenoxy)-butyric acid, 4-(2,4-dichlorophenoxy)-butyric acid, 4-(2,4-di-tert-pentylphenoxy)butyric acid, 4-(2-phenoxyethoxy)benzoic acid, 4-(3,4-dimethoxyphenyl)-butyric acid, 4-(4-methoxyphenyl)butyric acid, 4-(4-nitrophenyl)butyric acid, 4-(diethylamino)benzoic acid, 4-(dimethylamino)cinnamic acid, 4-(dimethylamino)phenyl-acetic acid, 4-(ethylthio)benzoic acid, 4-(hydroxymethyl)benzoic acid, 4-(methyl sulfonyl)benzoic acid, 4-(methylthio)benzoic acid, 4-(methylthio)phenylacetic acid, 4-(trifluoromethoxy)benzoic acid, 4'-(trifluoromethyl)biphenyl-2-carboxylic acid, 4-(trifluoromethyl)mandelic acid, 4,4,4-trifluoro-3-methyl-2-butenoic acid, 4,4-bis(4-hydroxyphenyl)-valeric acid, 4,5-dimethoxy-2-nitrobenzoic acid, 4,6-dioxoheptanoic acid, 4-[4-(2-carboxybenzoyl)-phenyl]butyric acid, 4-acetamidobenzoic acid, 4-acetylbenzoic acid, 4-acetylphenoxyacetic acid, 4-benzyloxy-3-methoxyphenyl-acetic acid, 4-biphenylacetic acid, 4-bromo-3,5-dihydroxy-benzoic acid, 4-bromobenzoic acid, 4-bromocinnamic acid, 4-bromophenylacetic acid, 4-butoxybenzoic acid, 4-butoxyphenylacetic acid, 4-butylbenzoic acid, 4-chloro-2,5-difluorobenzic acid, 4-chloro-3-sulfamoylbenzoic acid, 4-chlorobenzoic acid, 4-chloro-o-tolyloxyacetic acid, 4-chlorophenylacetic acid, 4-chlorosalicylic acid, 4-ethoxycarbonyloxy-3,5-dimethoxybenzoic acid, 4-ethoxyphenylacetic acid, 4-ethylbenzoic acid, 4'-ethylbiphenyl-4-carboxylic acid, 4-fluorenecarboxylic acid, 4-fluoro-1-naphthoic acid, 4-fluoro-2-(trifluoromethyl)-benzoic acid, 4-fluoro-3-nitrobenzoic acid, 4-fluorobenzoic acid, 4-fluorobenzoic acid, 4-fluorocinnamic acid, 4-fluorophenoxyacetic acid, 4-heptyloxybenzoic acid, 4-hexylbenzoic acid, 4-hexyloxybenzoic acid, 4-hydroxy-3-(morpholino-methyl)benzoic acid hydrate, 4-hydroxy-3,5-dinitrobenzoic acid, 4-hydroxy-3-methoxybenzoic acid, 4-hydroxy-3-methoxy-mandelic acid, 4-hydroxy-3-nitrobenzoic acid, 4-hydroxy-3-nitrophenylacetic acid, 4-hydroxybenzoic acid, 4'-hydroxybiphenyl-4-carboxylic acid, 4-hydroxyphenylacetic acid, 4-hydroxyphenylacetic acid, 4-hydroxyphenylpyruvic acid, 4-iodobenzoic acid, 4-isopropoxybenzoic acid, 4-methoxy-3-nitrobenzoic acid, 4-methoxycyclohexane-carboxylic acid, 4-methoxysalilcylic acid, 4-methyl-1-cyclohexane-carboxylic acid (cis and trans), 4-methyl-3-nitrobenzoic acid, 4-methylhippuric acid, 4-methylsalicyclic acid, 4-methylvaleric acid, 4-nitro-3-pyrazolecarboxylic acid, 4-nitrohippuric acid, 4-nonyloxybenzoic acid, 4-Octylbenoic acid, 4-oxo-4H-1-benzopyran-2-carboxylic acid, 4-oxo-6-phenyl-5-hexenoic acid, 4-pentenoic acid, 4-pentylbenzoic acid, 4-pentylbicyclo[2.2.2]octane-1-carboxylic acid, 4-pentyloxybenzoic acid, 4-pentynoic acid, 4-phenylbutyric acid, 4-Propoxybenzoic acid, 4-propylbenzoic acid, 4-pyrazolecarboxylic acid, 4-tert-butylbenzoic acid, 4-tert-butylcyclohexanecarboxylic acid, 4-Vinylbenzoic acid, 5-(4-chlorophenyl)-2-furoic acid, 5,6-dichloronicotinic acid, 5-bromo-2,4-dihydroxybenzoic acid, 5-fluoro-2-methylbenzoic acid, 5-fluoroindole-2-carboxylic acid, 5-fluorosalicylic acid, 5-hydantoinacetic acid, 5-hydroxy-2-indole-carboxylic acid, 5-methoxy-1-indanone-3-acetic acid, 5-methoxy-2-methyl-3-indoleacetic acid, 5-methoxy-2-nitrobenzoic acid, 5-methoxysalicylic acid, 5-methyl-2-nitrobenzoic acid, 5-methyl-2-pyrazinecarboxylic acid, 5-nitro-2-furoic acid, 5-nitro-3-pyrazolecarboxylic acid, 5-phenylvaleric acid, 6-(carbobenzyloxyamino)-caproic acid, 6-acetamidohexnoic acid, 6-bromohexanoic acid, 6-chloronicotinic acid, 6-hydroxy-2,5,7,8-tetramethylchroman-2-carboxylic acid, 6-methylchromone-2-carboxylic acid, 6-methylnicotinic acid, 6-nitrocaproic acid, 6-oxoheptaoic acid, 6-phenylhexanoic acid, 7-(carboxymethyoxy)-4-methylcoumarin, 7-hydroxycoumarin-4-acetic acid, 7-methoxy-2-benzofuran-carboxylic acid, 7-methoxycoumarin-4-acetic acid, 7-oxoctanoic acid, 9-anthracenecarboxylic acid, 9-fluoreneacetic acid, 9-fluorenone-1-carboxylic acid, A,a,a-trifluoro-m-toluic acid, a-acetamidocinnamic acid, abietic acid, acetic acid, acetic acid, acetic acid, acetyl-L-asparagine, acetylsalicyclic acid, acetylsalicylic acid, a-cyano-4-hydroxycinnamic acid, adipic acid monoethyl ester, a-hydroxyhippuric acid, anthranilic acid, anti-3-oxotricyclo[2.2.1.02,6]heptane-7-carboxylic acid, a-phenylcyclopentaneacetic acid, a-phenyl-o-toluic acid, Atrolactic acid, benzilic acid, benzotriazole-5-carboxylic acid, benzoylformic acid, bis(4-chlorophenyl)acetic acid, carbobenzyloxy-DL-alanine, carbobenzyloxy-L-alanine, carbobenzyloxy-1-glutamine, carbobenzyloxy-L- valine, cis-2-methoxycinnamic acid, Crotonic acid, cyclohexanebutyric acid, cyclohexanecarboxylic acid, cyclohexanepentanoic acid, cyclohexanepropionic acid, cyclopentylacetic acid, D,L-3,4-dihydroxymandelic acid, D-3-phenyllactic acid, decanoic acid, dicyclohexylacetic acid, diethylphosphonoacetic acid, dikegulac hydrate, diphenylacetic acid, fumaric acid monoethyl ester, fusaric acid, gallic acid, geranic acid, glycolic acid, heptadecafluorononanoic acid, heptanoic acid, hexanoic acid, hippuric acid, hydrocinnamic acid, indole-3-carboxylic acid, indole-4-carboxylic acid, isovaleric acid, L-3-phenyllactic acid, Lauric acid, L-Lactic acid (85%), maleamic acid, methoxyacetic acid, mono-(1R)-(−)-menthyl phthalate, mono-(1S)-(+)-menthyl phthalate, mono-methyl cis-5-norbornene-endo-2,3-dicarboxylate, mono-methyl phthalate, mono-methylterephthalate, N-(2-furoyl)glycine, n-(3,5-dinitrobenzoyl)-DL-a-phenylglycine, N-(3-indolylacetyl)-L-alanine, N-(3-indolylacetyl)-L-isoleucine, N-(3-indolylacetyl)-L-leucine, N-(3-indolylacetyl)-L-phenylalanine, N-(3-indolylacetyl)-L-valine, N-(carbobenzyloxy)-1-phenyl-alanine, N,N-diethyl-3,6-difluoro-phthalamic acid, N—[(R)-1-(1-naphthyl)ethyl]-phthalamic acid, N-[5-(trifluoromethyl)-2-pyridyl]-L-valine, n-acetyl-4-fluoro-DL-phenylalanine, N-acetyl-DL-tryptophan, n-acetyl-1-leucine, N-acetyl-L-methionine, N-acetyl-L-phenylalanine, N-acetyl-L-phenylalanine, n-acetyl-1-tyrosine, N-benzoyl-(2R,3 S)-3-phenyl-isoserine, N-benzoyl-L-threonine, N-carbobenzyloxy-2-methyl-alanine, N-carbobenzyloxy-L-glutamic acid 1-methyl ester, N-carbobenzyloxy-L-isoleucine, N-carbobenzyloxy-L-Leucine, n-carbobenzyloxy-1-threonine, n-ethoxycarbonyl-1-phenylalanine, nonanoic acid, N-p-tosylglycine, N-p-tosyl-L-phenylalanine, o-anisic acid, p-anisic acid, pentafluorobenzoic acid, phenoxyacetic acid, phenylacetic acid, podocarpic acid, pyruvic acid, rhodanine-3-acetic acid, S-(thiobenzoyl) thioglycolic acid, s-benzyl-n-carbobenzyloxy-1-cysteine, Sebacic acid monomethyl ester, succinamic acid, succinic 2,2-dimethyl-hydrazide, tetrahydro-2-furoic acid, trans-1-acetyl-4-hydroxy-L-proline, trans-2,3-dimethoxycinnamic acid, trans-2,4-dichlorocinnamic acid, trans-2,4-difluorocinnamic acid, trans-2,5-difluorocinnamic acid, trans-2,6-difluorocinnamic acid, trans-2-chloro-6-fluro-cinnamic acid, trans-2-hexenoic acid, trans-3-(2,3,5,6-tetramethyl-benzoyl) acrylic acid, trans-3-(2,5-dimethylbenzo-yl)-acrylic acid, trans-3-(4-ethoxy-benzoyl)acrylic acid, trans-3-(4-methoxy-benzoyl)-acrylic acid, trans-3-(4-methylbenzoyl)-acrylic acid, trans-3,4-difluorocinnamic acid, trans-3-fluorocinnamic acid, trans-3-furanacrylic acid, trans-3-hexenoic acid, trans-4-chloro-3-nitrocinnamic acid, trans-4-hydroxy-3-methoxy-cinnamic acid, trans-4-hydroxy-3-methoxy-cinnamic acid, trans-4-methyl-1-cyclohexa-ne carboxylic acid, trans-4-pentylcyclohexane carboxylic acid, trans-5-bromo-2-methoxy cinnamic acid, trans-Styrylacetic acid, trans-Styrylacetic acid, tridecafluoroheptanoic acid, trimethylacetic acid, triphenylacetic acid, Valeric acid, and Yohimbinic acid, mono-hydrate. In some embodiments $R^1$ or $R^2$ is

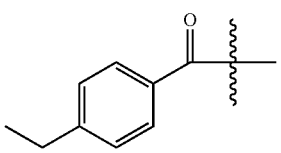 [SMILES: *C(=O)c1ccc(CC)cc1]

In still other embodiments $R^1$ or $R^2$ is

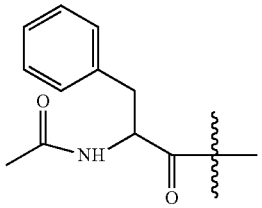 [SMILES: *C(=O)C(Cc1ccccc1)NC(C)=O]

In yet other embodiments $R^1$ or $R^2$ is

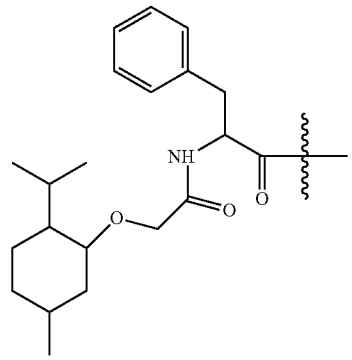 [SMILES: *C(=O)C(Cc1ccccc1)NC(=O)COC1CC(C)CCC1C(C)C]

In some embodiments the compound is of the, of the formula

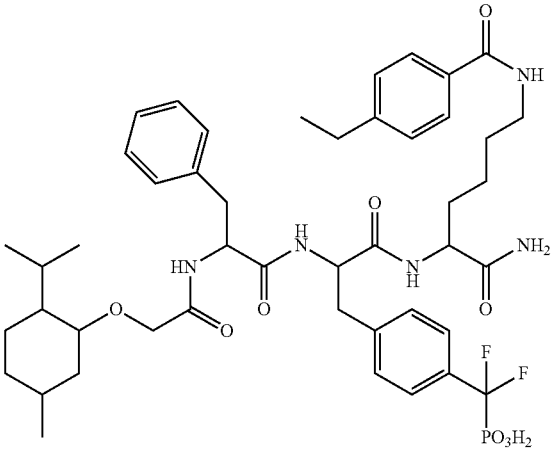

and pharmaceutically acceptable salts thereof, still other embodiments include a pharmaceutical formulation comprising at least one of the inventive compounds and a pharmaceutical acceptable carrier therefore.

Still other embodiment include methods of treating an individual with a physiological disease, disorder, or condition associated with inappropriate activity or pathological activity of a protein tyrosine phosphatase comprising the step of administering to the individual a compound of claim 1 in a therapeutically effective amount. In some embodiment the disease, disorder, or condition is selected from the group consisting: of type 1 diabetes, type 2 diabetes, obesity, metabolic syndrome, Crohn's disease, rheumatoid arthritis, Graves' disease, systemic lupus erythematosus, leukemia, and tuberculosis. In some embodiments the PTP inhibitor is a selective TC-PTP inhibitor still other embodiments included the inventive compounds in the pharmaceutically acceptable carrier thereof.

Other embodiments include methods for constructing and screening for a compound that selectively inhibits a target PTP isozyme relative to a comparative PTP isozyme, comprising the steps of: providing a compound which binds to the active site region of said target PTP isozyme; supplying at least one additional peripheral moiety to said compound which binds to a region of the target PTP isozyme adjacent to or at least near to the active site; covalently bonding a fluorescein group to said compound; separately exposing said compound to the target PTP isozyme and comparative PTP isozyme; and measuring anisotropy values in a fluorescence polarization assay.

In some embodiments the screening method includes the target PTP isozyme is selected from the group consisting of a classical PTP, a dual specificity PTP, and a low molecular weight PTP. In still other embodiments the target or comparative PTP isozyme is selected from the group consisting of RPTPα, RPTPβ, CD45, LCA, RPTPδ, RPTPε, RPTPγ, LAR, SAP1, DEP1, CD148, RPTPη, RPTPκ, RPTPμ, IA-2, PTPRP, RPTPπ, IA-2β, phogrin, GLEPP1/PTP-U2/PTPROτ, PTPS31, PTP-SL, PCPTP, PTPBR7, PC12-PTP1, RPTPα, RPTPρ, PTPJ/PTP-U1/PTPRomicron, OST-PTP, RPTξ, PTP1B, TCPTP, MPTP, PTP-S, PTPH1, PTP-MEG1, TEP, STEP, SHP1, PTP1C, SH-PTP1, HCP, HePTP, LCPTP, PTP-MEG2, SHP2, SH-PTP2, Syp, PTP1D, PTP2C, SH-PTP3, PTP-PEST, PTP-P19, PTPG1, PTP-BAS, FAP-1, PTP1E, RIP, PTPL1, PTP-BL, PTP36, PEZ, PTPD2, PTP-HSCF, PTP20, BDP, TypPTP, PTPD1, PTP2E, PTP-RL10, LYP, PEP, HD-PTP, HDPTP, PTP-TD14, KIAA1471, and DKFZP564F0923. In some embodiments one or both of the target and comparative PTP isozymes are additionally exposed to a known competitive binding compound prior to the measuring step.

In some embodiments the target PTP isozyme is TC-PTP, the comparative PTP isozyme is PTP1B, the compound is F$_2$Pmp, the peripheral group is a residue of a carboxylic acid, and the known competitive compound is Fmoc-F$_2$Pmp-OH.

Still other embodiments include altering the activity of at least PTP enzyme by contacting a cell with at least one of the inventive compounds according to formula A. In some embodiments the cell is either a human or an animal cell. In some embodiments the cell is a CD4+ T-cells derived from a human. In some embodiments the compound preferentially reduces the activity of the tyrosine phosphatase TC-PTP.

Other embodiments re methods of treating a patient, comprising the steps of: identifying a patient having type 1 diabetes; providing a compound having the following formula

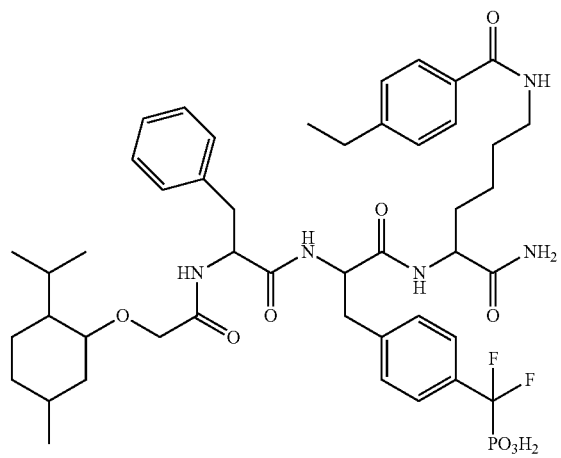

or a pharmaceutically acceptable salt thereof; and administering at least one therapeutically effective dose of said compound or a pharmaceutically acceptable salt thereof to the patient. In some embodiments the patient is a human.

In another embodiment, the compound is provided in a pharmaceutical formulation for medicinal application, which comprises a compound of the present invention or a pharmaceutically acceptable salt thereof, and a pharmaceutically acceptable carrier therefor.

The expression "pharmaceutically acceptable carrier" as used herein in relation to the carrier is used in the sense of being compatible with the compound or salt of the invention employed in the formulation and with any other therapeutic agent that may be present, and not being detrimental to the recipient thereof. The carrier itself may constitute one or more excipients conventionally used in the art of pharmacy that enable the compound or salt of the present invention and any other therapeutic agent that may be present, to be formulated as a pharmaceutical formulation.

The pharmaceutical formulations of the present invention include those suitable for oral, parenteral (including subcutaneous, intradermal, intramuscular and intravenous) and rectal administration. The formulations may be presented in unit dosage form and may be prepared by any of the methods well known in the art of pharmacy. All methods include the step of bringing into association the active ingredient, i.e., the compound or salt of the present invention, with the carrier. In general, the formulations are prepared by uniformly and intimately bringing into association the active ingredient with a liquid carrier or, a finely divided solid carrier or both, and then, if necessary, forming the associated mixture into the desired formulation.

The pharmaceutical formulations of the present invention suitable for oral administration may be presented as discrete units, such as a capsule, cachet, tablet, or lozenge, each containing a predetermined amount of the active ingredient; as a powder or granules; as a solution or a suspension in an aqueous liquid or a non-aqueous liquid such as a syrup, elixir or a draught, or as an oil-in-water liquid emulsion or a water-in-oil liquid emulsion. The formulation may also be a bolus, electuary or paste.

A tablet may be made by compressing or molding the active ingredient with the pharmaceutically acceptable carrier. Compressed tablets may be prepared by compressing in a suitable machine the active ingredient in a free-flowing form, such as a powder or granules, in admixture with, for example, a binding agent, an inert diluent, a lubricating agent, a disintegrating agent and-/or a surface active agent. Molded tablets may be prepared by molding in a suitable machine a mixture of the powdered active ingredient moistened with an inert liquid diluent. The tablets may optionally be coated or scored and may be formulated so as to provide slow or controlled release of the active ingredient.

The pharmaceutical formulations of the present invention suitable for parenteral administration include aqueous and non-aqueous sterile injection solutions, and may also include an antioxidant, buffer, a bacteriostat and a solution which renders the composition isotonic with the blood of the recipient, and aqueous and non-aqueous sterile suspensions which may contain, for example, a suspending agent and a thickening agent. The formulations may be presented in single unit-dose or multi-dose containers, and may be stored in a lyophilized condition requiring the addition of a sterile liquid carrier prior to use.

As used herein, the term "pharmaceutically acceptable salt" is defined as a salt wherein the desired biological activity of the PTP inhibitor is maintained and which exhibits a minimum of undesired toxicological effects. Non-limiting examples of such a salt are (a) acid addition salts formed with inorganic acids (e.g., hydrochloric acid, hydrobromic acid, sulphuric acid, phosphoric acid, nitric acid, and the like), and salts formed with organic acids (such as e.g. acetic acid, oxalic acid, tartaric acid, succinic acid, malic acid, ascorbic acid, benzoic acid, tannic acid, palmitic acid, polyglutamic acid, naphthalene sulphonic acid, naphthalene disulphonic acid, polygalacturonic acid and the like); (b) base addition salts formed with metal cations such as zinc, calcium, bismuth, barium, magnesium, aluminium, copper, cobalt, nickel, cadmium, sodium, potassium and the like, or with a cation formed from ammonia, N,N-dibenzylethylenediamine, D-glucosamine, tetraethylammonium or ethylenediamine; or (c) combinations of (a) and (b); e.g. a zinc tannate or the like.

As used herein, "inhibition" or "inhibitory activity" each encompass whole or partial reduction of activity or effect of an enzyme.

A "therapeutically effective amount" in general means the amount that, when administered to a subject or animal for treating a disease, is sufficient to affect the desired degree of treatment for the disease. Effective amounts of a compound of this invention or composition thereof for treatment of a mammalian subject are about 0.1 to about 1000 mg/Kg of body weight of the subject/day, such as from about 1 to about 100 mg/Kg/day, especially from about 10 to about 100 mg/Kg/day.

A "selective" PTP inhibitor is one that has at least 2, 5, 10, 20, 50, 100, or 200 fold greater inhibitory activity (for example, as determined by calculation of $IC_{50}$, $K_i$, or other measure of affinity or effect) for a particular isozyme of PTP compared to other members of the PTP enzyme family. For example, a selective TC-PTP inhibitor is a compound that has at least 2, 5, 10, 20, 50, or 100 fold greater activity (determined by calculation of Ki) at TC-PTP compared to PTP1B.

The term "associated with inappropriate activity of a protein tyrosine phosphatase" encompasses all diseases, disorders, or conditions in which symptoms are in part related to excessive activity of a protein tyrosine phosphatase or deficient activity of a protein tyrosine kinase.

PTPs control a broad spectrum of cellular processes. Dysfunction of particular PTPs is associated with particular disorders and diseases. For example, mice lacking PTP1B are highly refractory to Type 2 diabetes and obesity (Elchebly et al., 1999; Klaman et al., 2000). TC-PTP is a PTP that shares 74% sequence identity with PTP1B in its catalytic domain (Bourdeau et al., 2005). Although originally cloned from a T cell cDNA library, TC-PTP is ubiquitously expressed in other tissues. Studies with TC-PTP-deficient mice implicate a role for TC-PTP in hematopoiesis and cytokine response (Youten et al., 1997). Accordingly, TC-PTP can modulate cytokine signaling through the Jak/Stat pathways (Simoncic et al., 2002; Bourdeau et al., 2005). Polymorphisms in the gene (ptpn2) encoding TC-PTP have been linked to the development of several inflammatory disorders including type 1 diabetes, Crohn's disease, and rheumatoid arthritis (WTCCC, 2007; Todd et al., 2007). In addition, several signal molecules, including epidermal growth factor (EGF) receptor (Tiganis et al., 1998; Klingler-Hoffmann et al., 2001; Mattila et al., 2005), the insulin receptor (Galic et al., 2003), Src kinase (van Vliet et al., 2005), and the adaptor protein p52Shc (Tiganis et al., 1998) have also been suggested as TC-PTP substrates.

Achieving specificity for PTP inhibition is difficult, in part because the target is a member of a large protein family. PTPs have been classified into sub-families: classical PTPs, dual specificity PTPS, and low molecular weight PTPs. Examples of classical PTPs include RPTPγ, RPTPβ, CD45, LCA, RPTPδ, RPTPε, RPTPγ, LAR, SAP1, DEP1, CD148, RPTPη, RPTPκ, RPTPμ, IA-2, PTPRP, RPTPπ, IA-2β, phogrin, GLEPP1/PTP-U2/PTPROτ, PTPS31, PTP-SL, PCPTP, PTPBR7, PC12-PTP1, RPTPσ, RPTPρ, PTPJ/PTP-U1/PTPRomicron, OST-PTP, RPTξ, PTP1B, TCPTP, MPTP, PTP-S, PTPH1, PTP-MEG1, TEP, STEP, SHP1, PTP1C, SH-PTP1, HCP, HePTP, LCPTP, PTP-MEG2, SHP2, SH-PTP2, Syp, PTP1D, PTP2C, SH-PTP3, PTP-PEST, PTP-P19, PTPG1, PTP-BAS, FAP-1, PTP1E, RIP, PTPL1, PTP-BL, PTP36, PEZ, PTPD2, PTP-HSCF, PTP20, BDP, TypPTP, PTPD1, PTP2E, PTP-RL10, LYP, PEP, HD-PTP, HDPTP, PTP-TD14, KIAA1471, and DKFZP564F0923. The common architecture of the PTP active site (i.e. pTyr-binding pocket) has impeded the development of selective PTP inhibitors. However, pTyr alone is not sufficient for high-affinity binding and residues flanking pTyr are important for PTP substrate recognition (Zhang, 2002). Thus, unique PTP sub-pockets that border the active site have been targeted to enhance inhibitor potency and selectivity. In principle, active site-directed, potent and selective PTP inhibitors can be devised by tethering a nonhydrolyzable pTyr mimetic to appropriately functionalized moieties to engage both the active site and unique nearby sub-pockets. Phosphonodifluoromethyl phenylalanine ($F_2Pmp$) has been identified as a useful and effective pTyr surrogate (Burke et al., 1994; Chen et al., 1995). $F_2Pmp$, however, is not selective for particular PTPs. It is disclosed herein that molecular scaffolds attached to the pTyr surrogate render the inhibitors PTP isozyme-selective. In one illustrative embodiment, methods for acquiring PTP inhibitor compounds that are selective for TC-PTP are described herein.

FIG. 1. Combinatorial library approach to target both the PTP active site and binding pockets immediately N- and C-terminal to pTyr.

One process for the acquisition of TC-PTP inhibitors began with 1 ($F_2Pmp$-Lys, FIG. 1), which contains two amines that could be modified to introduce molecular diversity at both sides of the $F_2Pmp$ residue. Keeping the library to a reasonable size, 576 carboxylic acids were selected that vary by molecular weight, charge, polarity, hydrophobicity, sterics, etc. and therefore provide a reasonable (albeit limited) structural diversity to increase the number and strength of the noncovalent interactions between TC-PTP and the inhibitory compound. Using standard solid phase peptide synthesis methodology, two focused libraries were prepared in a stepwise fashion where the available $NH_2$ group was condensed with 576 carboxylic acids (FIG. 1). The libraries were directly screened for inhibitors of TC-PTP using a phosphatase activity-based assay. This effort failed to identify inhibitors with significant selectivity over PTP1B. The lack of success was likely caused by the inherent uncertainty in purity and variation in concentration of library components used in the activity-based screen, which requires knowledge of accurate concentration for all compounds in order to yield meaningful structure and activity data ($IC_{50}$ values) to guide the development of inhibitors that could discriminate among closely related enzymes.

To overcome variation in library concentration introduced during synthesis, an alternative concentration independent screening strategy was developed that would enable facile assessment PTP inhibitory activity of combinatorial libraries efficiently assembled in situ. To this end, each member of the library was tagged with a fluorescein group at a position distal to the F₂Pmp moiety. The fluorescently labeled library can be subjected to a homogeneous, high-throughput fluorescence polarization (FP) displacement assay to identify high affinity active site binders to the PTPs (Zhang et al., 2007). A major advantage of the FP-based screen is that the strength of binding (increase in mA value) is independent of the concentration of the fluorophore when the fluorophore concentration is significantly lower than the protein concentration. Thus, the concentration independence of the FP assay allows one to obtain reliable structure and activity data (binding affinity) without the need for concentration uniformity for all library compounds.

A first generation library was focused on the interaction immediately C-terminal to F₂Pmp, using compound 5 as the precursor (Scheme I). The amine on F₂Pmp was capped with acetic acid, leaving the only free NH₂ group on the neighboring Lys ready for condensation with 576 carboxylic acids. The fluorescein tag was attached to the side chain of the Lys at the C-terminus of the tetra-peptide. An additional Ala was introduced between the two Lys residues in order to minimize interference from fluorescein to the interactions between TC-PTP and the F₂Pmp-Lys core. Compound 5 was synthesized using solid phase peptide synthesis with Fmoc chemistry and purified by HPLC.

introduced, in equal quantities, into individual wells of six 96-well plates, along with appropriate reagents to activate the acid functionality. A solution of 5 was then added to each well to initiate condensation. The reaction was quenched with cylcohexanamine, and the resulting library was diluted and dispensed into 384-well plates for FP-based screening.

To identify high-affinity active site-directed TC-PTP inhibitors, the fluorescein tagged library (~3 nM) was mixed with 2 µM TC-PTP, and the anisotropy values (measures of binding affinity) were recorded with a microplate reader both in the absence and presence of 500 µM Fmoc-F₂Pmp-OH, a known competitive ligand, which has an IC$_{50}$ of 20 µM for both TC-PTP and PTP1B. Fluorescently labeled compounds that are most resistant to displacement by Fmoc-F₂Pmp-OH should possess the highest affinity for TC-PTP. To identify inhibitors with preference to TC-PTP, the library was also counter screened against PTP1B, the closest relative of TC-PTP, under the same conditions. Compounds with the lowest displacement propensity and the largest differential in binding in favor of TC-PTP were identified. The structure and activity data revealed that compounds with p-substituted benzoic acids were preferentially selected by TC-PTP. The p-ethylbenzoic acid derivative surfaced as a Scheme I. First generation library synthesis and screening.

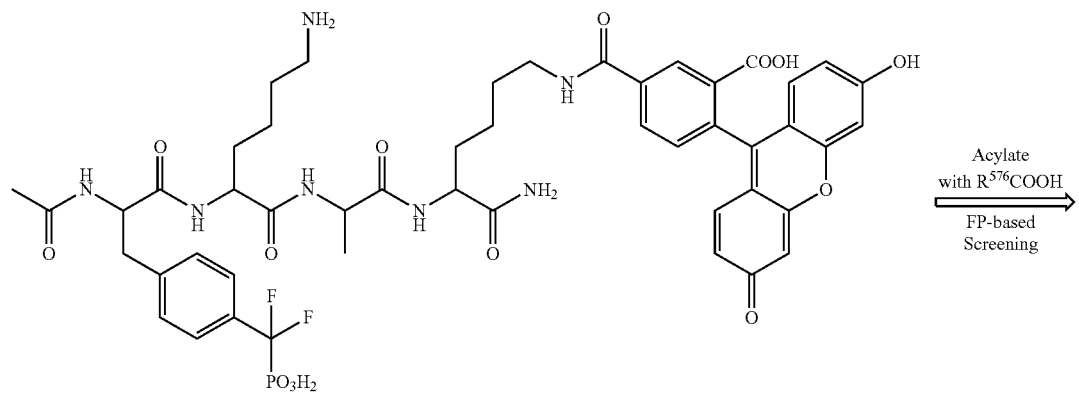

5

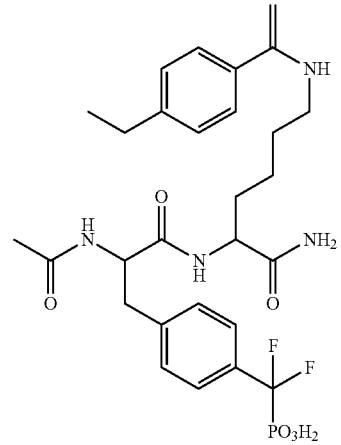

6

A 576-member library was constructed from 5 on a liquid handling workstation equipped with a 96-channel pipetting head. The 576 structurally diverse carboxylic acids were top hit and the lead compound 6 was synthesized, purified and characterized. As shown in Table 1, 6 inhibited TC-PTP-catalyzed reaction with an IC$_{50}$ of 160±20 nM, which is 12.5-fold lower than that of the parent compound 4. Moreover, 6 also showed a 4.4-fold selectivity over PTP1B.

TABLE 1

Inhibitory activity of hits identified from each library.

| Compound | Library | IC$_{50}$ or K$_i$ for TC-PTP (nM) | IC$_{50}$ or K$_i$ for PTP1B (nM) |
|---|---|---|---|
| 4 | 0 | 2,000 | 2,000 |
| 6 | 1 | 160 ± 20 | 700 ± 20 |
| 8 | 2 | 26 ± 2 | 87 ± 2 |
| 10 | 3 | K$_i$ = 4.1 ± 0.2 | K$_i$ = 23.1 ± 0.7 |

To build upon the lead generated from the first-generation library, the α-amino group from F$_2$Pmp in compound 7 (Scheme II) was condensed with the same set of 576 carboxylic acids to furnish a second-generation library of 576 different analogs of 6. Without being bound by theory, it is believed that introduction of diversity at the α-amino position of F$_2$Pmp maximizes interactions of inhibitors with sub-pockets N-terminal to the pTyr-binding site in the PTPs. The library was screened against both TC-PTP and PTP1B under similar conditions described above (~3 nM library components, 0.4 enzyme, and 1.5 mM competitive ligand Fmoc-F$_2$Pmp-OH). A number of hits were identified, which generally fell into two groups: aromatic amino acid derivatives and o-substituted benzoic acids. The hit with the highest affinity was resynthesized without the linker and the fluorescein tag to afford the lead compound 8. Interestingly, 8 displayed a 6.2-fold increase in affinity for TC-PTP (IC$_{50}$=26±2 nM) relative to 6, with no appreciable change in selectivity against PTP1B (Table 1).

Scheme II. Second generation library synthesis and screening.

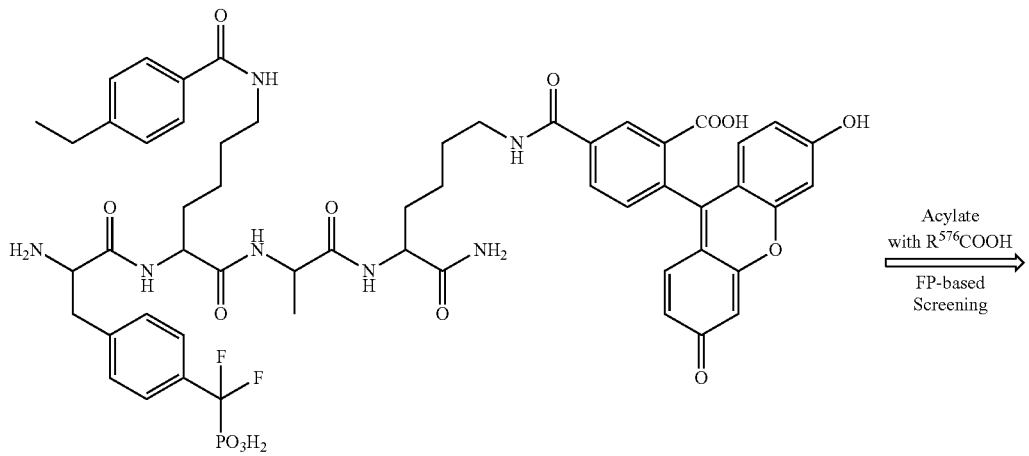

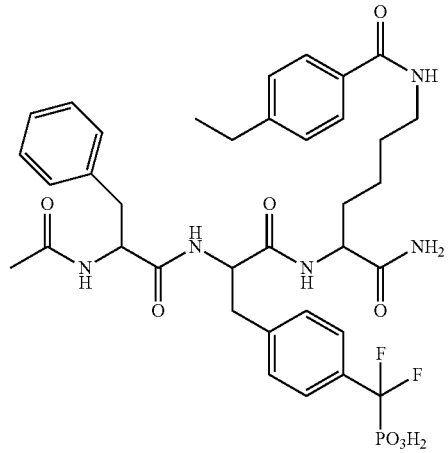

It was then investigated whether inhibitory potency and selectivity could be augmented further by replacing the acetyl group next to Phe in compound 8 with 576 carboxylic acids. Without being bound by theory, it is believed that replacement of the acetyl group with bulky functionalities enables the capture of additional interactions with nearby sub-pockets N-terminal to the pTyr-binding site in the PTPs. The third-generation library was prepared in a fashion analogous to those outlined above with precursor 9 (Scheme III), and the resulting fluorescein-tagged library (~3 nM) was screened at 0.5 enzyme in the absence and presence of 5 μM 8 as a competitor. The (+)-menthoxyacetic acid derivative 10 emerged as the most potent and selective TC-PTP inhibitor from the final library. Kinetic analysis indicated that 10 was a reversible and competitive inhibitor for both TC-PTP and PTP1B, with a $K_i$ of 4.1±0.2 nM and 23.1±0.7 nM, respectively (Table 1). Thus, compound 10 has a 5.6-fold selectivity for TC-PTP over its most close homologue PTP1B. Furthermore, compound 10 was more than 200-fold selective versus a panel of PTPs including the cytosolic PTPs, SHP2, Lyp, HePTP, PTP-Meg2, and FAP1, the receptor-like PTPs, CD45, LAR, and PTPα, the dual specificity phosphatase VHR, VHX, and CDC14A, and the low molecular weight PTP.

To determine the cellular efficacy of 10, its effect on tyrosine phosphorylation of EGFR, a known substrate of TC-PTP (Tiganis et al., 1998; Klingler-Hoffmann et al., 2001; Mattila et al., 2005) was assessed using an antibody against pTyr. The cells were incubated with 10 for 2 hr and subsequently treated either with or without EGF (2 ng/ml) for 10 min. Compound 10 augmented EGFR phosphorylation in a dose dependent manner (immunoblot for phosphorylated EGFR revealed progressively darker bands with increasing concentrations of compound 10 (0 nM<5 nM<10 nM<20 nM<50 nM). Total EGFR was probed as a loading control, and was similar across lanes. At 5 nM (1.2×$K_i$) concentration, compound 10 enhanced the phosphorylation level of EGFR by 1.9-fold compared to DMSO alone. More pronounced effects were observed at 10 and 20 nM (3.4- and 3.9-fold), respectively. These data contrast a general belief that phosphonate-based PTP inhibitors are incapable of penetrating the cell membrane. A structurally related but inactive analog of 10 (compound 11) lacking the difluoromethylenephosphonate moiety ($IC_{50}$>1 μM) had no effect on EGFR phosphorylation, even at 200 nM concentration, indicating that the cellular activity displayed by 10 is unlikely due to nonspecific effects.

Scheme III. Third generation library synthesis and screening.

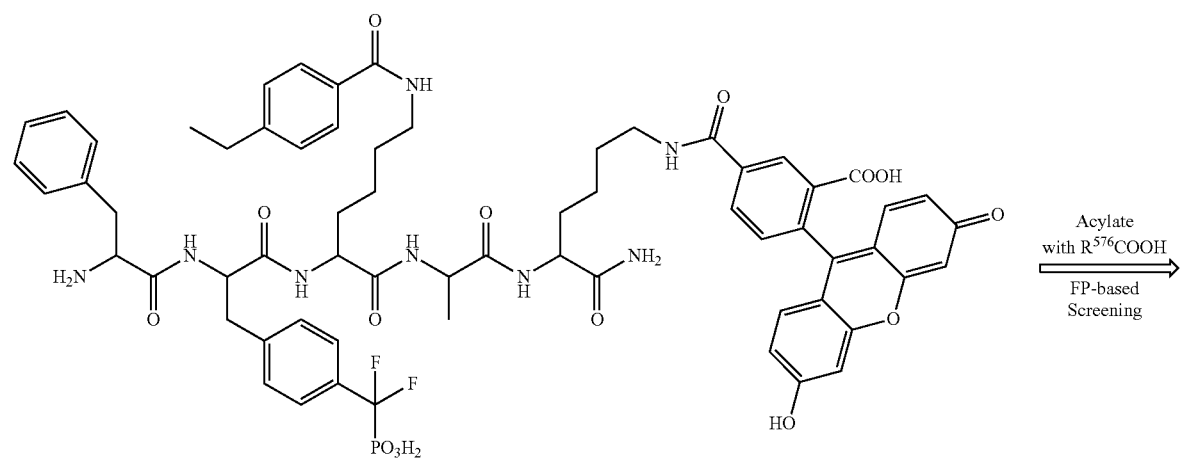

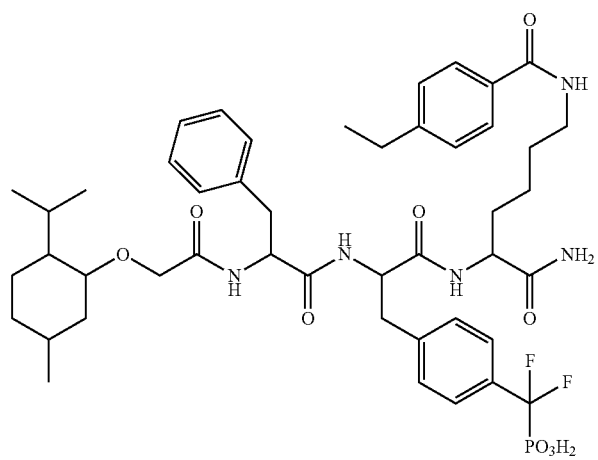

The PTP inhibitor compounds may be synthesized by condensing carboxylic acids with the amine groups of phosphonodifluoromethyl phenylalanine ($F_2$Pmp). The residues of carboxylic acids, which are $R^1$ and $R^2$, may be derived from the following carboxylic acids in Table 2.

TABLE 2

Examples of carboxylic acids that react with free amino groups of $F_2$Pmp

3-Dimethylaminobenzoic acid
2-(2-Cyanophenylthio)benzoic acid
2-(4-Chlorobenzoyl)benzoic acid
(−)-2-Oxo-4-thiazolidine-carboxylic acid
(−)-N-Acetylneuraminic acid
(+)-6-methoxy-a-methyl-2-naphthaleneacetic acid
(+)-Carbobenzyloxy-D-proline
(+)-Menthoxyacetic acid
(+_)-2-(2-Chlorophenoxy)propionic acid
(±)-1-Methyl-2-cyclohexene-1-carboxylic acid
(1-Naphthoxy)acetic acid
(1R)-(1a,2b,3a)-(+)-3-Methyl-2-nitromethyl-5-oxocyclopentaneacetic acid
(1R,4R)-7,7-dimethyl-2-oxobicyclo[2.2.1]heptane-1-carboxylic acid
(1S)-(+)-Camphanic acid
(1S,3R,4S,5R)-1,3,4,5-tetrahydroxy-cyclohexanecarboxylic acid
(2,4-Di-tert-pentylphenoxyl)acetic acid
(2-Naphthoxy)acetic acid
(2-pyrimidylthio)acetic acid
(4-Carboxybutyl)triphenyl-phosphonium bromide
(4-Chlorophenylthio)acetic acid
(4-Methylphenoxy)acetic acid
(a,a,a-trofluoro-m-tolyl)acetic acid
(E)-2-((4-hydroxyphenyl)diazenyl)benzoic acid
(E)-2-methyl-3-(2,4,5-trimethoxyphenyl)acrylic acid
(Methylthio)acetic acid
(R)-(−)-2-Hydroxy-4-phenylbutyric acid
(R)-(−)-3-Chloromandelic acid
(R)-(−)-Hexahydromandelic acid
(R)-(+)-2-Pyrrolidone-5-carboxylic acid
(R)-(+)-Citronellic acid
(R)-2-(1-phenylethylcarbamoyl)benzoic acid
(R)-2-hydroxy-2-phenylacetic acid
(R)-3,3,3-trifluoro-2-methoxy-2-phenylpropanoic acid
(R)-6-hydroxy-2,5,7,8-tetramethylchroman-2-carboxylic acid
(S)-(−)-Indoline-2-carboxylic acid
(S)-(+)-2-Oxo-4-phenyl-3-oxazolidineacetic acid
(S)-(+)-5-Oxo-2-tetrahydro-furancarboxylic acid
(S)-(+)-Hexahydromandelic acid
(S)-(+)-N-[1-(1-Naphthyl)-ethyl]-phthalamic acid
(S)-(+)-O-Acetylmandelic acid
(S)-2-(1-phenylethylcarbamoyl)benzoic acid
(S)-2-(4-isobutylphenyl)propanoic acid
(S)-2-(phenylcarbamoyloxy)propanoic acid
(S)-3-(benzyloxycarbonyl)-2-oxoimidazolidine-4-carboxylic acid
(S)-3,3,3-trifluoro-2-methoxy-2-phenylpropanoic acid
(S)-3,3,3-trifluoro-2-methoxy-2-phenylpropanoic acid
(S)-6-methoxy-2,5,7,8-tetramethylchroman-2-carboxylic acid
(Trimethylsilyl)acetic acid
(Z)-2-cyano-3-(3-hydroxyphenyl)acrylic acid
1-(4-Chlorophenyl)-1-cyclopentanecarboxylic acid
1-(tert-Butyl)hydrocinnamic acid
1,2-phenylenedioxydiacetic acid
1,4-Dihydro-2-methylbenzoic acid
1,4-Dihydroxy-2-naphthoic acid
10-Hydroxydecanoic acid
10-Undecynoic acid
1-Admantanecarboxylic acid
1-Cyano-1-cyclopropane-carboxylic acid
1-Hydroxy-2-naphthoic acid
1-Isoquinolinecarboxylic acid
1-Methyl-(1S,2R)-(+)-cis-1,2,3,6-tetrahydrophthalate
1-Methyl-1-cyclohexane-carboxylic acid
1-methyl-1H-indole-2-carboxylic acid
1-Methyl-2-pyrrolecarboxylic acid
1-Methylcyclopropane-carboxylic acid
1-Naphthoic acid TABLE 2-continued Examples of carboxylic acids that react with free amino groups of $F_2$Pmp 1-phenyl-1-cyclopentane-carboxylic acid
1-Phenyl-1-cyclopropane-carboxylic acid
1-Pyreneacetic acid
1-Pyrenebutyric acid
1-pyrenecarboxylic acid
2-((1R,2R,3R,4S)-3-hydroxy-4,7,7-trimethylbicyclo[2.2.1]heptan-2-yl)acetic acid
2-((benzyloxycarbonyl)(methyl)amino)-2-methylpropanoic acid
2-(2-(trifluoromethyl)phenyl)acetic acid
2-(2,4,5-Trichlorophenoxy)-propionic acid
2-(2,4-Dichlorophenoxy)-propionic acid
2-(3,5-dinitrobenzamido)-2-phenylacetic acid
2-(3,5-dinitrobenzamido)-4-methylpentanoic acid
2-(3-Chlorophenoxy)propionic acid
2-(4-(trifluoromethyl)phenyl)acetic acid
2-(4-chloro-3-nitrobenzoyl)-benzoic acid
2-(4-Chlorophenoxy)-2-methyl-propionic acid
2-(4-Chlorophenoxy)propionic acid
2-(4-Fluorobenzoyl)benzoic acid
2-(4-hydroxy-3-methoxyphenyl)acetic acid
2-(4-Hydroxyphenoxy)-propionic acid
2-(4-isobutylphenyl)propanoic acid
2-(4-Nitrophenyl)propionic acid
2-(benzyloxycarbonylamino)-3-(1H-indol-3-yl)propanoic acid
2-(Trifluoromethyl)acrylic acid
2-(trifluoromethyl)benzoic acid
2-(Trifluoromethyl)cinnamic acid
2,2,3,3-tetramethyl-cyclopropanecarboxylic acid
2,2-Bis(hydroxymethyl)-propionic acid
2,3,4,5,6-Pentafluoro-cinnamic acid
2,3,4,5,6-Pentafluorophenoxy acetic acid
2,3,4,5,6-Pentafluorophenyl-acetic acid
2,3,4,5-Tetrafluorobenzoic acid
2,3,4-Trifluorocinnamic acid
2,3,4-Trihydroxybenzoic acid
2,3,4-trimethoxybenzoic acid
2,3,5,6-Tetrafluoro-4-hydr-oxy-benzoic acid hydrate
2,3,5,6-Tetrafluorobenzoic acid
2,3,5,6-tetrafluoro-p-toluic acid
2,3,5-Triiodobenzoic acid
2,3,6-Trifluorobenzoic acid
2,3-Dichlorobenzoic acid
2,3-Difluorobenzoic acid
2,3-dihydroxybenzoic acid
2,3-Dimethylbenzoic acid
2,4,5-Trichlorophenoxyacetic acid
2,4,5-Trimethoxybenzoic acid
2,4,6-Trichlorobenzoic acid
2,4,6-Trifluorobenzoic acid
2,4,6-Trihydroxybenzoic acid monohydrate
2,4,6-Trimethylbenzoic acid
2,4-Bis(trifluoromethyl)-benzoic acid
2,4-Dichloro-5-fluorobenzoic acid
2,4-Dichloro-5-sulfamoyl-benzoic acid
2,4-dichlorobenzoic acid
2,4-Dichlorophenylacetic acid
2,4-Difluorobenzoic acid
2,4-Difluorophenylacetic acid
2,4-Dihydroxybenzoic acid
2,4-Dimethylbenzoic acid
2,4-dinitrobenzoic acid
2,4-Dinitrophenylacetic acid
2,4-Hexadienoic acid
2,5-Bis(trifluoromethyl)-benzoic acid
2,5-dichlorobenzoic acid
2,5-Difluorobenzoic acid
2,5-Difluorophenylacetic acid
2,5-Dihydroxybenzoic acid
2,5-Dihydroxyphenylacetic acid
2,5-Dimethoxybenzoic acid
2,5-Dimethoxycinnamic acid
2,6-Dichloro-3-nitrobenzoic acid
2,6-Difluorobenzoic acid
2,6-Difluorophenylacetic acid
2,6-Dihydroxybenzoic acid
2,6-dimethoxynicotinic acid
2,6-Dimethylbenzoic acid TABLE 2-continued Examples of carboxylic acids that react with free amino groups of $F_2Pmp$ 2,6-Heptadienoic acid
2-[4-(Dibutylamino)-2-hydroxy-benzoyl]benzoic acid
2-Bibenzylcarboxylic acid
2-Biphenylcarboxylic acid
2-Bromo-3-nitrobenzoic acid
2-Bromo-4,5-dimethoxybenzoic acid
2-Bromo-5-methoxybenzoic acid
2-Bromo-5-nitrobenzoic acid
2-Bromoacrylic acid
2-bromophenylacetic acid
2-Chloro-3-nitrobenzoic acid
2-chloro-4,5-difluorobenzoic acid
2-Chloro-4-fluorobenzoic acid
2-Chloro-5-(methylthio)-benzoic acid
2-Chloro-5-(trifluoro-methyl)benzoic acid
2-chloro-5-nitrobenzoic acid
2-chloro-5-nitrocinnamic acid
2-Chloro-6-fluorobenzoic acid
2-chloro-6-fluorophenylacetic acid
2-Chloro-6-methylnicotinic acid
2-Chlorobenzoic acid
2-Chloronicotinic acid
2-Chlorophenylacetic acid
2-Chloropropionic acid
2-Ethoxy-1-naphthoic acid
2-Ethoxybenzoic acid
2-Ethyl-2-hydroxybutyric acid
2-Ethylbutyric acid
2-Ethylhexanoic acid
2-Ethylthio-2,2-diphenyl-acetic acid
2-Fluoro-3-(trifluoromethyl)-benzoic acid
2-Fluoro-4-(trifluoromethyl)-benzoic acid
2-Fluoro-5-methylbenzoic acid
2-fluoro-5-nitrobenzoic acid
2-Fluoro-6-(trifluoromethyl)-benzoic acid
2-Fluorobenzoic acid
2-Fluorocinnamic acid
2-Fluorophenylacetic acid
2-Hydroxy-3-isopropyl-6-methylbenzoic acid
2-Hydroxy-3-isopropylbenzoic acid
2-Hydroxy-3-methylbutyric acid
2-Hydroxy-6-Isopropyl-3-methylbenzoic acid
2-hydroxycaproic acid
2-hydroxyhippuric acid
2-hydroxyisobutyric acid
2-hydroxyisobutyric acid
2-Hydroxynicotinic acid
2-Hydroxyphenylacetic acid
2-Iodobenzoic acid
2-Mercaptonicotinic acid
2-methoxy-2-phenylacetic acid
2-Methoxy-4-(methylthio)-benzoic acid
2-Methoxy-4-nitrobenzoic acid
2-Methoxyphenylacetic acid
2-Methyl-1-cyclohexane-carboxylic acid (cis and trans)
2-Methyl-3-nitrobenzoic acid
2-methyl-3-phenylpropanoic acid
2-Methyl-4-oxo-4-phenylbutyric acid
2-Methyl-6-nitrobenzoic acid
2-Methylbutyric acid
2-Methylcinnamic acid
2-Methylcyclopropane-carboxylic acid (cis&trans)
2-methylhexanoic acid
2-Methylhippuric acid
2-Methylhydrocinnamic acid
2-Methylvaleric acid
2-Naphthoic acid
2-naphthylacetic acid
2-nitro-4-(trifluoromethyl)benzoic acid
2-nitrobenzoic acid
2-Norbornaneacetic acid
2-Oxo-6-pentyl-2H-pyran-3-carboxylic acid
2-Phenoxybenzoic acid
2-Phenoxybutyric acid
2-Phenoxypropionic acid
2-propylpentanoic acid
2-Quinoxalinecarboxylic acid TABLE 2-continued Examples of carboxylic acids that react with free amino groups of $F_2Pmp$ 2-Thiopheneacetic acid
2-thiopheneacetic acid
2-Thiopheneglyoxylic acid
3-(2-Hydroxyphenyl)propionic acid
3-(2-Thienyl)acrylic acid
3-(3,4,5-Trimethoxyphenyl)-propionic acid
3-(3,4-Dimethoxyphenyl)-propionic acid
3-(3-hydroxy-2,4,6-triiodophenyl)pentanoic acid
3-(3-Hydroxyphenyl)-propionic acid
3-(3-methoxyphenyl)propionic acid
3-(4-chlorobenzoyl)propionic acid
3-(4-Chlorobenzoyl)propionic acid
3-(4-Chlorobenzoyl)propionic acid
3-(4-Fluorobenzoyl)propionic acid
3-(4-Hydroxyphenyl)propionic acid
3-(Phenylsulfonyl)propionic acid
3-(Trifluoromethyl)cinnamic acid
3-(Trimethylsilyl)propynoic acid
3,3,3-Triphenylpropionic acid
3,4-(methylenedioxy)cinnamic acid
3,4-(Methylenedioxy)phenyl-acetic acid
3,4-Dichlorobenzoic acid
3,4-Dichlorophenoxyacetic acid
3,4-Diethoxybenzoic acid
3,4-Difluorobenzoic acid
3,4-Dihydroxybenzoic acid
3,4-dihydroxyhydrocinnamic acid
3,4-Dihydroxyphenylacetic acid
3,5,6-Trichlorosalicylic acid
3,5-Bis(trifluoromethyl)-phenyl acetic acid
3,5-Dibromobenzoic acid
3,5-Dichlorosalicyclic acid
3,5-Difluorocinnamic acid
3,5-Dihydroxy-2-naphthoic acid
3,5-dinitrobenzoic acid
3,5-Dinitro-o-toluic acid
3,5-Dinitro-p-toluic acid
3,5-Dinitrosalicyclic acid
3,5-Di-tert-butyl-4-hydroxy-benzoic acid
3,5-Di-tert-butylbenzoic acid
3,7-Dihydroxy-2-naphthoic acid
3,Thiopheneacetic acid
3-Benzoyl-2-pyridine-carboxylic acid
3-benzoylbenzoic acid
3-Bromo-4-fluorobenzoic acid (95%)
3-bromo-4-methylbenzoic acid
3-Bromo-5-iodobenZoic acid
3-Bromobenzoic acid
3-Bromocinnamic acid
3-Carboxy-PROXYL
3-Chloro-2-nitrobenzoic acid
3-Chloro-4-fluorobenzoic acid
3-Chloro-4-Hydroxyphenyl-acetic acid
3-Chlorosalicylic acid
3-Cyanobenzoic acid
3-fluoro-2-methylbenzoic acid
3-Fluoro-4-hydroxy-phenylacetic acid
3-Fluoro-4-methoxybenzoic acid
3-Fluorophenylacetic acid
3-furoic acid
3-Hydroxy-2-naphthoic acid
3-Hydroxy-2-quinoxaline-carboxylic acid
3-Hydroxy-4-methoxybenxoic acid
3-Hydroxy-4-methoxy-cinnamic acid
3-Hydroxy-4-nitrobenzoic acid
3-Hydroxybenzoic acid
3-Hydroxybutyric acid
3-Hydroxyphenylacetic acid
3-Indolebutyric acid
3-Indoleglyoxylic acid
3-Indolepropionic acid
3-Iodo-4-methylbenzoic acid
3-iodobenzoic acid
3-Isoquinolinecarboxylic acid hydrate
3-Methoxy-4-nitrobenzoic acid
3-Methoxycyclohexane-carboxylic acid (cis&trans)
3-Methyl-2-phenyvaleric acid TABLE 2-continued Examples of carboxylic acids that react
with free amino groups of F$_2$Pmp 3-Methylhippuric acid
3-Methylindene-2-carboxylic acid
3-Methylsalicyclic acid
3-Methylvaleric acid
3-Nitreobenzoic acid
3-Nitrophenylacetic acid
3-Nitropropionic acid
3-Noradamantanecarboxylic acid
3-Oxo-1-indancarboxylic acid
3-Phenoxybenzoic acid
3-Phenylbutyric acid
3-p-tolylpropanoic acid
3-thiophenecarboxylic acid
4-(1,3-dioxoisoindolin-2-yl)-2-hydroxybutanoic acid
4-(2,4,5-Trichlorophenoxy)-butyric acid
4-(2,4-Dichlorophenoxy)-butyric acid
4-(2,4-Di-tert-pentylphenoxy)butyric acid
4-(2-Phenoxyethoxy)benzoic acid
4-(3,4-Dimethoxyphenyl)-butyric acid
4-(4-Methoxyphenyl)butyric acid
4-(4-Nitrophenyl)butyric acid
4-(Diethylamino)benzoic acid
4-(Dimethylamino)cinnamic acid
4-(Dimethylamino)phenyl-acetic acid
4-(Ethylthio)benzoic acid
4-(Hydroxymethyl)benzoic acid
4-(Methylsulfonyl)benzoic acid
4-(Methylthio)benzoic acid
4-(Methylthio)phenylacetic acid
4-(Trifluoromethoxy)benzoic acid
4'-(trifluoromethyl)biphenyl-2-carboxylic acid
4-(Trifluoromethyl)mandelic acid
4,4,4-Trifluoro-3-methyl-2-butenoic acid
4,4-Bis(4-hydroxyphenyl)-valeric acid
4,5-Dimethoxy-2-nitrobenzoic acid
4,6-Dioxoheptanoic acid
4-[4-(2-Carboxybenzoyl)-phenyl]butyric acid
4-Acetamidobenzoic acid
4-Acetylbenzoic acid
4-Acetylphenoxyacetic acid
4-Benzyloxy-3-methoxyphenyl-acetic acid
4-Biphenylacetic acid
4-Bromo-3,5-dihydroxy-benzoic acid
4-bromobenzoic acid
4-Bromocinnamic acid
4-bromophenylacetic acid
4-Butoxybenzoic acid
4-Butoxyphenylacetic acid
4-Butylbenzoic acid
4-Chloro-2,5-difluorobenzic acid
4-Chloro-3-sulfamoylbenzoic acid
4-Chlorobenzoic acid
4-Chloro-o-tolyloxyacetic acid
4-chlorophenylacetic acid
4-Chlorosalicylic acid
4-Ethoxycarbonyloxy-3,5-dimethoxybenzoic acid
4-Ethoxyphenylacetic acid
4-Ethylbenzoic acid
4'-ethylbiphenyl-4-carboxylic acid
4-Fluorenecarboxylic acid
4-Fluoro-1-naphthoic acid
4-Fluoro-2-(trifluoromethyl)-benzoic acid
4-fluoro-3-nitrobenzoic acid
4-fluorobenzoic acid
4-fluorobenzoic acid
4-Fluorocinnamic acid
4-Fluorophenoxyacetic acid
4-Heptyloxybenzoic acid
4-Hexylbenzoic acid
4-hexyloxybenzoic acid
4-Hydroxy-3-(morpholino-methyl)benzoic acid hydrate
4-Hydroxy-3,5-dinitrobenzoic Acid
4-Hydroxy-3-methoxy-benzoic acid
4-Hydroxy-3-methoxy-mandelic acid
4-Hydroxy-3-nitrobenzoic acid
4-Hydroxy-3-nitrophenylacetic acid
4-Hydroxybenzoic acid 4'-hydroxybiphenyl-4-carboxylic acid
4-Hydroxyphenylacetic acid
4-Hydroxyphenylacetic acid
4-Hydroxyphenylpyruvic acid
4-iodobenzoic acid
4-Isopropoxybenzoic acid
4-Methoxy-3-nitrobenzoic acid
4-methoxycyclohexane-carboxylic acid
4-Methoxysalilcylic acid
4-Methyl-1-cyclohexane-carboxylic acid (cis and trans)
4-Methyl-3-nitrobenzoic acid
4-Methylhippuric acid
4-Methylsalicyclic acid
4-Methylvaleric acid
4-Nitro-3-pyrazolecarboxylic acid
4-Nitrohippuric acid
4-Nonyloxybenzoic acid
4-Octylbenoic acid
4-Oxo-4H-1-benzopyran-2-carboxylic acid
4-Oxo-6-phenyl-5-hexenoic acid
4-Pentenoic acid
4-pentylbenzoic acid
4-Pentylbicyclo[2.2.]octane-1-carboxylic acid
4-Pentyloxybenzoic acid
4-Pentynoic acid
4-Phenylbutyric acid
4-Propoxybenzoic acid
4-propylbenzoic acid
4-Pyrazolecarboxylic acid
4-tert-Butylbenzoic acid
4-tert-Butylcyclohexanecarboxylic acid
4-Vinylbenzoic acid
5-(4-chlorophenyl)-2-furoic acid
5,6-Dichloronicotinic acid
5-Bromo-2,4-dihydroxybenzoic acid
5-Fluoro-2-methylbenzoic acid
5-fluoroindole-2-carboxylic acid
5-Fluorosalicylic acid
5-hydantoinacetic acid
5-Hydroxy-2-Indole-carboxylic acid
5-Methoxy-1-indanone-3-acetic acid
5-Methoxy-2-methyl-3-indoleacetic acid
5-methoxy-2-nitrobenzoic acid
5-Methoxysalicylic acid
5-Methyl-2-nitrobenzoic acid
5-Methyl-2-pyrazine-carboxylic acid
5-Nitro-2-furoic acid
5-Nitro-3-pyrazolecarboxylic acid
5-Phenylvaleric acid
6-(Carbobenzyloxyamino)-caproic acid
6-Acetamidohexnoic acid
6-Bromohexanoic acid
6-chloronicotinic acid
6-hydroxy-2,5,7,8-tetramethylchroman-2-carboxylic acid
6-Methylchromone-2-carboxylic acid
6-Methylnicotinic acid
6-Nitrocaproic acid
6-Oxoheptaoic acid
6-Phenylhexanoic acid
7-(Carboxymethyoxy)-4-methylcoumarin
7-Hydroxycoumarin-4-acetic acid
7-Methoxy-2-benzofuran-carboxylic acid
7-Methoxycoumarin-4-acetic acid
7-Oxoctanoic acid
9-Anthracenecarboxylic acid
9-Fluoreneacetic acid
9-Fluorenone-1-carboxylic acid
A,a,a-Trifluoro-m-toluic acid
a-Acetamidocinnamic acid
Abietic acid
acetic acid
Acetic Acid
Acetic Acid
Acetyl-L-asparagine
Acetylsalicyclic acid
Acetylsalicyclic acid
a-cyano-4-hydroxycinnamic acid TABLE 2-continued Examples of carboxylic acids that react with free amino groups of F$_2$Pmp Adipic acid monoethyl ester
a-hydroxyhippuric acid
Anthranilic acid
anti-3-Oxotricyclo[2.2.1.02,6]heptane-7-carboxylic acid
a-phenylcyclopentaneacetic acid
a-Phenyl-o-toluic acid
Atrolactic acid
Benzilic acid
Benzotriazole-5-carboxylic acid
Benzoylformic acid
Bis(4-chlorophenyl)acetic acid
Carbobenzyloxy-DL-alanine
Carbobenzyloxy-L-alanine
Carbobenzyloxy-l-glutamine
Carbobenzyloxy-L-valine
Cis-2-Methoxycinnamic acid
Crotonic acid
Cyclohexanebutyric acid
Cyclohexanecarboxylic acid
Cyclohexanepentanoic acid
Cyclohexanepropionic acid
Cyclopentylacetic acid
D,L-3,4-Dihydroxymandelic acid
D-3-Phenyllactic acid
Decanoic acid
Dicyclohexylacetic acid
Diethylphosphonoacetic acid
Dikegulac hydrate
Diphenylacetic acid
Fumaric acid monoethyl ester
Fusaric acid
Gallic acid
Geranic acid
Glycolic acid
Heptadecafluorononanoic acid
Heptanoic acid
Heptanoic acid
Hexanoic acid
Hippuric acid
Hydrocinnamic acid
Indole-3-carboxylic acid
Indole-4-carboxylic acid
Isovaleric acid
L-3-Phenyllactic acid
Lauric acid
L-Lactic acid (85%)*
Maleamic acid
Methoxyacetic acid
Mono-(1R)-(−)-Menthyl phthalate
Mono-(1S)-(+)-Menthyl phthalate
Mono-methyl cis-5-norbornene-endo-2,3-dicarboxylate
Mono-Methyl phthalate
Mono-Methylterephthalate
N-(2-Furoyl)glycine
n-(3,5-dinitrobenzoyl)-DL-a-phenylglycine
N-(3-Indolylacetyl)-L-alanine
N-(3-Indolylacetyl)-L-isoleucine
N-(3-Indolylacetyl)-L-leucine
N-(3-Indolylacetyl)-L-phenylalanine
N-(3-Indolylacetyl)-L-valine
N-(carbobenzyloxy)-l-phenyl-alanine
N,N-Diethyl-3,6-difluoro-phthalamic acid
N-[(R)-1-(1-Naphthyl)ethyl]-phthalamic acid
N-[5-(Trifluoromethyl)-2-pyridyl]-L-valine
n-acetyl-4-fluoro-DL-phenylalanine
N-Acetyl-DL-tryptophan
n-acetyl-l-leucine
N-acetyl-L-methionine
N-Acetyl-L-phenylalanine
N-Acetyl-L-phenylalanine
n-acetyl-l-tyrosine
N-Benzoyl-(2R,3S)-3-phenyl-Isoserine
N-Benzoyl-L-threonine
N-Carbobenzyloxy-2-methyl-alanine
N-Carbobenzyloxy-L-glutamic acid 1-methyl ester
N-Carbobenzyloxy-L-isoleucine
N-Carbobenzyloxy-L-Leucine
n-carbobenzyloxy-l-threonine
n-ethoxycarbonyl-l-phenylalanine
Nonanoic acid
N-p-Tosylglycine
N-p-Tosyl-L-phenylalanine
o-anisic acid
p-Anisic acid
Pentafluorobenzoic acid
Phenoxyacetic acid
Phenylacetic acid
Podocarpic acid
Pyruvic acid
Rhodanine-3-acetic acid
S-(Thiobenzoyl)thioglycolic acid
s-benzyl-n-carbobenzyloxy-l-cysteine
Sebacic acid monomethyl ester
Succinamic acid
Succinic 2,2-dimethyl-hydrazide
Tetrahydro-2-furoic acid
Trans-1-Acetyl-4-hydroxy-L-proline
Trans-2,3-Dimethoxycinnamic acid
Trans-2,4-Dichlorocinnamic acid
Trans-2,4-Difluorocinnamic acid
Trans-2,5-Difluorocinnamic acid
Trans-2,6-Difluorocinnamic acid
Trans-2-Chloro-6-fluro-cinnamic acid
Trans-2-Hexenoic acid
Trans-3-(2,3,5,6-Tetramethyl-benzoyl)acrylic acid
Trans-3-(2,5-dimethylbenzo-yl)-acrylic acid
Trans-3-(4-ethoxy-benzoyl)acrylic acid
Trans-3-(4-methoxybenzoyl)-acrylic acid
Trans-3-(4-Methylbenzoyl)-acrylic acid
Trans-3,4-Difluorocinnamic acid
Trans-3-Fluorocinnamic acid
Trans-3-Furanacrylic acid
Trans-3-Hexenoic acid
Trans-4-chloro-3-nitrocinnamic acid
Trans-4-hydroxy-3-methoxy-cinnamic acid
Trans-4-Hydroxy-3-methoxy-cinnamic acid
Trans-4-Methyl-1-cyclohexa-ne carboxylic acid
Trans-4-Pentylcyclohexane carboxylic acid
Trans-5-Bromo-2-methoxy cinnamic acid
Trans-Styrylacetic acid
Trans-Styrylacetic acid
Tridecafluoroheptanoic acid
Trimethylacetic acid
Triphenylacetic acid
Valeric acid
Yohimbinic acid, mono-hydrate Example 1

Dimethylformamide (DMF), isopropanol, dichloromethane (DCM) and N-methyl morpholine (NMM), acetic acid (AcOH) were from Fisher Scientific. Diethyl ether, piperidine, trifluoroacetic acid (TFA), triisopropylsilane (TIS), tetrakis-(triphenylphosphine)-palladium(0), 4-ethylbenzoic acid (pEBA) and (+)-menthyloxyacetic acid (MOA) were from Aldrich. Rink amide resin, O-benzotriazole-N,N,N,N'-tetramethyluroniumhexafluorophosphate (HBTU), N-hydroxybenzotriazole (HOBt), Fmoc-Phe-OH, Fmoc-Lys(Alloc)-OH, Fmoc-Lys(Boc)-OH, Fmoc-Ala-OH, Fmoc-Phe(4-I)-OH and 9-fluorenylmethyl chloroformate (Fmoc-Cl) were from ADVANCED CHEMTECH. 5-(and-6)-carboxyfluorescein, succinimidyl ester (5-(6)-FAM, SE) was from Invitrogen. Fmoc-F$_2$Pmp-OH was prepared following procedures described in Qiu & Burton, *Tetrahedron Letters* (37): 2745-48 (1996) and Gordeev, et al. *Tetrahedron Letters* (35):7585-88 (1994).

HPLC purification was carried out on a Waters Breeze HPLC system equipped with a WATERS ATLANTIS dC$_{18}$ column (19 mm×50 mm).

General Procedures

General Procedure a for Rink Amide Resin Activation.

Rink amide resin was mixed with DCM (1 mL per 100 mg resin), and then shaken for 30 minutes. After activation, resin was washed three times with DMF (1 mL per 100 mg resin).

General Procedure B for the Removal of the Fmoc Group from the Rink Amide Resin.

Rink amide Resin was mixed with 30% piperidine in DMF, and then shaken for 30 minutes. Resin was then washed with DMF (1 mL per 100 mg resin, 3 times), isopropanol (1 mL per 100 mg resin, 3 times) and DCM (1 mL per 100 mg resin, 3 times). The removal of Fmoc group was confirmed by ninhydrin test.

General Procedure C for the Removal the Alloc Group from the Rink Amide Resin.

Resin was first washed with DCM (1 mL per 100 mg resin, 5 times). Under N$_2$ protection, the resin was shaken with a solution of tetrakis-(triphenylphosphine)-palladium (0) (10 mg), AcOH (0.5 mL), NMM (0.2 mL) in DCM (10 mL) overnight. Resin was then washed with DMF (1 mL per 100 mg resin, 3 times), isopropanol (1 mL per 100 mg resin, 3 times) and DCM (1 mL per 100 mg resin, 3 times). The removal of Alloc group was confirmed by ninhydrin test.

General Procedure D for Coupling Carboxylic Acid to the Rink Amide Resin.

Carboxylic acid (5 equiv, 0.5 M in DMF) was mixed with HBTU (5 equiv, 0.5 M in DMF), HOBt (5 equiv, 0.5 M in DMF) and NMM (15 equiv, 1.5 M in DMF). The mixed solution was then added to resin, and then shaken for 2 hours. Resin was then washed with DMF (1 mL per 100 mg resin, 3 times), isopropanol (1 mL per 100 mg resin, 3 times) and DCM (1 mL per 100 mg resin, 3 times). The completion of the coupling reaction was confirmed by ninhydrin test.

General Procedure E for Peptide Cleavage from the Rink Amide Resin.

Resin was first washed with DCM (1 mL per 100 mg resin, 5 times). Resin was then shaken with 95% TFA, 2.5% TIS and 2.5% H$_2$O. The resin was removed by filtration, and the TFA was evaporated under vacuum. The crude peptide was obtained after triturated with 5 mL diethyl ether for two times.

Example 2

Synthesis of Compound 4

Compound 4 was synthesized according Scheme S1, on Rink amide resin (ADVANCED CHEMTECH) using standard Fmoc chemistry. The resin (200 mg, 0.5 mmol/g loading) was first activated with DCM (general procedure A). Resin was then treated with 30% piperidine to remove the Fmoc group (general procedure B). The resin was coupled with Fmoc-Lys(Alloc)-OH (general procedure D). The Alloc group was removed using general procedure C, and resin was coupled with AcOH. The Fmoc group was then removed and resin was coupled with Fmoc-F$_2$Pmp-OH. The Fmoc group was removed and resin was coupled with AcOH. Compound 4 was then cleaved from resin (General procedure E). The crude peptide was purified by HPLC to afford 4 (12.3 mg, 24% yield). Mass calculated for [M] 506. found [M+H]$^+$ 507.

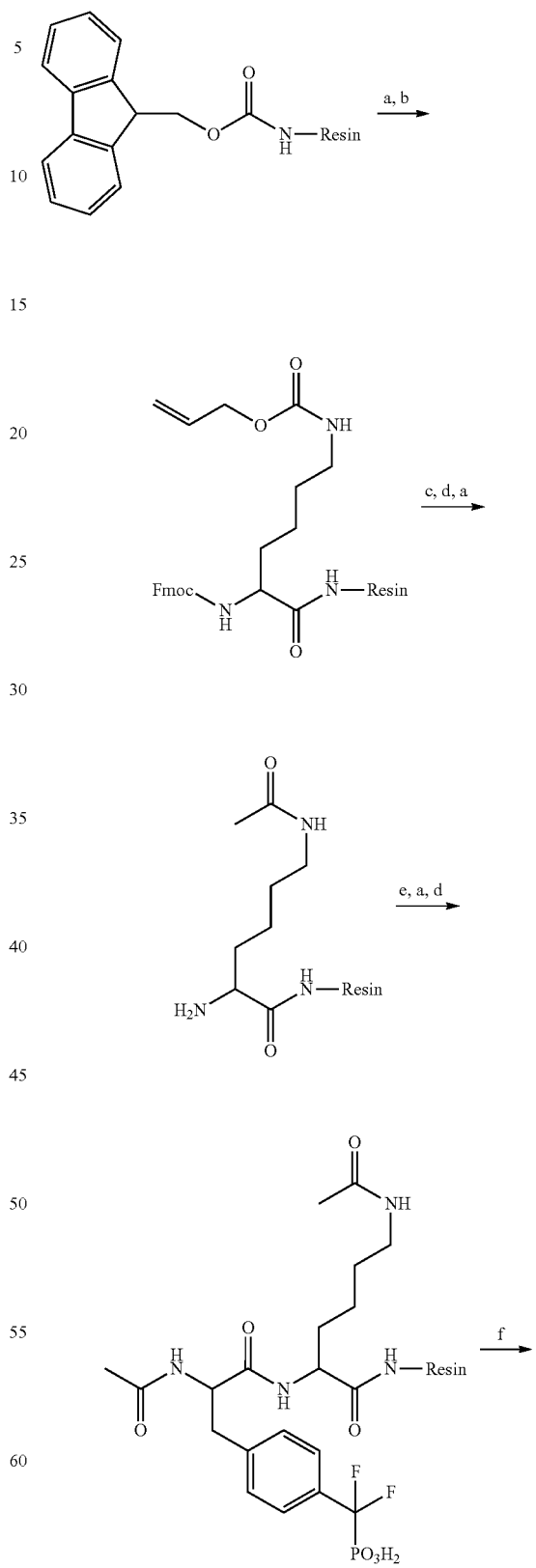

Scheme S1. Synthesis of 4.

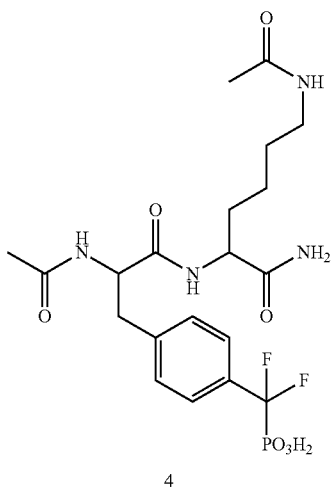

4

(a) 30% piperidine/DMF; (b) Fmoc-Lys(Alloc)-OH/HBTU/HOBt/NMM;
(c) Tetrakis-(triphenylphosphine)-palladium(0), AcOH/NMM/CH$_2$Cl$_2$;
(d) AcOH/HBTU/HOBt/NMM; (e) Fmoc-F$_2$Pmp-OH/HBTU/HOBt/NMM;
(f) TFA/H$_2$O/TIS (95:2.5:2.5).

Example 3

Synthesis of Precursor 5 for the First Generation Library

Synthesis of Compound S1.

Compound S1 was synthesized according Scheme S2, on Rink amide resin (ADVANCED CHEMTECH) using standard Fmoc chemistry. The resin (200 mg, 0.5 mmol/g loading) was first activated (general procedure A). Then Fmoc group was removed with 30% piperidine in DMF (general procedure B). The resin was then coupled with Fmoc-Lys(Boc)-OH (general procedure D). The resin was then sequentially coupled with Fmoc-Ala-OH, Fmoc-Lys (Alloc)-OH, Fmoc-F$_2$Pmp-OH and AcOH. The Alloc group was then removed (general procedure C). The resin was shaken with Fmoc-Cl (0.2 M in DMF, 2.5 mL) and NMM (1.5 M in DMF, 0.5 mL) for 2 hours. The compound S1 was then cleaved from resin (general procedure E). Crude peptide was purified by HPLC to afford S1 (24.3 mg, 27% yield). Mass calculated for [M] 885. found [M+H]$^+$ 886.

Synthesis of Compound S2.

Compound S1 (24.3 mg) was treated with 5(6)-FAM SE (20 mg) and NMM (0.1 mL) in DMF (5 mL) overnight. After evaporation of solvents, the crude product was purified by reversed-phase HPLC to afford S2 (11.2 mg, 33% yield). Mass calculated for [M] 1243. found [M+H]$^+$ 1244.

Synthesis of Compound 5.

Compound S2 (11.2 mg) was treated with 30% piperidine in DMF (10 mL) for 30 min. After evaporation of solvents, the crude product was purified by reversed-phase HPLC to afford 5 (4.7 mg, 51% yield). Mass calculated for [M] 1021. found [M+H]$^+$ 1022.

Scheme S2. Synthesis of the precursor 5 for the first generation library.

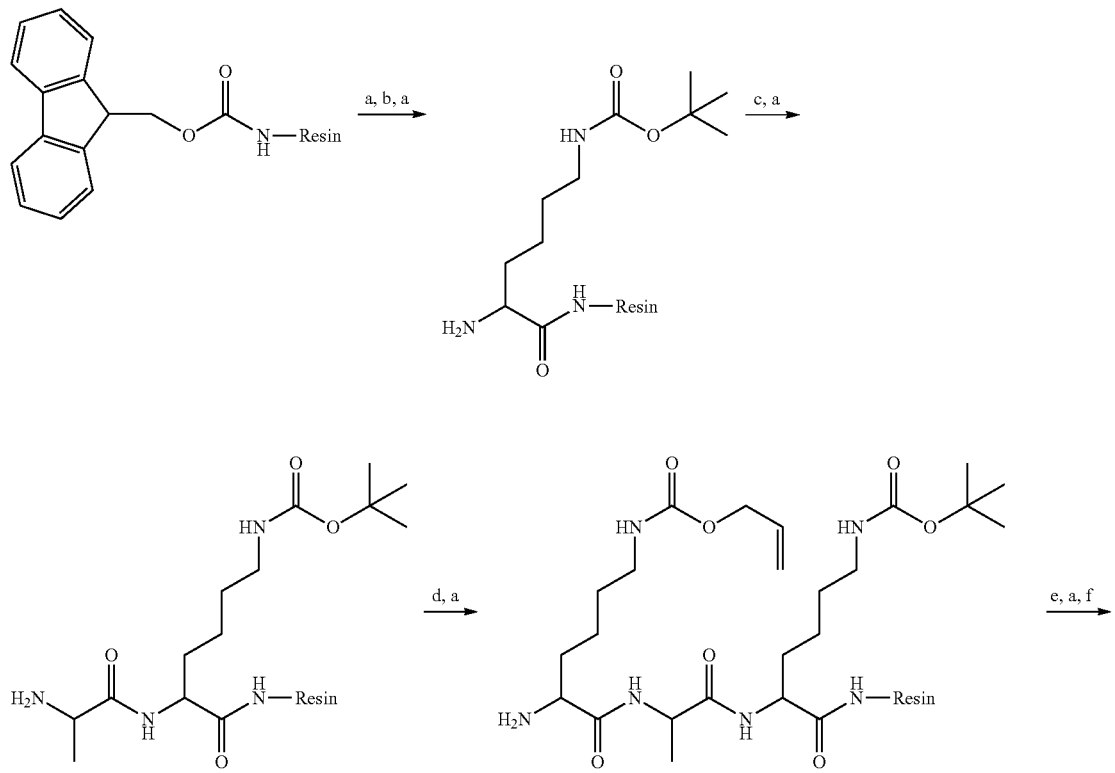

-continued
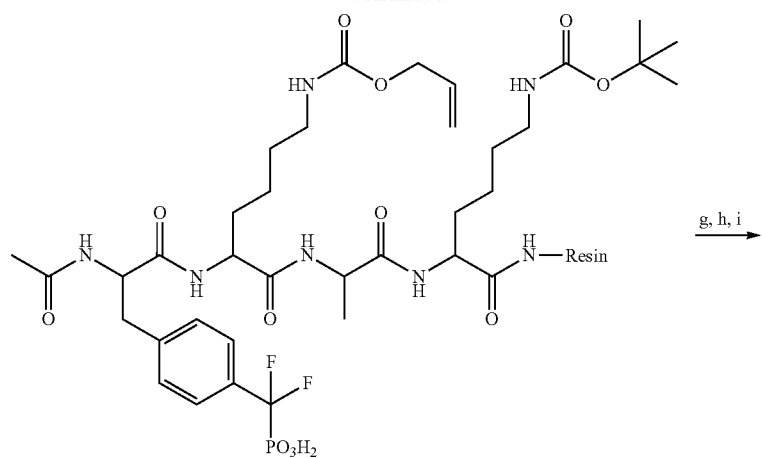
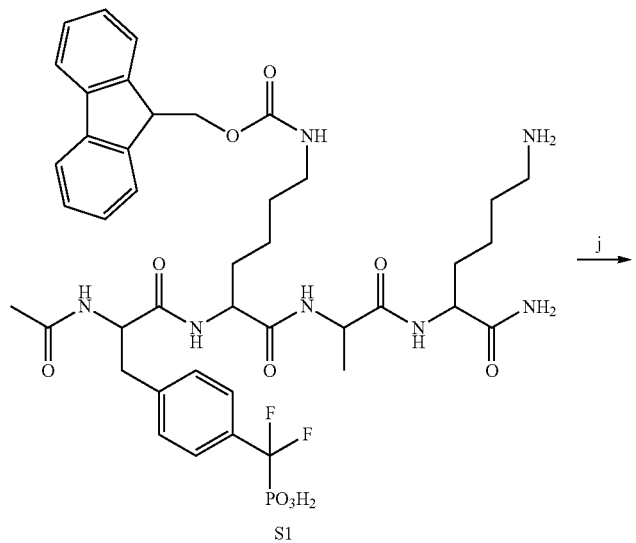
S1
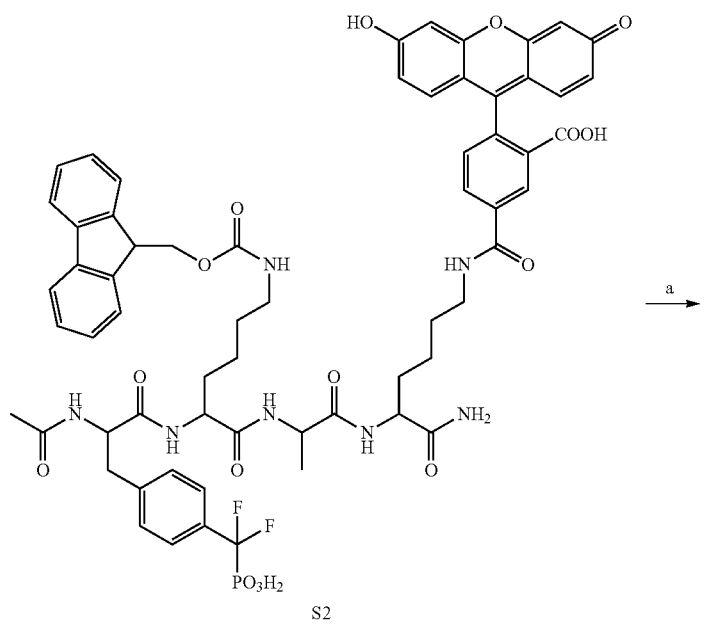
S2

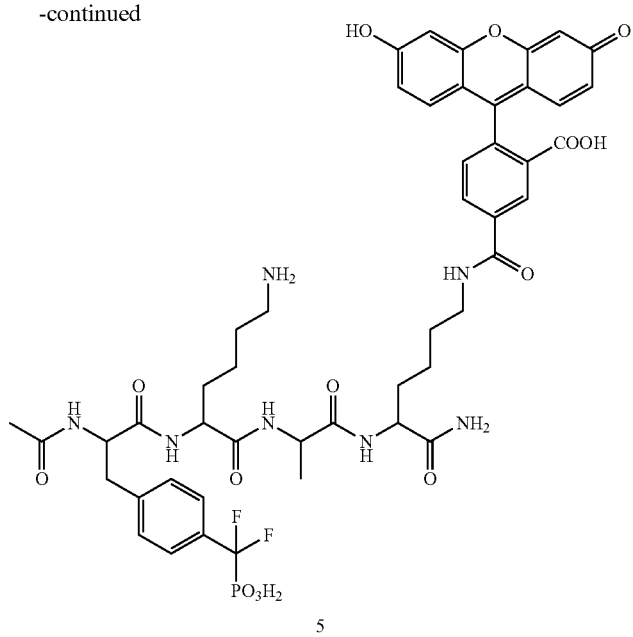

5

(a) 30% piperidine/DMF; (b) Fmoc-Lys(Boc)-OH/HBTU/HOBt/NMM; (c) Fmoc-Ala-OH/HBTU/HOBt/NMM; (d) Fmoc-Lys(Alloc)-OH/HBTU/HOBt/NMM;
(e) Fmoc-F$_2$Pmp-OH/HBTU/HOBt/NMM; (f) AcOH/HBTU/HOBt/NMM; (g) Tetrakis-(triphenylphosphine)-palladium(0), AcOH/NMM/CH$_2$Cl$_2$;
(h) Fmoc—Cl/NMM; (i) TFA/H$_2$O/TIS (95:2.5:2.5); (j) 5-(and-6)-carboxyfluorescein, succinimidyl ester/NMM.

Example 4

Synthesis of Compound 6

Compound 6 was synthesized according Scheme S3, on Rink amide resin (ADVANCED CHEMTECH) using standard Fmoc chemistry. The resin (200 mg, 0.5 mmol/g loading) was first activated (general procedure A). The resin was treated with 30% piperidine to remove the Fmoc group (general procedure B). The resin was coupled with Fmoc-Lys(Alloc)-OH (general procedure D). The Alloc group was removed (general procedure C) and resin was coupled with 4-ethylbenzoic acid. After removal of Fmoc group, resin was then coupled with Fmoc-F$_2$Pmp-OH and AcOH sequentially. Compound 6 was then cleaved from resin (general procedure E). The crude product was purified by HPLC to afford 6 (15.8 mg, 27% yield). Mass calculated for [M] 596. found [M+H]$^+$ 597.

Scheme S3. Synthesis of 6.

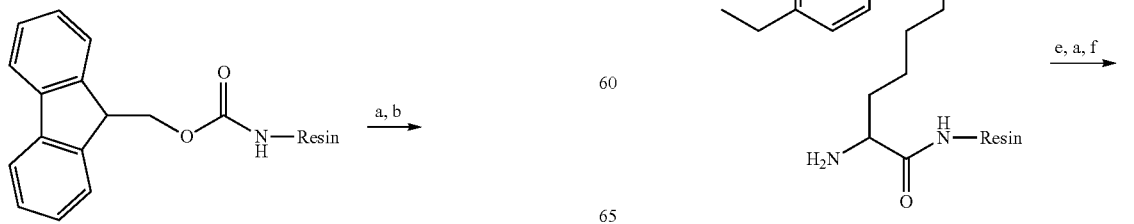

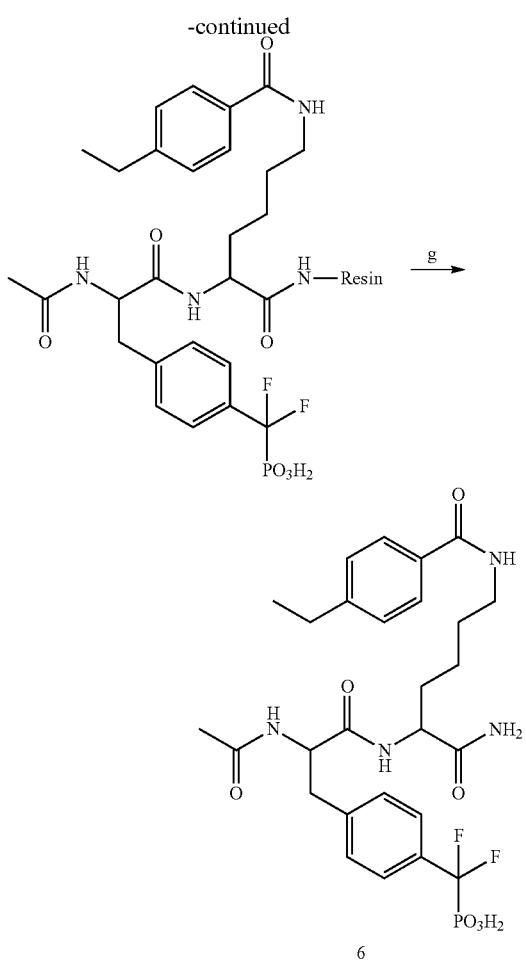

(a) 30% piperidine/DMF;
(b) Fmoc—Lys(Alloc)—OH/HBTU/HOBt/NMM;
(c) Tetrakis-(triphenylphosphine)-palladium(0), AcOH/NMM/CH$_2$Cl$_2$;
(d) 4-Ethylbenzoic acid/HBTU/HOBT/NMM;
(e) Fmoc—F$_2$Pmp—OH/HBTU/HOBt/NMM;
(f) AcOH/HBTU/HOBt/NMM;
(g) TFA/H$_2$O/TIS (95:2.5:2.5).

Example 5

Synthesis of Precursor 7 for the Second Generation Library

Synthesis of Compound S3.

Compound S3 was synthesized according scheme S4, on Rink amide resin (ADVANCED CHEMTECH) using standard Fmoc chemistry. The resin (200 mg, 0.5 mmol/g loading) was first activated (general procedure A). Then Fmoc group was removed (general procedure B). The resin was coupled with Fmoc-Lys(Boc)-OH (general procedure D). The resin was then sequentially coupled with Fmoc-Ala-OH, Fmoc-Lys(Alloc)-OH in the same procedure. Then, the Alloc group was removed (general procedure C). The resin was the coupled with 4-ethylbenzoic acid. The Fmoc group was removed, and resin was coupled with Fmoc-F$_2$Pmp-OH. The compound S3 was then cleaved from resin (general procedure E). The crude product was purified by HPLC to afford S3 (25.5 mg, 26% yield). Mass calculated for [M] 975. found [M+H]$^+$ 976.

Synthesis of Compound S4.

Compound S3 (25.5 mg) was treated with 5(6)-FAM SE (20 mg) and NMM (0.1 mL) in DMF (5 mL) overnight. After evaporation of solvents, the crude product was purified by reversed-phase HPLC to afford S4 (9.4 mg, 27% yield). Mass calculated for [M] 1333. found [M+H]$^+$ 1334.

Synthesis of Compound 7.

Compound S4 (9.4 mg) was treated with 30% piperidine in DMF (10 mL) for 30 min. After evaporation of solvents, the crude product was purified by reversed-phase HPLC to afford 7 (3.6 mg, 46% yield). Mass calculated for [M] 1111. found [M+H]$^+$ 1112.

Scheme S4. Synthesis of the precursor 7 for the second generation library.

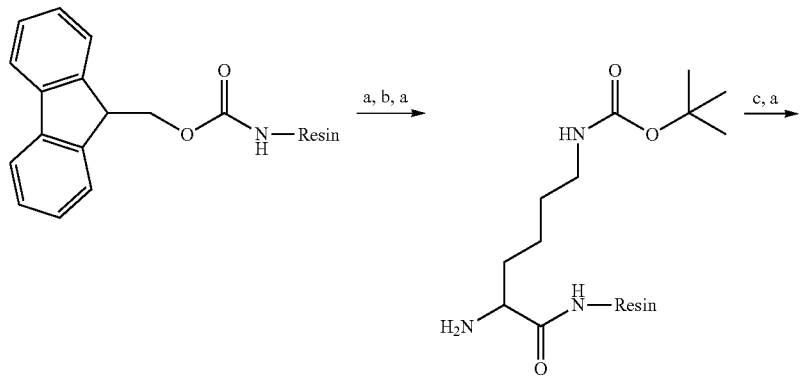

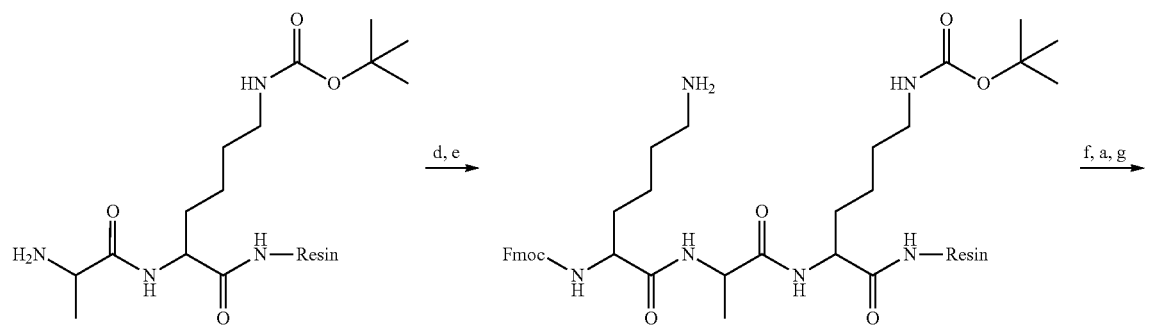
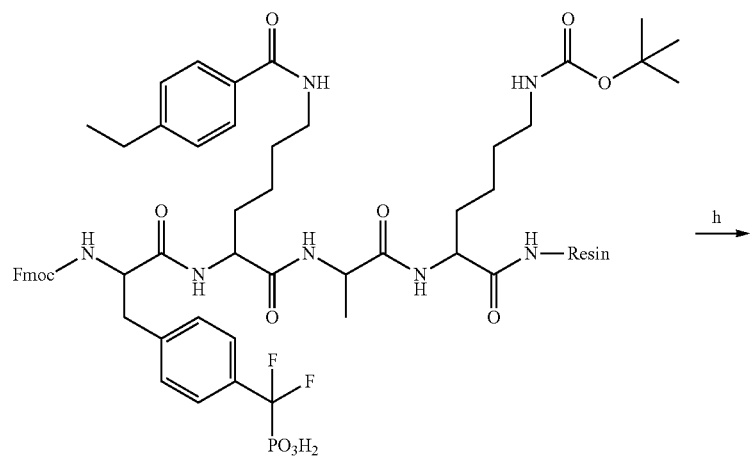
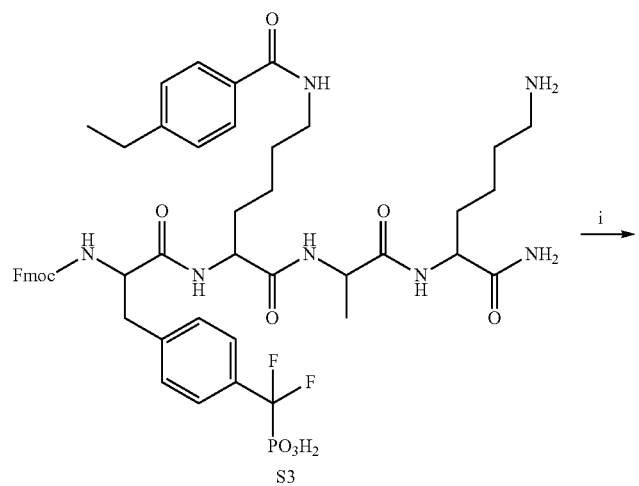

-continued

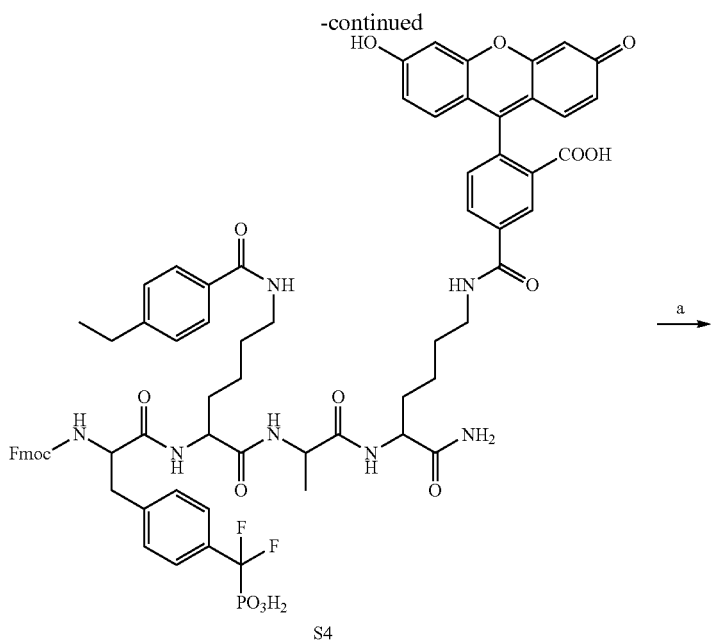

S4

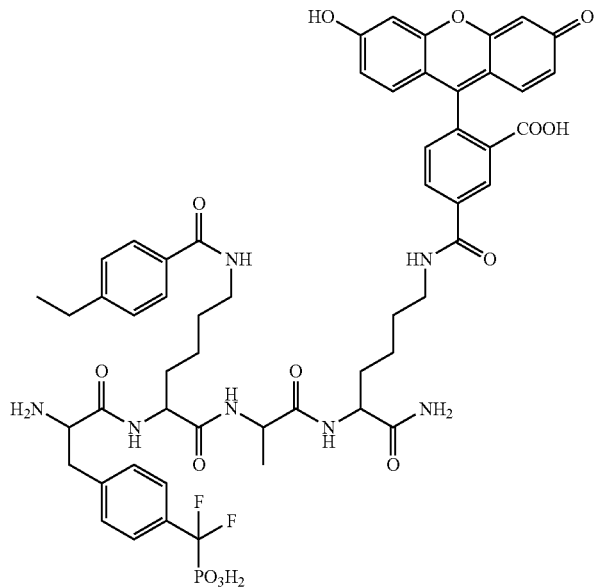

7

(a) 30% piperidine/DMF; (b) Fmoc-Lys(Boc)-OH/HBTU/HOBt/NMM; (c) Fmoc-Ala-OH/HBTU/HOBt/NMM; (d) Fmoc-Lys(Alloc)-OH/HBTU/HOBt/NMM; (e) Tetrakis-(triphenylphosphine)-palladium(0), AcOH/NMM/CH$_2$Cl$_2$; (f) 4-ethylbenzoic acid/HBTU/HOBt/NMM; (g) Fmoc-F$_2$Pmp-OH/HBTU/HOBt/NMM; (h) TFA/H$_2$O/TIS (95:2.5:2.5); (i) 5-(and-6)-carboxyfluorescein, succinimidyl ester/NMM.

Example 5

Synthesis of Compound 8

Compound 8 was synthesized according to Scheme S5, on Rink amide resin (ADVANCED CHEMTECH) using standard Fmoc chemistry. The resin (200 mg, 0.5 mmol/g loading) was activated (general procedure A). The resin was treated with 30% piperidine to remove the Fmoc group (general procedure B). The resin was coupled with Fmoc-Lys(Alloc)-OH (general procedure D). The Alloc group was removed (general procedure C), and resin was coupled 4-ethylbenzoic acid. The Fmoc group was removed and resin was coupled with Fmoc-F$_2$Pmp-OH, Fmoc-Phe-OH and AcOH sequentially. Compound 8 was then cleaved from resin (general procedure E). The crude product purified by HPLC to afford 8 (18.2 mg, 24% yield). Mass calculated for [M] 743. found [M+H]$^+$ 744.

Scheme S5. Synthesis of 8.

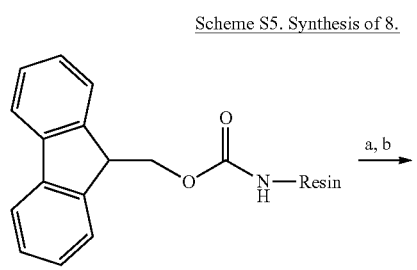

a, b →

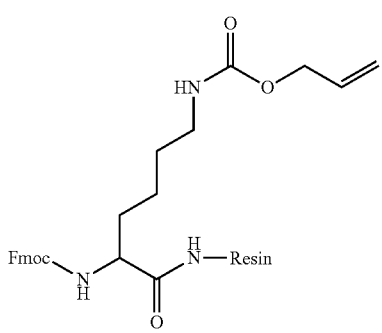

c, d, a, e, a →

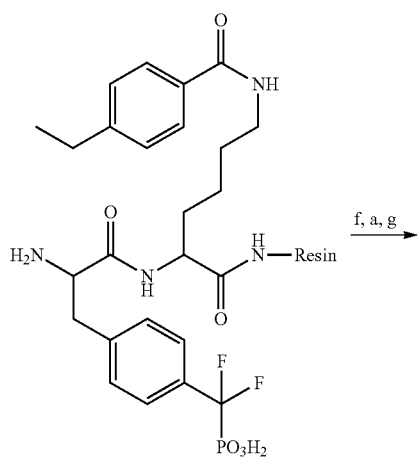

f, a, g →

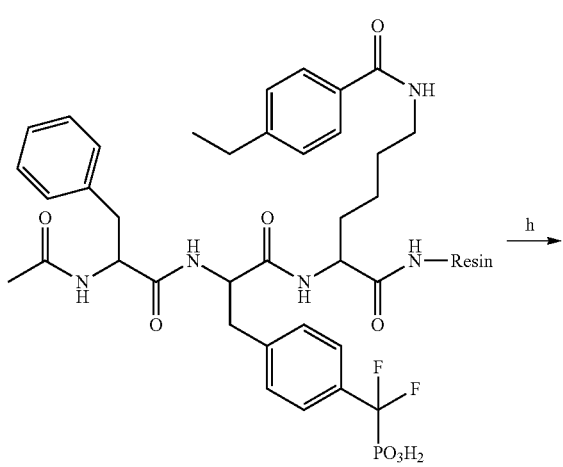

h →

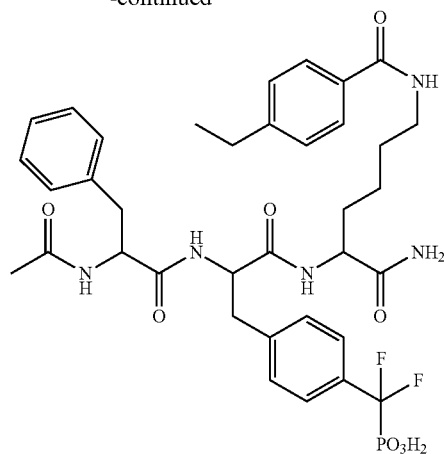

8

(a) 30% piperidine/DMF; (b) Fmoc-Lys(Alloc)-OH/HBTU/HOBt/NMM;
(c) Tetrakis-(triphenylphosphine)-palladium(0), AcOH/NMM/CH$_2$Cl$_2$;
(d) 4-Ethylbenzoic acid/HBTU/HOBt/NMM; (e) Fmoc-F$_2$Pmp-OH/HBTU/HOBt/NMM;
(f) Fmoc-Phe-Oh/HBTU/HOBt/NMM; (g) AcOH/HBTU/HOBt/NMM;
(h) TFA/H$_2$O/TIS (95:2.5:2.5).

Example 6

Synthesis of Precursor 9 for the Third Generation Library

Synthesis of Compound S5.

Compound S5 was synthesized according Scheme S6, on Rink amide resin (ADVANCED CHEMTECH) using standard Fmoc chemistry. The resin (200 mg, 0.5 mmol/g loading) was first activated (general procedure A). Then Fmoc group was removed (general procedure B), and resin was coupled with Fmoc-Lys(Boc)-OH (general procedure D). After removal of Fmoc group, the resin was then sequentially coupled with Fmoc-Ala-OH and Fmoc-Lys(Alloc)-OH. The Alloc group was removed (general procedure C) and resin was coupled with 4-ethylbenzoic acid. The Fmoc group was removed and the resin was the coupled with Fmoc-F$_2$Pmp-OH and Fmoc-Phe-OH sequentially. The compound S5 was then cleaved from resin (general procedure E). The crude product was purified by HPLC to afford S5 (22.4 mg, 20% yield). Mass calculated for [M] 1122. found [M+H]$^+$ 1123.

Synthesis of Compound S6.

Compound S5 (22.4 mg) was treated with 5(6)-FAM SE (20 mg) and NMM (0.1 mL) in DMF (5 mL) overnight. After evaporation of solvents, the crude product was purified by reversed-phase HPLC to afford S6 (10.6 mg, 36% yield). Mass calculated for [M] 1480. found [M+H]$^+$ 1481.

Synthesis of Compound 9.

Compound S6 (10.6 mg) was treated with 30% piperidine in DMF (10 mL) for 30 min. After evaporation of solvents, the crude product was purified by reversed-phase HPLC to afford 9 (5.9 mg, 65% yield). Mass calculated for [M] 1258. found [M+H]$^+$ 1259.

Scheme S6. Synthesis of the precursor 9 for the third generation library.
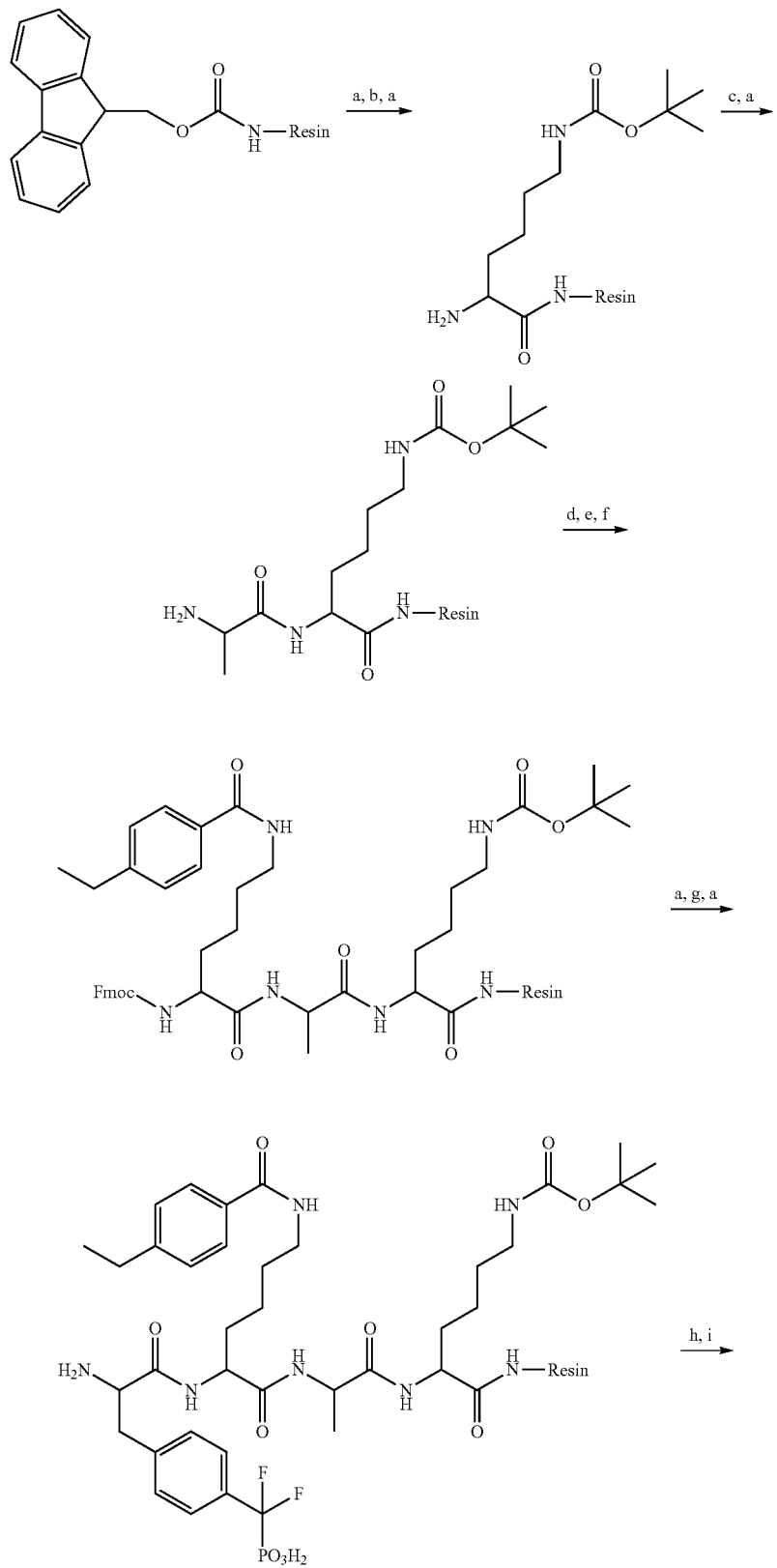

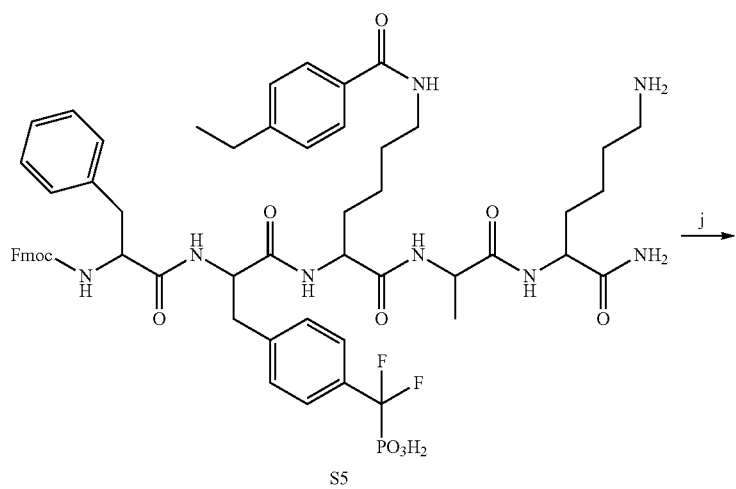
S5
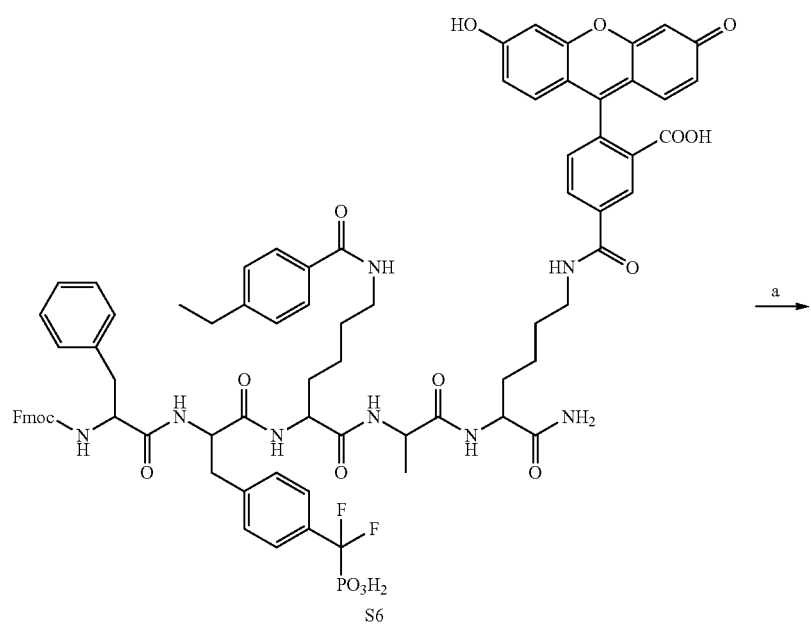
S6

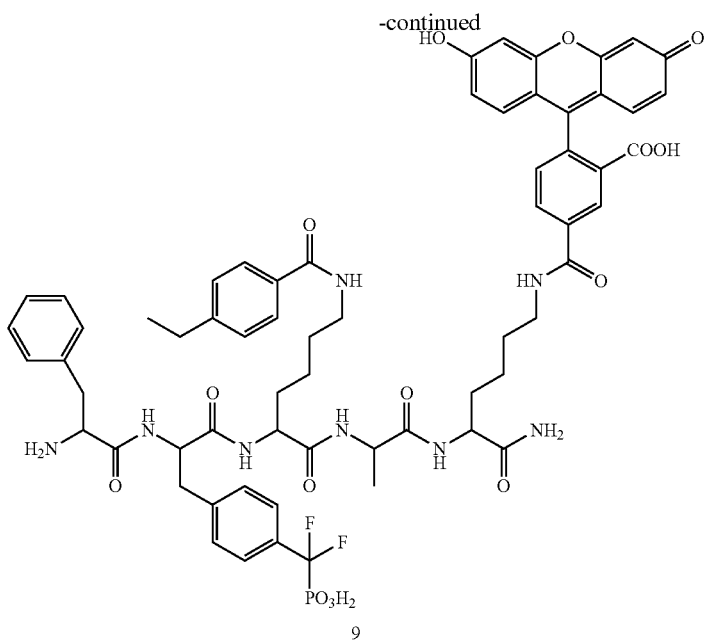

9

(a) 30% piperidine/DMF; (b) Fmoc-Lys(Boc)-OH/HBTU/HOBt/NMM; (c) Fmoc-Ala-OH/HBTU/HOBt/NMM; (d) Fmoc-Lys(Alloc)-OH/HBTU/HOBt/NMM
(e) Tetrakis-(triphenylphosphine)-palladium(0), AcOH/NMM/CH$_2$Cl$_2$; (f) 4-ethylbenzoic acid/HBTU/HOBt/NMM; (g) Fmoc-F$_2$Pmp-OH/HBTU/HOBt/NMM
(h) Fmoc-Phe-OH/HBTU/HOBt/NMM; (i) TFA/H$_2$O/TIS (95:2.5:2.5); (j) 5-(and-6)-carboxyfluorescein, succinimidyl ester/NMM.

Example 7

Synthesis of Compound 10

Compound 10 was synthesized according scheme S7, on Rink amide resin (ADVANCED CHEMTECH) using standard Fmoc chemistry. The resin (200 mg, 0.5 mmol/g loading) was activated (general procedure A). The resin was treated with 30% piperidine to remove the Fmoc group (general procedure B). The resin was coupled with Fmoc-Lys(Alloc)-OH (general procedure D). The Alloc group was removed (general procedure C), and resin was coupled with 4-ethylbenzoic acid. The Fmoc group was removed and resin was sequentially coupled with Fmoc-F$_2$Pmp-OH, Fmoc-Phe-OH and MOA. Compound 10 was then cleaved from resin (general procedure E). The crude product was purified by HPLC to afford 10 (3.8 mg, 4% yield). Mass calculated for [M] 897. found [M+H]$^+$ 898.

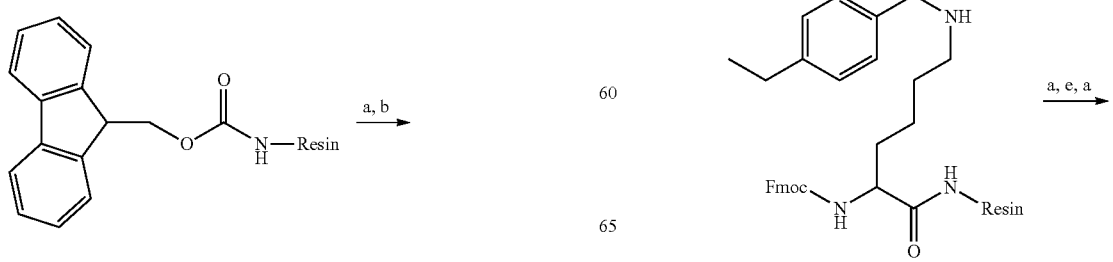

Scheme S7. Synthesis of compund 10.

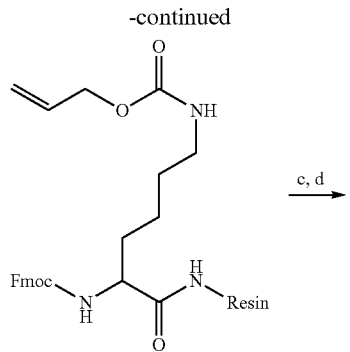

49

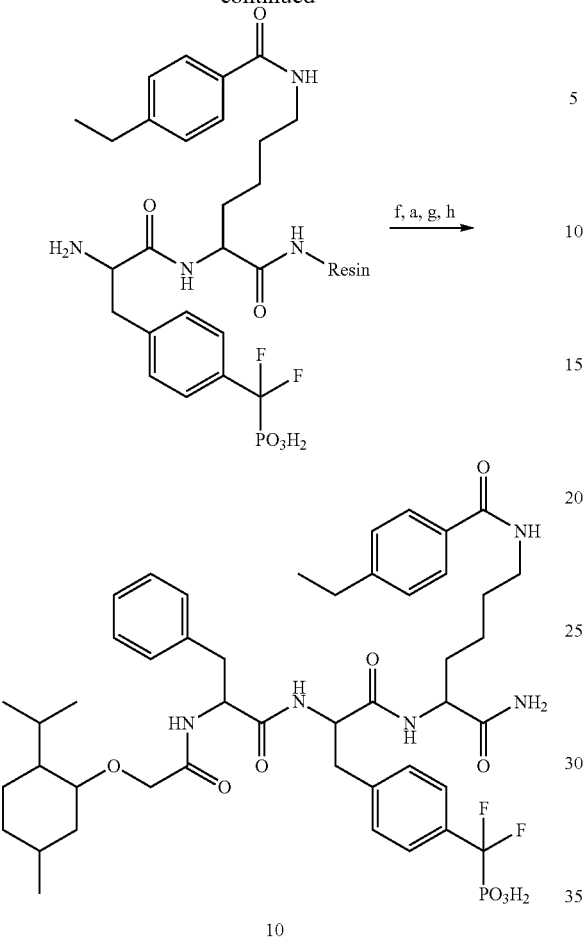

(a) 30% piperidine/DMF; (b) Fmoc-Lys(Alloc)-OH/HBTU/HOBt/NMM;
(c) Tetrakis-(triphenylphosphine)-palladium(0), AcOH/NMM/CH$_2$Cl$_2$;
(d) 4-Ethylbenzoic acid/HBTU/HOBt/NMM; (e) Fmoc-F$_2$Pmp-OH/HBTU/HOBt/NMM;
(f) Fmoc-Phe-OH/HBTU/HOBt/NMM; (g) MOA/HBTU/HOBt/NMM (h) TFA/H$_2$O/TIS (95:2.5:2.5).

Example 8

Synthesis of Compound 11

Compound 11 was synthesized according scheme S8, on Rink amide resin (ADVANCED CHEMTECH) using standard Fmoc chemistry. The resin (200 mg, 0.5 mmol/g loading) was activated (general procedure A). The resin was treated with 30% piperidine to remove the Fmoc group (general procedure B). The resin was coupled with Fmoc-Lys(Alloc)-OH (general procedure D). The Alloc group was removed (general procedure C), and resin was coupled with 4-ethylbenzoic acid. The Fmoc group was removed and resin was sequentially coupled with Fmoc-Phe-OH, Fmoc-Phe-OH and MOA. Compound 11 was then cleaved from resin (general procedure E). The crude product was purified by HPLC to afford 11 (13.6 mg, 18% yield). Mass calculated for [M] 767. found [M+H]$^+$ 768.

50

Scheme S8. Synthesis of 11.

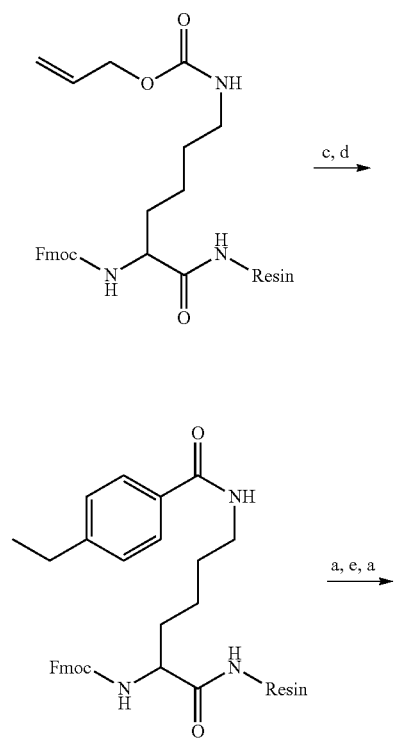

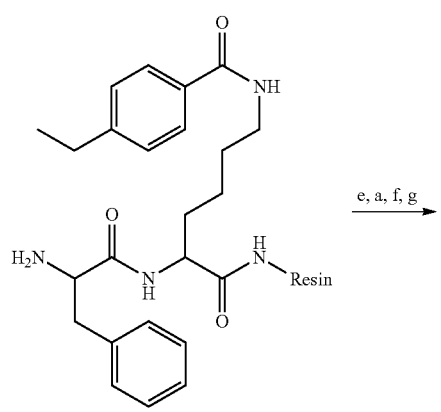

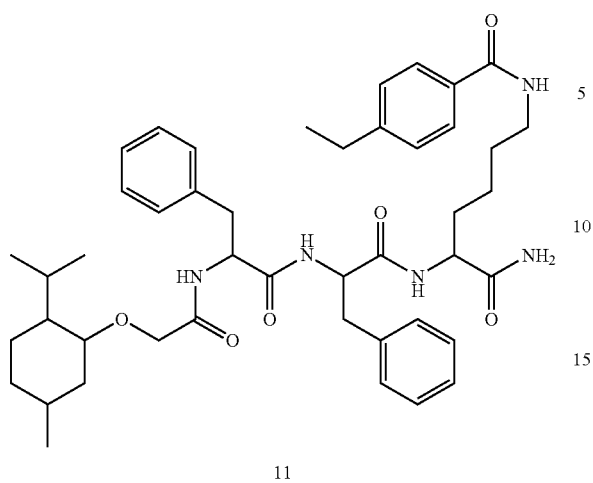
11
(a) 30% piperidine/DMF; (b) Fmoc-Lys(Alloc)-OH/HBTU/HOBt/NMM;
(c) Tetrakis-(triphenylphosphine)-palladium(0), AcOH/NMM/CH$_2$Cl$_2$;
(d) 4-Ethylbenzoic acid/HBTU/HOBt/NMM; (e) Fmoc-Phe-OH/HBTU/HOBt/NMM;
(f) MOA/HBTU/HOBt/NMM; (g) TFA/H$_2$O/TIS (95:2.5:2.5).
Additional examples of compounds synthesized include the following chemical structures:
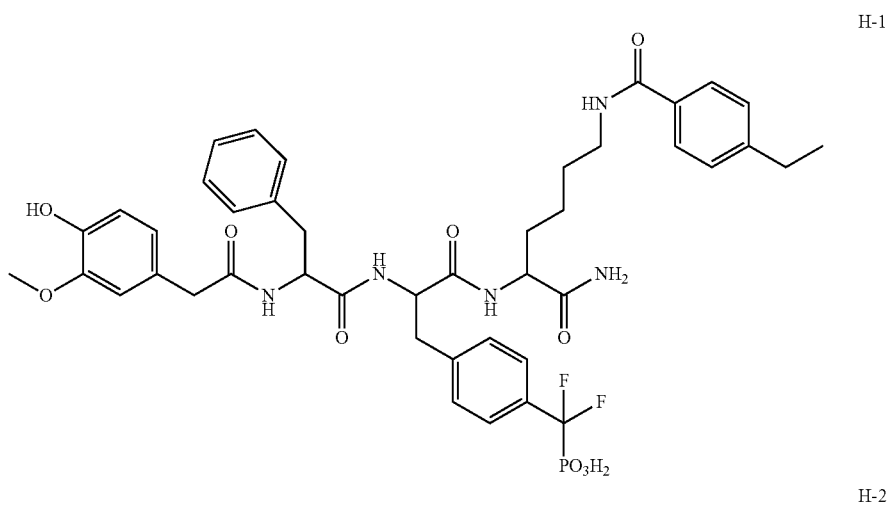
H-1
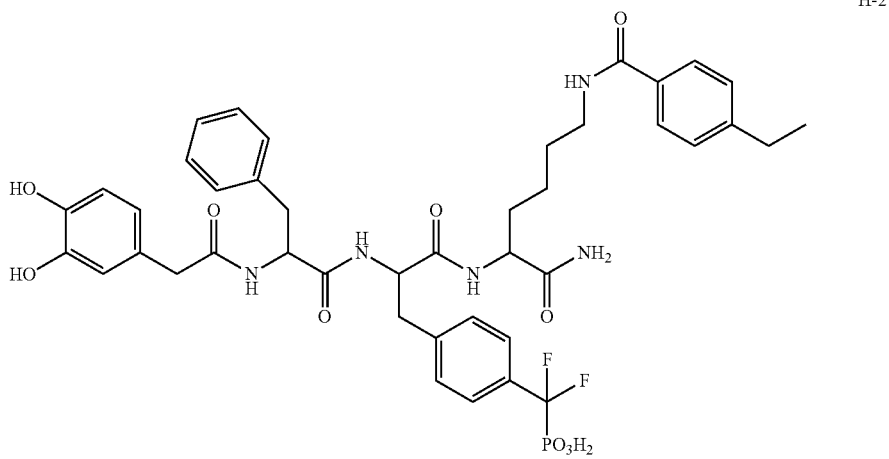
H-2

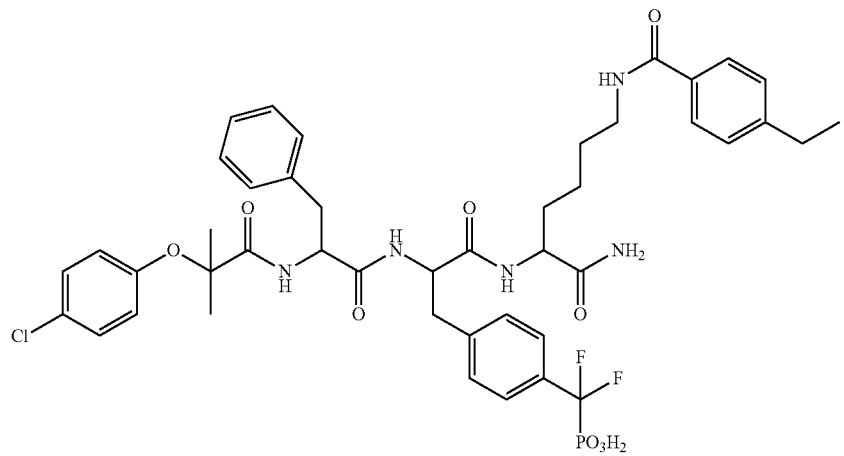

H-3

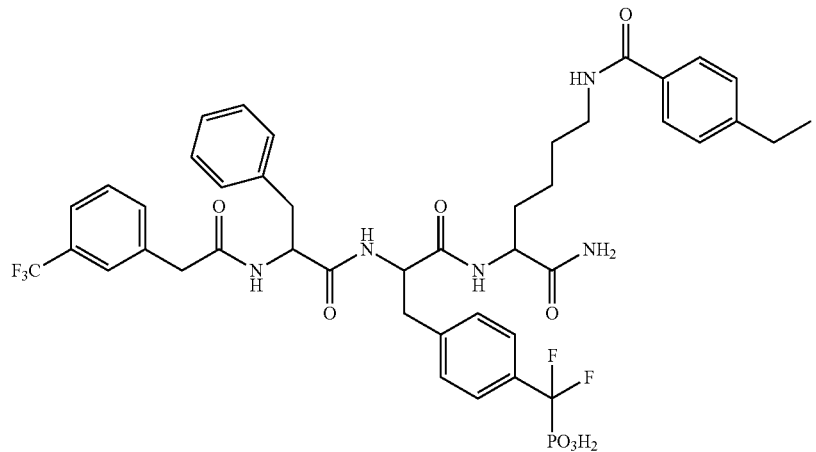

H-4

Example 9

Procedures for Library Preparation

In general, the library was prepared using the TECAN EVO workstation with a 96-channel tip block using disposable tips. The detailed procedure is as following: The 576 different carboxylic acids (40 mM, 10 μL) in DMF were placed in six 96-well plates. HBTU (35 mM, 10 μL), HOBt (50 mM, 10 μL) and NMM (200 mM, 10 μL) were sequentially added to each well of these plates. The library precursor (1-2 mM in DMF, 10 μL) was added to each well. The reaction was quenched after one hour with cyclohexylamine (87 mM in DMF, 10 μL). At last, 190 μL DMSO was added to each well, and the library was then stored in freezer and ready for screen.

Preparation of the 1$^{st}$ Generation Library.

The 1$^{st}$ generation library was prepared using the general procedure, with compound 5 (2 mM) as library precursor.

Preparation of the 2$^{nd}$ Generation Library.

The 2$^{nd}$ generation library was prepared using the general procedure, with compound 7 (1 mM) as library precursor.

Preparation of the 3$^{rd}$ Generation Library.

The 3$^{rd}$ generation library was prepared using the general procedure, with compound 9 (1 mM) as library precursor.

Example 10

Fluorescence Polarization (FP)-Based Screening

Screening of the First Library.

In general, the library was screened using the TECAN GENESIS workstation with a 96-channel tip block with fixed tips. Before screening, the library compounds were diluted from DMSO stock solution into DMG buffer (50 mM 3,3-dimethylglutarate buffer, pH 7.0, containing 1 mM EDTA with an ionic strength of 0.15 M adjusted by addition of NaCl), resulting a set of six daughter plates with approximately 75 nM concentration of each compound in each well. In the first screen, TCPTP (2 μM in DMG buffer, 50 μL) was dispensed into each well of a 384-well plate, and then 2 μL of the fluorescein-tagged library compounds (75 nM stock) were transferred from four 96-well intermediate plates to the 384-well plate (final compound concentration ~3 nM). The fluorescence polarization value ($A_1$) was measured on an ENVISION 2021 Multilabel Microplate Reader (Perkin Elmer). Then in a second screen, 50 μL of a mixture of 2 μM TCPTP and 500 μM Fmoc-F2Pmp-OH (as a competitor ligand) in DMG buffer was dispensed into each well of another 384-well plate, followed by the addition of 2 μL of the fluorescein tagged library compounds (75 nM in DMG buffer). The fluorescence polarization value ($A_2$) was again measured. A displacement percentage was calculated for each library compound as $(A_1-A_2)/(A_1-A_0)\times 100\%$, where $A_1$ and $A_2$ are the fluorescence anisotropy of each sample in screen 1 and screen 2 respectively, and $A_0$ is the fluorescence anisotropy of free library compounds in DMG buffer. To simplify the calculation, $A_0$ is set to 30. The binding affinity ranking of each compound was determined on the displacement percentage: the smaller the displacement percentage, the higher the binding affinity.

Screening of the Second Library.

The library was screened using the same protocol as the $1^{st}$ generation library, except that 0.4 µM TCPTP and 1.5 mM competitive ligand Fmoc-F$_2$Pmp-OH were used. The library was also screened against PTP1B under the same conditions.

Screening of the Third Library.

The library was screened using the same protocol as the $1^{st}$ generation library, except that 0.5 µM protein and 5 µM compound 8 (as a competitor) were used. The library was also screened against PTP1B using the same protocol. The ratio of the displacement percentage of PTP1B over TCPTP was calculated as used to determine the selectivity ranking: the higher the ratio, the better the selectivity.

Example 11

Determination of Inhibition Constants ($K_i$) and IC$_{50}$ Values

The PTP activity was assayed using p-nitrophenyl phosphate (pNPP) as a substrate in DMG buffer at 25° C. The reaction was initiated by the addition of the enzyme (final concentration at 10 nM) to a reaction mixture (0.2 ml) containing various concentrations of pNPP with or without inhibitors. The reaction rate was measure using a SPECTRAMAX microplate spectrophotometer (Molecular Devices). For the determination of $K_m$, the initial velocity and substrate concentration data were fitted to Michaelis-Menten equation using SIGMAPLOT. For the determination of the inhibition constants ($K_i$) of 10 against TCPTP and PTP1B, the tight binding inhibition equation (Wilson et al., 2007) was used for data fitting. IC$_{50}$ values for 4, 6, 8 against TCPTP and PTP1B were obtained at 2 mM pNPP (the Km concentration) and a range of inhibitor concentrations.

Example 12

Effect of TC-PTP Inhibitor on EGFR Phosphorylation

PTP1B$^{-/-}$ cells were treated with TC-PTP inhibitor at indicated concentration for 2 h before EGF treatment. After EGF treatment (2 ng/ml) for 10 min, cells were lysed in 10 mM HEPES, pH 7.4, 150 mM NaCl, 10% Glycerol, 10 mM sodium phosphate, 10 mM sodium fluoride, 1 mM sodium pervanadate, 1 mM benzamidine, 1% Triton X-100, 10 µg/ml leupeptin, and 5 µg/ml aprotinin. Cell lysates were cleared by centrifugation at 15,000 rpm for 10 min. The lysate protein concentration was estimated using the BCA protein assay kit (PIERCE). To detect EGFR phosphorylation levels, 10 µg of anti-EGFR antibody (CELL SIGNALING, #2232) was added to 1 mg of cell lysate and incubated at 4° C. for 2 h. 20 µl of protein A/G-agarose beads were then added and incubated for another 2 h. After extensive washing, the protein complex was boiled with sample buffer, separated by SDS-PAGE, transferred electrophoretically to PVDF membrane, and immunoblotted with anti-pTyr antibodies (MILLIPORE, #05-1050) followed by incubation with horseradish peroxidase-conjugated secondary antibodies. The blots were developed by the enhanced chemiluminescence technique (ECL kit, AMERSHAM BIOSCIENCES).

Example 13

Selectivity of Compound 10

PTP activity was assayed using p-nitrophenyl phosphate (pNPP) as a substrate in DMG buffer (50 mM DMG, pH 7.0, 1 mM EDTA, 150 mM NaCl, 2 mM DTT, 0.1 mg/mL BSA) at 25° C. The assays were performed in 96-well plates. Normally, to determine the IC$_{50}$ values, the reaction was initiated by the addition of enzyme (final concentration of 10 nM) to a reaction mixture (0.2 mL) containing 2 MM ($K_m$ for the substrate) pNPP with various concentrations of inhibitors. The reaction rate was measured using a Spectra Max Plus 384 Microplate Spectrophotometer (Molecular Devices). For compound 10, the final TC-PTP concentration was 0.04 nM. The reactions were incubated at room temperature for 30 min and quenched with 5N NaOH. The absorbance at 405 nm was read on the SpectraMax Plus 384 Microplate Spectrophotometer. For the reversibility test, the enzyme was incubated with the inhibitor at room temperature for 30 min before pNPP was added to initiate the reaction. The reaction was then incubated at room temperature for 30 min and quenched and read. IC$_{50}$ values determined were the same with or without enzyme preincubation with the inhibitor (8.7±1.4 and 9.2±1.4 nM, respectively). To determine the mode of inhibition, the reactions were initiated by the additional enzyme (final concentration for TC-PTP was 0.4 nM and for PTP1B was 2 nM) to the reaction mixtures (0.2 mL) containing various concentrations of pNPP with different concentrations of the inhibitor. Data were fitted using SigmaPlot Enzyme Kinetics Module (Systat Software, Inc.)

IC$_{50}$ measurements of compound 10 without or with TC-PTP preincubation (30 min) yielding similar results (9.2±1.4 and 8.7±1.4 nM, respectively), suggesting that compound 10 is a reversible TC-PTP inhibitor and does not display slow binding kinetics. Further kinetic analysis (Lineweaver-Burk plots) revealed that the mode of TC-PTP inhibition by compound 10 is competitive with a $K_i$ of 4.3±0.2 nM. Importantly, compound 10 is more than 200-fold selective versus a panel of PTPs including the cytosolic PTPs, SHP2, Lyp, HePTP, PTP-Meg2, and FAP1, the receptor like PTPs, CD45, LAR, and PTPα, the dual specificity phosphatase VHR, VHX and CDC14A, and low molecular weight PTP (Table 3). In addition, an 8-fold selectivity for TC-PTP over its closest homologue PTP1B is observed. Indeed, compound 10 appears to be among is the most potent and selective TC-PTP inhibitors ever described.

TABLE 3

| Selectivity of Compound 10. | |
|---|---|
| PTP | $K_i$(nM) |
| TC-PTP | 4.3 ± 0.2 |
| PTP1B | 34.0 ± 2.8 |
| SHP2 | >1000 |
| He-PTP | >1000 |
| Lyp | >1000 |
| FAP1 | >1000 |
| PTP-Meg2 | >1000 |
| PTPα | >1000 |
| LAR | >1000 |
| CD45 | >1000 |

TABLE 3-continued

Selectivity of Compound 10.

| PTP | $K_i$(nM) |
|---|---|
| Cdc14A | >1000 |
| VHR | >1000 |
| VHX | >1000 |
| LMWPTP | >1000 |

Example 14

Activity of Compound 10 Measured in Eukaryotic Cells

Referring now to FIG. 2. PTP1B$^{-/-}$ mouse embryo fibroblast cells were treated with TC-PTP inhibitor at the indicated concentration for 2 h prior to treating either with or without EGF. After EGF treatment (2 ng/mL) for 10 min, cells were lysed in 10 mM HNEPES, pH 7.4, 250 mM NaCl, 10% Glycerol, 10 mM sodium phosphate, 10 mM sodium fluoride, 1 mM sodium pervanadate, 1 mM benzamidine, 1% Triton X-100, 10 µg/mL leupeptin, and 5 µg/mL aprotinin. Cell lysates were cleared by centrifugation at 15 000 rpm for 10 min. The lysate protein concentration was estimated using the BAC protein assay kit (Pierce). To detect EGFR phosphorylation levels, 10 µg of anti-EGFR antibody (Cell Signaling, #2232) were added to 1 mg of cell lysate and incubated at 4° C. for 2 h. 20 µL of protein A/G-agarose beads were then added and incubated for another 2 hr. After extensive washing, the protein complex was boiled with sample buffer, separated by SDS-PAGE, transferred electrophoretically to a PVDF membrane, and immunoblotted with anti-pTyr antibodies (Millipore, #5-1050) followed by incubation with horseradish peroxidase conjugalated secondary antibodies. The blots were developed by enhanced chemiluminescence technique (ECL kit, Amersham Biosciences).

To study the effect of compound 10 on Src phosphorylation, PTP1B$^{-/-}$ mouse embryo fibroblast cells were grown to 80% confluence before being treated with TC-PTP inhibitor 10 for 2 h. Cells were lysed, and the lysates were cleared by centrifugation at 15 000 rpm for 10 min. 30 µg of total proteins were boiled with sample buffer, separated by SDS-PAGE, transferred electrophoretically to a PVDF membrane, and immunoblotted with anti-pSrc416, anti-pSrc527 antibodies (Invitrogen 44-660G and 44-662G) and antic-Src antibody (Cell Singling Technology #2108) followed by incubation with horseradish peroxidase conjugated secondary antibodies. The blots were developed by the enhanced chemiluminesence technique (ECL kit, Amersham Biosciences).

Figure 2A:
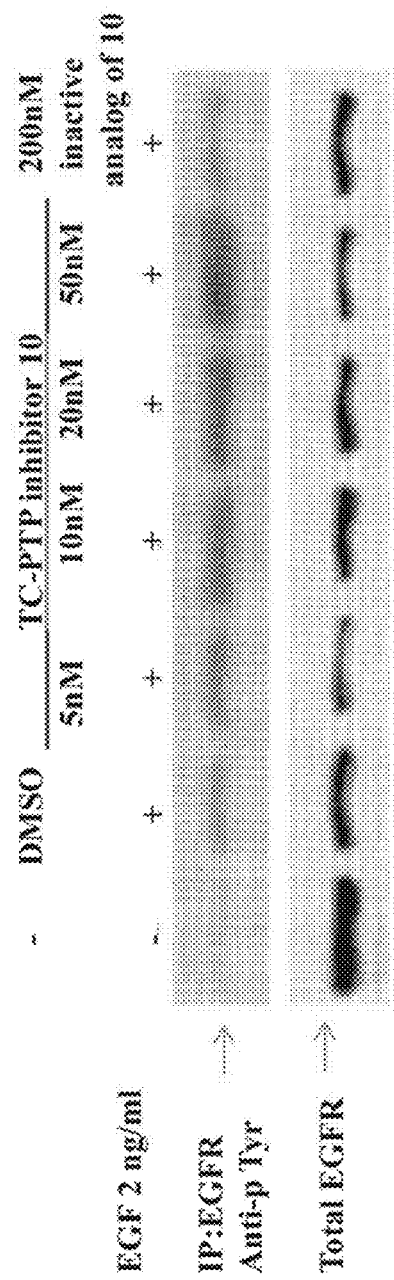
FIG. 2A. Photograph of a Western blot probed with antibody specific for p Tyr.
Figure 2B:
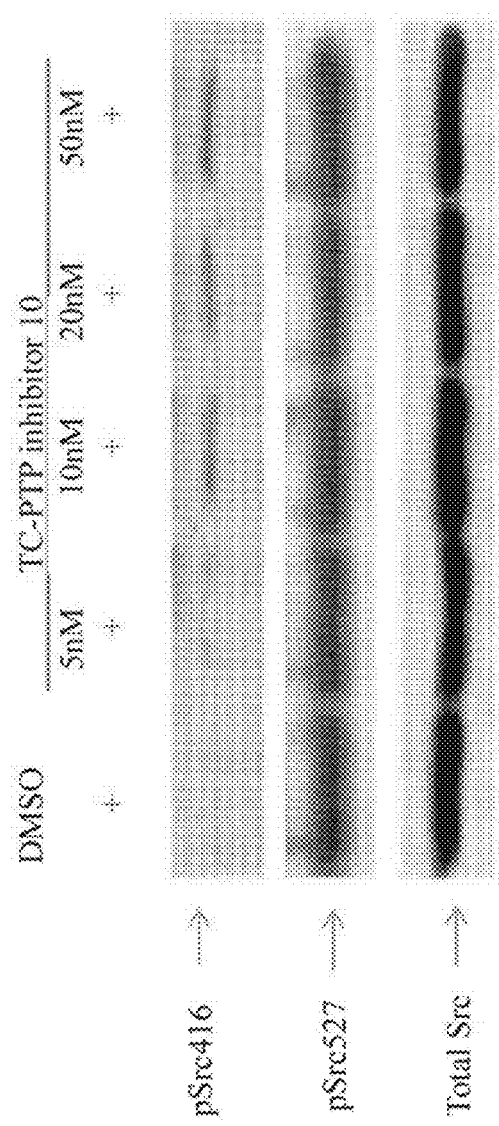
FIG. 2B. Photograph of a Western blot probed with antibody specific for pSrc416 and pSrc 527.

The cellular efficacy of compound 10 was assessed by examining its effect on tyrosine phosphorylation of EGFR, a known substrate of TC-PTP. Referring now to FIG. 2B. PTP1B$^{-/-}$ mouse embryo filbroblast cells were incubated with compound 10 at various concentrations for 2 h and subsequently treated either with or without EGF (2 ng/mL) for 10 min. Inhibition of TC-PTP is expected to enhance endorgenous levels of phosphorylated EGFR. As shown in FIG. 2A, compound 10 enhanced EGFR phosphorylaltion in a dose-dependent fashion relative to DMSO. Remarkably, the phosphorylated form of EGFR is increased nearly 2-fold even at an inhibitor concentration of 5 nM (1.2×$K_i$). The effects are even more pronounced at 10, 20 and 50 nM, with an increase in EGFR phosphorylation of 3.4-, 3.9-, and 5.0-fold, respectively and demonstrate that there is a concentration dependent interaction between compound 10 and the enzyme TC-PTP. These results were in unexpected in view of the general belief that phosphonate-based PTP inhibitors are incapable of penetrating the cell membrane. As a control, a structurally related but inactive analogue of 10 (compound 11) lacking the difluoromethylenephosophonate moiety (IC$_{50}$>1 µM) has no effect on EGFR phosphorylation, even at 200 nM. These results demonstrate that the cellular activity displayed by compound 10 is not due to nonspecific interactions between the compound and TC-PTP (Zhang et al., 2009).

To further investigate the specificity of compound 10 inside the cells, the ability of compound 10 to effect Src kinase phosphorylation within the same cells was measured. Src activity is regulated by phosphorylation at two distinct tyrosine residues. Autophosphorylation of Tyr416 in the kinase domain activates Src, while phosphorylation of Tyr527 in the C-terminal tail by the C-terminal Src kinase (Csk) blocks Src activity. Previous studies have shown that PTP1B can remove the inhibitory phosphate from pSrc527, while TC-PTP is capable of dephosphorylating pSrc416 (van Vilet et al., 2005; Bjorge, et al., 2000). Consistent with these findings, treatment of the cells with TC-PTP inhibitor 10 led to a dose-dependent increase in pSrc416 phosphorylation whereas no significant change in pSrc527, which is not a substrate for TC-PTP, was observed (FIG. 2B). This result supports the conclusion that compound 10 is a selective TC-PTP inhibitor in cells.

Example 15

Effective of Compound 10 on Enzyme Activity in CD4 T-Cells Recovered from Patients with Type 1 Diabetes An increase in expression of TC-PTP type 1 diabetic subject correlates with a decrease in STATS activation (Long et al., 2010). The protein expression levels of STATS, JAK1, JAK3, and the negative regulator, TC-PTP, and CD4 T-cells of control and type 1 diabetic subjects were measured. These results were compared to expression levels of pSTAT5 measured after exposing the cells in vitro to Interleukin 2 (IL-2). No differences were found in STATS, JAK3, or JAK1 protein expression levels between cells from the control group and the group diagnosed with type 1 diabetes. In contrast, TC-PTP expression was uniform in cells recovered from the control group but was increased overall in cells collected from patients with type 1 diabetes. Cells recovered from some patient with type-1 diabetes exhibited a 4-fold greater level of TC-PTP expression than was measured in cells collected from the control group. This increased expression of TC-PTP correlated with decreased levels of pSTAT5 levels measured after exposure to IL-2. These results are consistent with the down modulatory role of TC-PTP in patients with type 1 diabetes.

In cells recovered from patients with type-1 diabetes that exhibited elevated levels of TC-PTP, the decreased response to IL-2 could be rescued in a concentration dependent manner by pre-treating the cells with compound 10. Tests in which TC-PTP, pSTAT5 and FOXP3 persistence were measured in cells recovered from the same individual showed that a type-1 diabetic with elevated TC-PTP expression levels also exhibited reduced levels of pSTAT5 and a reduced persistence of FOXP3 expression. These data suggests that increased expression of TC-PTP and CD4 T-cells in some type 1 diabetic subjects may contribute to reduced level of pSTAT5 in response to IL-2 and that this effect on pSTAT5 levels can be reversed by treating the cells with compound 10.

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety. Those of ordinary skill in the art may readily devise their own implementations and thus fall within the spirit and scope of the present invention.

REFERENCES

Alonso, A.; Sasin, J.; Bottini, N.; Friedberg, I.; Friedberg, I.; Osterman, A.; Godzik, A.; Hunter, T.; Dixon, J.; Mustelin, T. *Cell* 2004, 117, 699-711.
Bjorge, J. D.; Pang, A.; Fujita, D. *J. J Biol. Chem.* 2000, 175, 41439-41446.
Bourdeau, A.; Dube, N.; Tremblay, M. L. *Curr. Opin. Cell Biol.* 2005, 17, 203-209.
Burke, T. R. Jr; Kole, H. K.; Roller, P. P. *Biochem Biophys Res Commun* 1994, 204, 129-134.
Chen, L.; Wu, L.; Otaka, A.; Smyth, M. S.; Roller, P. P.; Burke, T. R. Jr; den Hertog, J.; Zhang, Z. Y. *Biochem Biophys Res Commun* 1995, 216, 976-984.
Elchebly, M.; Payette, P.; Michaliszyn, E.; Cromlish, W.; Collins, S.; Loy, A. L.; Normandin, D.; Cheng, A.; Himms-Hagen, J.; Chan, C.-C.; Ramachandaran, C.; Gresser, M. J.; Tremblay, M. L.; Kennedy, B. P. *Science* 1999, 283, 1544-1548.
Galic, S.; Klingler-Hoffmann, M.; Fodero-Tavoletti, M. T.; Puryer, M. A.; Meng, T. C.; Tonks, N. K.; Tiganis, T. *Mol. Cell. Biol.* 2003, 23, 2096-2108.
Gordeev, M. F.; Patel, D. V.; Barker, P. L.; Gordon, E. M. *Tetrahedron Letters* 1994, 35, 7585-7588.
Klaman, L. D.; Boss, O.; Peroni, O. D.; Kim, J. K.; Martino, J. L.; Zabolotny, J. M.; Moghal, N.; Lubkin, M.; Kim, Y. B.; Sharpe, A. H.; Stricker-Krongrad, A.; Shulman, G. I.; Neel, B. G.; Kahn, B. B. *Mol. Cell. Biol.* 2000, 20, 5479-5489.
Klingler-Hoffmann, M.; Fodero-Tavoletti, M. T.; Mishima, K.; Narita, Y.; Cavenee, W. K.; Furnari, F. B.; Huang, H. J.; Tiganis, T. *J. Biol. Chem.* 2001, 276, 46313-46318.
Lang, F.; Lee, S. Y.; Liang, J.; Lawrence, D. S.; Zhang, Z.-Y. *J Biol. Chem.* 2005, 280, 24857-24863.
Long, A.; Cerogaletti, K.; Bollyky, P.; Tatum, M.; Shilling, H.: Zhang, S.; Zhang, Z.; Pihoker, G.; Sanda, S.; Greenbaum, C.; Buckner, J.; *Diabetes*, Vol. 59, 407-415
Mattila, E.; Pellinen, T.; Nevo, J.; Vuoriluoto, K.; Arjonen, A.; Ivaska, *J. Nat. Cell Biol.* 2005, 7, 78-85.
Qiu, W.; Burton, D. *J. Tetrahedron Letters* 1996, 37, 2745-2748.
Shen, K.; Keng, Y. F.; Wu, L.; Guo, X. L.; Lawrence, D. S.; Zhang, Z. Y. *J. Biol. Chem.* 2001, 276, 47311-47319.
Simoncic, P. D.; Lee-Loy, A.; Barber, D. L.; Tremblay, M. L.; McGlade, C. *J. Curr. Biol.* 2002, 12, 446-453.
Tiganis, T.; Bennett, A. M.; Ravichandran, K. S.; Tonks, N. K. *Mol. Cell. Biol.* 1998, 18, 1622-1634.
Todd, J. A. et al. *Nat. Genet.* 2007, 39, 857-864.
Tonks, N. K. *Nat. Rev. Mol. Cell Biol.* 2006, 7, 833-846.
van Vliet, C.; Bukczynska, P. E.; Puryer, M. A.; Sadek, C. M.; Shields, B. J.; Tremblay, M. L.; Tiganis, T. *Nat. Immunol.* 2005, 6, 253-260.
Wilson, D. P.; Wan, Z. K.; Xu, W. X.; Kirincich, S. J.; Follows, B. C.; Joseph-McCarthy, D.; Foreman, K.; Moretto, A.; Wu, J.; Zhu, M.; Binnun, E.; Zhang, Y. L.; Tam, M.; Erbe, D. V.; Tobin, J.; Xu, X.; Leung, L.; Shilling, A.; Tam, S. Y.; Mansour, T. S.; Lee, J. *J. Med. Chem.* 2007, 50, 4681-4698.
WTCCC (Wellcome Trust Case Control Consortium), *Nature* 2007, 447, 661-678.
Youten, K. E.; Muise, E. S.; Itie, A.; Michaliszyn, E.; Wagner, J.; Jothy, S.; Lapp, W. S.; Tremblay, M. L. *J. Exp. Med.* 1997, 186, 683-693.
van Vliet, C.; Bukczynska, P. E.; Puryer, M. A.; Sadek, C. M.; Shields, B. J.; Tremblay, M. L.; Tiganis, T. *Nat. Immunol.* 2005, 6, 253-260.
Zhang, S.; Chen, L.; Lou, Y.; Gunawan, A.; Lawrence, D.; Zhang, Z.: *J. Am. Chem. Soc.* 2009, 131, 13072-13079.
Zhang, S.; Chen, L.; Kumar, S.; Wu, L.; Lawrence, D. S.; Zhang, Z.-Y. *Methods* 2007, 42, 261-267.
Zhang, Z.-Y. *Curr. Opin. Chem. Biol.* 2001, 5, 416-423.
Zhang, Z.-Y. *Ann. Rev. Pharmacol. Toxicol.* 2002, 42, 209-234.
Zhang, S.; Zhang, Z.-Y. *Drug Discovery Today* 2007, 12, 373-381.

We claim:
1. A method of inhibiting or reducing the activity of a protein tyrosine phosphatase in a human patient, comprising the step of:
administering to a human patient at least one compound having the formula:

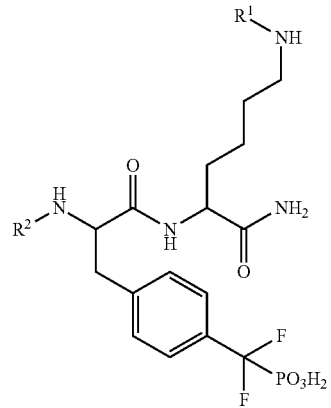

wherein $R^1$ and $R^2$ are the same or different and each individually is a residue of a carboxylic acid, and pharmaceutically acceptable salts thereof, wherein said carboxylic acid is selected from the group consisting of:
3-dimethylaminobenzoic acid, 2-(2-cyanophenylthio) benzoic acid, 2-(4-chlorobenzoyl)benzoic acid, (−)-2-oxo-4-thiazolidine-carboxylic acid, (−)-N-acetyl-neuraminic acid, (+)-6-methoxy-a-methyl-2-naphthaleneacetic acid, (+)-carbobenzyloxy-D-proline, (+)-menthoxyacetic acid, (+)-2-(2-chlorophenoxy)propionic acid, (±)-1-methyl-2-cyclohexene-1-carboxylic acid, (1-naphthoxy)acetic acid, (1R)-(1a,2b,3a)-(+)-3-methyl-2-nitromethyl-5-oxocyclopentaneacetic acid, (1R,4R)-7,7-dimethyl-2-oxobicyclo[2.2.1]heptane-1-carboxylic acid, (1S)-(+)-camphanic acid, (1S,3R,4S,5R)-1,3,4,5-tetrahydroxycyclohexanecarboxylic acid, (2,4-di-tert-pentylphenoxyl)acetic acid, (2-naphthoxy)acetic acid, (2-pyrimidylthio)acetic acid, (4-carboxybutyl)triphenyl-phosphonium bromide, (4-chlorophenylthio)acetic acid, (4-methylphenoxy)acetic acid, (a,a,a-trofluoro-m-tolyl)acetic acid, (E)-2-((4-hydroxyphenyl)diazenyl)benzoic acid, (E)-2-methyl-3-(2,4,5-trimethoxyphenyflacrylic acid, (methylthio)acetic acid, (R)-(−)-2-hydroxy-4-phenylbutyric acid, (R)-(−)-3-chloromandelic acid, (R)-(−)-hexahydromandelic acid, (R)-(+)-2-pyrrolidone-5-carboxylic acid, (R)-(+)-citronellic acid, (R)-2-(1-phenylethylcarbamoyl)benzoic acid, (R)-2-hydroxy-2-phenylacetic acid, (R)-3,3,3-trifluoro-2-methoxy-2-phenylpropanoic acid, (R)-6-hydroxy-2,5,7,8-tetramethylchroman-2-carboxylic acid, (S)-(−)-indoline-2-carboxylic acid, (S)-(+)-2-oxo-4-phenyl-3-oxazolidineacetic acid, (S)-(+)-5-oxo-2-tetrahydro-furancarboxylic acid, (S)-(+)-hexahydromandelic acid, (S)-(+)-N-[1-(1-naphthyl)-ethyl]-phthalamic acid, (S)-(+)-O-acetylmandelic acid, (S)-2-(1-phenylethylcarbamoyl)benzoic acid, (S)-2-(4-isobutylphenyl)propanoic acid, (S)-2-(phenylcarbamoyloxy)propanoic acid, (S)-3-(benzyloxycarbonyl)-2-oxoimidazolidine-4-carboxylic acid, (S)-3,3,3-trifluoro-2-methoxy-2-phenylpropanoic acid, (S)-3,3,3-trifluoro-2-methoxy-2-phenylpropanoic acid, (S)-6-methoxy-2,5,7,8-tetramethylchroman-2-carboxylic acid, (trimethylsilyl)acetic acid, (z)-2-cyano-3-(3-hydroxyphenyl)acrylic acid, 1-(4-chlorophenyl)-1-cyclopentanecarboxylic acid, 1-(tert-butyl)hydrocinnamic acid, 1,2-phenylenedioxydiacetic acid, 1,4-dihydro-2-methylbenzoic acid, 1,4-dihydroxy-2-naphthoic acid, 10-hydroxydecanoic acid, 10-undecynoic acid, 1-admantanecarboxylic acid, 1-cyano-1-cyclopropane-carboxylic acid, 1-hydroxy-2-naphthoic acid, 1-isoquinolinecarboxylic acid, 1-methyl-(1S,2R)-(+)-cis-1,2,3,6-tetrahydrophthalate, 1-methyl-1-cyclohexane-carboxylic acid, 1-methyl-1H-indole-2-carboxylic acid, 1-methyl-2-pyrrolecarboxylic acid, 1-methylcyclopropane-carboxylic acid, 1-naphthoic acid, 1-phenyl-1-cyclopentane-carboxylic acid, 1-phenyl-1-cyclopropane-carboxylic acid, 1-pyreneacetic acid, 1-pyrenebutyric acid, 1-pyrenecarboxylic acid, 2-((1R,2R,3R,4S)-3-hydroxy-4,7,7-trimethylbicyclo[2.2.1]heptan-2-yl)acetic acid, 2-((benzyloxycarbonyl)(methyl)amino)-2-methylpropanoic acid, 2-(2,(trifluoromethyl)phenyl)acetic acid, 2-(2,4,5-trichlorophenoxy)-propionic acid, 2-(2,4-dichlorophenoxy)-propionic acid, 2-(3,5-dinitrobenzamido)-2-phenylacetic acid, 2-(3,5-dinitrobenzamido)-4-methylpentanoic acid, 2-(3-chlorophenoxy)propionic acid, 2-(4-(trifluoromethyl)phenyl)acetic acid, 2-(4-chloro-3-nitrobenzoyl)-benzoic acid, 2-(4-chlorophenoxy)-2-methyl-propionic acid, 2-(4-chlorophenoxy)propionic acid, 2-(4-fluorobenzoyl)benzoic acid, 2-(4-hydroxy-3-methoxyphenyl)acetic acid, 2-(4-hydroxyphenoxy)-propionic acid, 2-(4-isobutylphenyl)propanoic acid, 2-(4-nitrophenyl)propionic acid, 2-(benzyloxycarbonylamino)-3-(1H-indol-3-yl)propanoic acid, 2-(trifluoromethyl)acrylic acid, 2-(trifluoromethyl)benzoic acid, 2-(trifluoromethyl)cinnamic acid, 2,2,3,3-tetramethyl-cyclopropanecarboxylic acid, 2,2-bis(hydroxymethyl)-propionic acid, 2,3,4,5,6-pentafluoro-cinnamic acid, 2,3,4,5,6-pentafluorophenoxy acetic acid, 2,3,4,5,6-pentafluorophenyl-acetic acid, 2,3,4,5-tetrafluorobenzoic acid, 2,3,4-trifluorocinnamic acid, 2,3,4-trihydroxybenzoic acid, 2,3,4-trimethoxybenzoic acid, 2,3,5,6-tetrafluoro-4-hydr-oxy-benzoic acid hydrate, 2,3,5,6-tetrafluorobenzoic acid, 2,3,5,6-tetrafluoro-p-toluic acid, 2,3,5-triiodobenzoic acid, 2,3,6-trifluorobenzoic acid, 2,3-dichlorobenzoic acid, 2,3-difluorobenzoic acid, 2,3-dihydroxybenzoic acid, 2,3-dimethylbenzoic acid, 2,4,5-trichlorophenoxyacetic acid, 2,4,5-trimethoxybenzoic acid, 2,4,6-trichlorobenzoic acid, 2,4,6-trifluorobenzoic acid, 2,4,6-trihydroxybenzoic acid monohydrate, 2,4,6-trimethylbenzoic acid, 2,4-bis(trifluoromethyl)-benzoic acid, 2,4-dichloro-5-fluorobenzoic acid, 2,4-dichloro-5-sulfamoyl-benzoic acid, 2,4-dichlorobenzoic acid, 2,4-dichlorophenylacetic acid, 2,4-difluorobenzoic acid, 2,4-difluorophenylacetic acid, 2,4-dihydroxybenzoic acid, 2,4-dimethylbenzoic acid, 2,4-dinitrobenzoic acid, 2,4-dinitrophenylacetic acid, 2,4-hexadienoic acid, 2,5-bis(trifluoromethyl)-benzoic acid, 2,5-dichlorobenzoic acid, 2,5-difluorobenzoic acid, 2,5-difluorophenylacetic acid, 2,5-dihydroxybenzoic acid, 2,5-dihydroxyphenylacetic acid, 2,5-dimethoxybenzoic acid, 2,5-dimethoxycinnamic acid, 2,6-dichloro-3-nitrobenzoic acid, 2,6-difluorobenzoic acid, 2,6-difluorophenylacetic acid, 2,6-dihydroxybenzoic acid, 2,6-dimethoxynicotinic acid, 2,6-dimethylbenzoic acid, 2,6-heptadienoic acid, 2-[4-(dibutylamino)-2-hydroxybenzoyl]benzoic acid, 2-bibenzylcarboxylic acid, 2-biphenylcarboxylic acid, 2-bromo-3-nitrobenzoic acid, 2-bromo-4,5-dimethoxybenzoic acid, 2-bromo-5-methoxybenzoic acid, 2-bromo-5-nitrobenzoic acid, 2-bromoacrylic acid, 2-bromophenylacetic acid, 2-chloro-3-nitrobenzoic acid, 2-chloro-4,5-difluorobenzoic acid, 2-chloro-4-fluorobenzoic acid, 2-chloro-5-(methylthio)-benzoic acid, 2-chloro-5-(trifluoro-methyl)benzoic acid, 2-chloro-5-nitrobenzoic acid, 2-chloro-5-nitrocinnamic acid, 2-chloro-6-fluorobenzoic acid, 2-chloro-6-fluorophenylacetic acid, 2-chloro-6-methylnicotinic acid, 2-chlorobenzoic acid, 2-chloronicotinic acid, 2-chlorophenylacetic acid, 2-chloropropionic acid, 2-ethoxy-1-naphthoic acid, 2-ethoxybenzoic acid, 2-ethyl-2-hydroxybutyric acid, 2-ethylbutyric acid, 2-ethylhexanoic acid, 2-ethylthio-2,2-diphenyl-acetic acid, 2-fluoro-3-(trifluoromethyl)-benzoic acid, 2-fluoro-4-(trifluoromethyl)-benzoic acid, 2-fluoro-5-methylbenzoic acid, 2-fluoro-5-nitrobenzoic acid, 2-fluoro-6-(trifluoromethyl)-benzoic acid, 2-fluorobenzoic acid, 2-fluorocinnamic acid, 2-fluorophenylacetic acid, 2-hydroxy-3-isopropyl-6-methylbenzoic acid, 2-hydroxy-3-isopropylbenzoic acid, 2-hydroxy-3-methylbutyric acid, 2-hydroxy-6-isopropyl-3-methylbenzoic acid, 2-hydroxycaproic acid, 2-hydroxyhippuric acid, 2-hydroxyisobutyric acid, 2-hydroxyisobutyric acid, 2-hydroxynicotinic acid, 2-hydroxyphenylacetic acid, 2-iodobenzoic acid, 2-mercaptonicotinic acid, 2-methoxy-2-phenylacetic acid, 2-methoxy-4-(methylthio)-benzoic acid, 2-methoxy-4-nitrobenzoic acid, 2-methoxyphenylacetic acid, 2-methyl-1-cyclohexane-carboxylic acid (cis and trans), 2-methyl-3-nitrobenzoic acid, 2-methyl-3-phenylpropanoic acid, 2-methyl-4-oxo-4-phenylbutyric acid, 2-methyl-6-nitrobenzoic acid, 2-methylbutyric acid, 2-methylcinnamic acid, 2-methylcyclopropane-carboxylic acid (cis&trans), 2-methylhexanoic acid, 2-methylhippuric acid, 2-methylhydrocinnamic acid, 2-methylvaleric acid, 2-naphthoic acid, 2-naphthylacetic acid, 2-nitro-4-(trifluoromethyl)benzoic acid, 2-nitrobenzoic acid, 2-norbornaneacetic acid, 2-oxo-6-pentyl-2H-pyran-3-carboxylic acid, 2-phenoxybenzoic acid, 2-phenoxybutyric acid, 2-phenoxypropionic acid, 2-propylpentanoic acid, 2-quinoxalinecarboxylic acid, 2-thiopheneacetic acid, 2-thiopheneacetic acid, 2-thiopheneglyoxylic acid, 3-(2-hydroxyphenyl)propionic acid, 3-(2-thienyl) acrylic acid, 3-(3,4,5-trimethoxyphenyl)-propionic acid, 3-(3,4-dimethoxyphenyl)-propionic acid, 3-(3-hydroxy-2,4,6-triiodophenyl)pentanoic acid, 3-(3-hydroxyphenyl)-propionic acid, 3-(3-methoxyphenyl) propionic acid, 3-(4-chlorobenzoyl)propionic acid, 3-(4-chlorobenzoyl)propionic acid, 3-(4-chlorobenzoyl)propionic acid, 3-(4-fluorobenzoyl)propionic acid, 3-(4-hydroxyphenyl)propionic acid, 3-(phenylsulfonyl)propionic acid, 3-(trifluoromethyl)cinnamic acid, 3-(trimethylsilyl)propynoic acid, 3,3,3-triphenyl-propionic acid, 3,4-(methylenedioxy)cinnamic acid, 3,4-(methylenedioxy)phenyl-acetic acid, 3,4-dichlorobenzoic acid, 3,4-dichlorophenoxyacetic acid, 3,4-diethoxybenzoic acid, 3,4-difluorobenzoic acid, 3,4-dihydroxybenzoic acid, 3,4-dihydroxyhydrocinnamic acid, 3,4-dihydroxyphenylacetic acid, 3,5,6-trichlorosalicylic acid, 3,5-bis(trifluoromethyl)-phenyl acetic acid, 3,5-dibromobenzoic acid, 3,5-dichlorosalicyclic acid, 3,5-difluorocinnamic acid, 3,5-dihydroxy-2-naphthoic acid, 3,5-dinitrobenzoic acid, 3,5-dinitro-o-tuluic acid, 3,5-dinitro-p-toluic acid, 3,5-dinitrosalicyclic acid, 3,5-di-tert-butyl-4-hydroxy-benzoic acid, 3,5-di-tert-butylbenzoic acid, 3,7-dihydroxy-2-naphthoic acid, 3,thiopheneacetic acid, 3-benzoyl-2-pyridine-carboxylic acid, 3-benzoylbenzoic acid, 3-bromo-4-fluorobenzoic acid (95%), 3-bromo-4-methylbenzoic acid, 3-bromo-5-iodobenzoic acid, 3-bromobenzoic acid, 3-bromocinnamic acid, 3-carboxy-PROXYL, 3-chloro-2-nitrobenzoic acid, 3-chloro-4-fluorobenzoic acid, 3-chloro-4-hydroxyphenyl-acetic acid, 3-chlorosalicylic acid, 3-cyanobenzoic acid, 3-fluoro-2-methylbenzoic acid, 3-fluoro-4-hydroxy-phenylacetic acid, 3-fluoro-4-methoxybenzoic acid, 3-fluorophenylacetic acid, 3-furoic acid, 3-hydroxy-2-naphthoic acid, 3-hydroxy-2-quinoxaline-carboxylic acid, 3-hydroxy-4-methoxybenxoic acid, 3-hydroxy-4-methoxy-cinnamic acid, 3-hydroxy-4-nitrobenzoic acid, 3-hydroxybenzoic acid, 3-hydroxybutyric acid, 3-hydroxyphenylacetic acid, 3-indolebutyric acid, 3-indoleglyoxylic acid, 3-indolepropionic acid, 3-iodo-4-methylbenzoic acid, 3-iodobenzoic acid, 3-isoquinolinecarboxylic acid hydrate, 3-methoxy-4-nitrobenzoic acid, 3-methoxycyclohexane-carboxylic acid (cis&trans), 3-methyl-2-phenylvaleric acid, 3-methylhippuric acid, 3-methylindene-2-carboxylic acid, 3-methylsalicylic acid, 3-methyl valeric acid, 3-nitreobenzoic acid, 3-nitrophenylacetic acid, 3-nitropropionic acid, 3-noradamantanecarboxylic acid, 3-oxo-1-indancarboxylic acid, 3-phenoxybenzoic acid, 3-phenylbutyric acid, 3-p-tolylpropanoic acid, 3-thiophenecarboxylic acid, 4-(1,3-dioxoisoindolin-2-yl)-2-hydroxybutanoic acid, 4-(2,4,5-trichlorophenoxy)-butyric acid, 4-(2,4-dichlorophenoxy)-butyric acid, 4-(2,4-di-tert-pentylphenoxy)butyric acid, 4-(2-phenoxyethoxy) benzoic acid, 4-(3,4-dimethoxyphenyl)-butyric acid, 4-(4-methoxyphenyl)butyric acid, 4-(4-nitrophenyl)butyric acid, 4-(diethylamino)benzoic acid, 4-(dimethylamino)cinnamic acid, 4-(dimethylamino)phenyl-acetic acid, 4-(ethylthio)benzoic acid, 4-(hydroxymethyl)benzoic acid, 4-(methylsulfonyl)benzoic acid, 4-(methylthio)benzoic acid, 4-(methylthio)phenylacetic acid, 4-(trifluoromethoxy)benzoic acid, 4'-(trifluoromethyl) biphenyl-2-carboxylic acid, 4-(trifluoromethyl)mandelic acid, 4,4,4-trifluoro-3-methyl-2-butenoic acid, 4,4-bis(4-hydroxyphenyl)-valeric acid, 4,5-dimethoxy-2-nitrobenzoic acid, 4,6-dioxoheptanoic acid, 4-[4-(2-carboxybenzoyl)-phenyl]butyric acid, 4-acetamidobenzoic acid, 4-acetylbenzoic acid, 4-acetylphenoxyacetic acid, 4-benzyloxy-3-methoxyphenyl-acetic acid, 4-biphenylacetic acid, 4-bromo-3,5-dihydroxy-benzoic acid, 4-bromobenzoic acid, 4-bromocinnamic acid, 4-bromophenylacetic acid, 4-butoxybenzoic acid, 4-butoxyphenylacetic acid, 4-butylbenzoic acid, 4-chloro-2,5-difluorobenzic acid, 4-chloro-3-sulfamoylbenzoic acid, 4-chlorobenzoic acid, 4-chloro-o-tolyloxyacetic acid, 4-chlorophenylacetic acid, 4-chlorosalicylic acid, 4-ethoxycarbonyloxy-3,5-dimethoxybenzoic acid, 4-ethoxyphenylacetic acid, 4-ethylbenzoic acid, 4'-ethylbiphenyl-4-carboxylic acid, 4-fluorenecarboxylic acid, 4-fluoro-1-naphthoic acid, 4-fluoro-2-(trifluoromethyl)-benzoic acid, 4-fluoro-3-nitrobenzoic acid, 4-fluorobenzoic acid, 4-fluorobenzoic acid, 4-fluorocinnamic acid, 4-fluorophenoxyacetic acid, 4-heptyloxybenzoic acid, 4-hexylbenzoic acid, 4-hexyloxybenzoic acid, 4-hydroxy-3-(morpholino-methyl)benzoic acid hydrate, 4-hydroxy-3,5-dinitrobenzoic acid, 4-hydroxy-3-methoxy-benzoic acid, 4-hydroxy-3-methoxy-mandelic acid, 4-hydroxy-3-nitrobenzoic acid, 4-hydroxy-3-nitrophenylacetic acid, 4-hydroxybenzoic acid, 4'-hydroxybiphenyl-4-carboxylic acid, 4-hydroxyphenylacetic acid, 4-hydroxyphenylacetic acid, 4-hydroxyphenylpyruvic acid, 4-iodobenzoic acid, 4-isopropoxybenzoic acid, 4-methoxy-3-nitrobenzoic acid, 4-methoxycyclohexane-carboxylic acid, 4-methoxysalilcylic acid, 4-methyl-1-cyclohexane-carboxylic acid (cis and trans), 4-methyl-3-nitrobenzoic acid, 4-methylhippuric acid, 4-methylsalicyclic acid, 4-methylvaleric acid, 4-nitro-3-pyrazolecarboxylic acid, 4-nitrohippuric acid, 4-nonyloxybenzoic acid, 4-Octylbenoic acid, 4-oxo-4H-1-benzopyran-2-carboxylic acid, 4-oxo-6-phenyl-5-hexenoic acid, 4-pentenoic acid, 4-pentylbenzoic acid, 4-pentylbicyclo[2.2.2]octane-1-carboxylic acid, 4-pentyloxybenzoic acid, 4-pentynoic acid, 4-phenylbutyric acid, 4-Propoxybenzoic acid, 4-propylbenzoic acid, 4-pyrazolecarboxylic acid, 4-tert-butylbenzoic acid, 4-tert-butylcyclohexanecarboxylic acid, 4-Vinylbenzoic acid, 5-(4-chlorophenyl)-2-furoic acid, 5,6-dichloronicotinic acid, 5-bromo-2,4-dihydroxybenzoic acid, 5-fluoro-2-methylbenzoic acid, 5-fluoroindole-2-carboxylic acid, 5-fluorosalicylic acid, 5-hydantoinacetic acid, 5-hydroxy-2-indole-carboxylic acid, 5-methoxy-1-indanone-3-acetic acid, 5-methoxy-2-methyl-3-indoleacetic acid, 5-methoxy-2-nitrobenzoic acid, 5-methoxysalicylic acid, 5-methyl-2-nitrobenzoic acid, 5-methyl-2-pyrazine-carboxylic acid, 5-nitro-2-furoic acid, 5-nitro-3-pyrazolecarboxylic acid, 5-phenyl valeric acid, 6-(carbobenzyloxyamino)-caproic acid, 6-acetamidohexnoic acid, 6-bromohexanoic acid, 6-chloronicotinic acid, 6-hydroxy-2,5,7,8-tetramethyl-chroman-2-carboxylic acid, 6-methylchromone-2-carboxylic acid, 6-methylnicotinic acid, 6-nitrocaproic acid, 6-oxoheptaoic acid, 6-phenylhexanoic acid, 7-(carboxymethyoxy)-4-methylcoumarin, 7-hydroxycoumarin-4-acetic acid, 7-methoxy-2-benzofuran-carboxylic acid, 7-methoxycoumarin-4-acetic acid, 7-oxoctanoic acid, 9-anthracenecarboxylic acid, 9-fluoreneacetic acid, 9-fluorenone-1-carboxylic acid, A,a,a-trifluoro-m-toluic acid, a-acetamidocinnamic acid, abietic acid, acetic acid, acetic acid, acetic acid, acetyl-L-asparagine, acetylsalicyclic acid, acetylsalicylic acid, a-cyano-4-hydroxycinnamic acid, adipic acid monoethyl ester, a-hydroxyhippuric acid, anthranilic acid, anti-3-oxotricyclo[2.2.1.02,6]heptane-7-carboxylic acid, a-phenylcyclopentaneacetic acid, a-phenyl-o-toluic acid, Atrolactic acid, benzilic acid, benzotriazole-5-carboxylic acid, benzoylformic acid, bis(4-chlorophenyl)acetic acid, carbobenzyloxy-DL-alanine, carbobenzyloxy-L-alanine, carbobenzyloxy-1-glutamine, carbobenzyloxy-L-valine, cis-2-methoxycinnamic acid, Crotonic acid, cyclohexanebutyric acid, cyclohexanecarboxylic acid, cyclohexanepentanoic acid, cyclohexanepropionic acid, cyclopentylacetic acid, D,L-3,4-dihydroxymandelic acid, D-3-phenyllactic acid, decanoic acid, dicyclohexylacetic acid, diethylphosphonoacetic acid, dikegulac hydrate, diphenylacetic acid, fumaric acid monoethyl ester, fumaric acid, gallic acid, geranic acid, glycolic acid, heptadecafluorononanoic acid, heptanoic acid, hexanoic acid, hippuric acid, hydrocinnamic acid, indole-3-carboxylic acid, indole-4-carboxylic acid, isovaleric acid, L-3-phenyllactic acid, Laurie acid, L-Lactic acid (85%), maleamic acid, methoxyacetic acid, mono-(1R)-(–)-menthyl phthalate, mono-(1S)-(+)-menthyl phthalate, mono-methyl cis-5-norbornene-endo-2,3-dicarboxylate, mono-methyl phthalate, mono-methylterephthalate, N-(2-furoyl)glycine, n-(3,5-dinitrobenzoyl)-DL-a-phenylglycine, N-(3-indolylacetyl)-L-alanine, N-(3-indolylacetyl)-L-isoleucine, N-(3-indolylacetyl)-L-leucine, N-(3-indolylacetyl)-L-phenylalanine, N-(3-indolylacetyl)-L-valine, N-(carbobenzyloxy)-1-phenyl-alanine, N,N-diethyl-3,6-difluoro-phthalamic acid, N—[(R)-1-(1-naphthyl)ethyl]-phthalamic acid, N-[5-(trifluoromethyl)-2-pyridyl]-L-valine, n-acetyl-4-fluoro-DL-phenylalanine, N-acetyl-DL-tryptophan, n-acetyl-1-leucine, N-acetyl-L-methionine, N-acetyl-L-phenylalanine, N-acetyl-L-phenylalanine, n-acetyl-1-tyrosine, N-benzoyl-(2R,3S)-3-phenyl-isoserine, N-benzoyl-L-threonine, N-carbobenzyloxy-2-methyl-alanine, N-carbobenzyloxy-L-glutamic acid 1-methyl ester, N-carbobenzyloxy-L-isoleucine, N-carbobenzyloxy-L-Leucine, n-carbobenzyloxy-1-threonine, n-ethoxycarbonyl-1-phenylalanine, nonanoic acid, N-p-tosylglycine, N-p-tosyl-L-phenylalanine, o-anisic acid, p-anisic acid, pentafluorobenzoic acid, phenoxyacetic acid, phenylacetic acid, podocarpic acid, pyruvic acid, rhodanine-3-acetic acid, S-(thiobenzoyl)thioglycolic acid, s-benzyl-n-carbobenzyloxy-1-cysteine, Sebacic acid monomethyl ester, succinamic acid, succinic 2,2-dimethyl-hydrazide, tetrahydro-2-furoic acid, trans-1-acetyl-4-hydroxy-L-pro line, trans-2,3-dimethoxycinnamic acid, trans-2,4-dichlorocinnamic acid, trans-2,4-difluorocinnamic acid, trans-2,5-difluorocinnamic acid, trans-2,6-difluorocinnamic acid, trans-2-chloro-6-fluro-cinnamic acid, trans-2-hexenoic acid, trans-3-(2,3,5,6-tetramethyl-benzoyl)acrylic acid, trans-3-(2,5-dimethylbenzo-yl)-acrylic acid, trans-3-(4-ethoxy-benzoyl)acrylic acid, trans-3-(4-methoxy-benzoyl)-acrylic acid, trans-3-(4-methylbenzoyl)-acrylic acid, trans-3,4-difluorocinnamic acid, trans-3-fluorocinnamic acid, trans-3-furanacrylic acid, trans-3-hexenoic acid, trans-4-chloro-3-nitrocinnamic acid, trans-4-hydroxy-3-methoxy-cinnamic acid, trans-4-hydroxy-3-methoxy-cinnamic acid, trans-4-methyl-1-cyclohexa-ne carboxylic acid, trans-4-pentylcyclohexane carboxylic acid, trans-5-bromo-2-methoxy cinnamic acid, trans-Styrylacetic acid, trans-Styrylacetic acid, tridecafluoroheptanoic acid, trimethylacetic acid, triphenylacetic acid, Valeric acid, and Yohimbinic acid, mono-hydrate, or a pharmaceutically acceptable salts thereof, in a therapeutically effective amount.

2. The method of claim 1, wherein the disease treatable by inhibiting or reducing the activity of the protein tyrosine phosphatase is selected from the group consisting of type 1 diabetes, type 2 diabetes, obesity, metabolic syndrome, Crohn's disease, rheumatoid arthritis, Graves' disease, systemic lupus erythematosus, leukemia, and tuberculosis.

3. The method of claim 1, wherein the protein tyrosine phosphatase comprises TC-PTP and PTP1B.

4. A method of inhibiting TC-PTP in a human patient, comprising the steps of:
administering to a human patient a compound having the following formula:

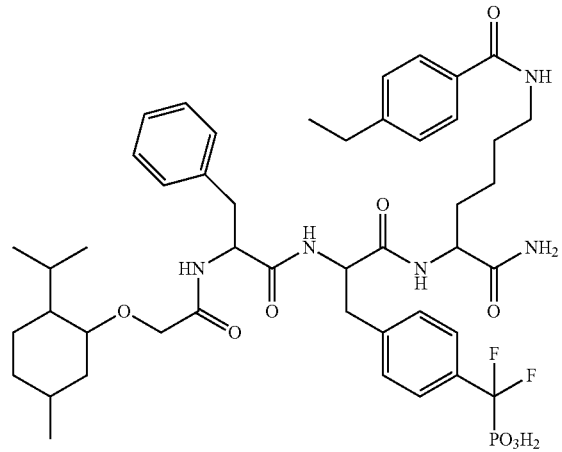

or a pharmaceutically acceptable salt thereof, in a therapeutically effective amount; wherein the disease treatable by inhibiting TC-PTP is type 1 diabetes.

5. The method of claim 2, wherein the disease treatable by inhibiting or reducing the activity of the protein tyrosine phosphatase is type 1 diabetes.

6. The method of claim 1, wherein $R^1$ or $R^2$ is

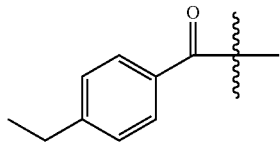

7. The method of claim 1, wherein R¹ or R² is
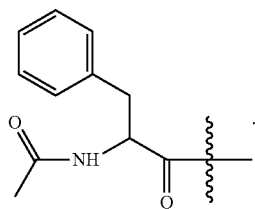 [SMILES: *C(=O)C(Cc1ccccc1)NC(C)=O]
8. The method of claim 1, wherein R¹ of R² is
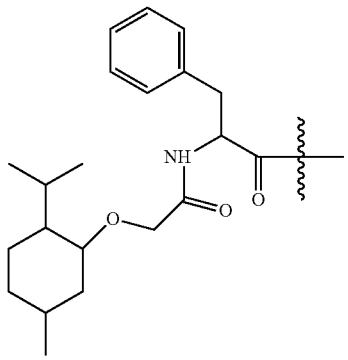
9. The method of claim 1, the at least one compound is a compound having the formula:
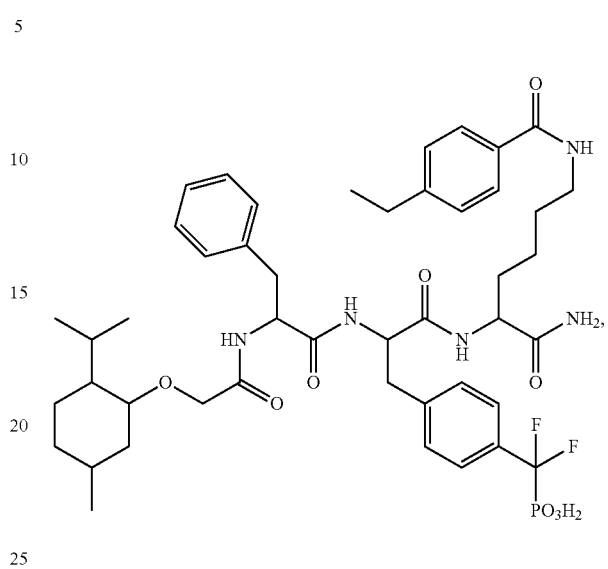
or a pharmaceutically acceptable salts thereof.
* * * * *